(12) United States Patent
Moon et al.

(10) Patent No.: US 12,239,378 B2
(45) Date of Patent: Mar. 4, 2025

(54) SYSTEMS, METHODS, AND APPARATUSES FOR EYE IMAGING, SCREENING, MONITORING, AND DIAGNOSIS

(71) Applicant: EYENUK, INC., Woodland Hills, CA (US)

(72) Inventors: Ji Sun Moon, Tarzana, CA (US); Malavika Bhaskaranand, Woodland Hills, CA (US); Chaithanya Amai Ramachandra, West Hills, CA (US); Gregory John Alexander Russell, Woodland Hills, CA (US); Kaushal Mohanlal Solanki, West Hills, CA (US)

(73) Assignee: EYENUK, INC., Woodland Hills (CA)

( * ) Notice: Subject to any disclaimer, the term of this patent is extended or adjusted under 35 U.S.C. 154(b) by 857 days.

(21) Appl. No.: 17/331,588

(22) Filed: May 26, 2021

(65) Prior Publication Data
US 2021/0353141 A1    Nov. 18, 2021

Related U.S. Application Data

(63) Continuation of application No. PCT/US2019/063230, filed on Nov. 26, 2019.
(Continued)

(51) Int. Cl.
*A61B 3/12* (2006.01)
*A61B 3/00* (2006.01)
*A61B 3/15* (2006.01)

(52) U.S. Cl.
CPC .............. *A61B 3/12* (2013.01); *A61B 3/0008* (2013.01); *A61B 3/156* (2013.01)

(58) Field of Classification Search
CPC ......... A61B 3/12; A61B 3/0008; A61B 3/156; A61B 3/10; A61B 3/0025; A61B 3/103; A61B 3/117; A61B 3/125
(Continued)

(56) References Cited

U.S. PATENT DOCUMENTS

| | | | |
|---|---|---|---|
| 7,167,630 B2 * | 1/2007 | Eyal | G02B 6/4206 385/38 |
| 8,879,813 B1 * | 11/2014 | Solanki | G06T 3/14 382/128 |

(Continued)

OTHER PUBLICATIONS

WO, PCT/US19/63230 ISR and Written Opinion, Mar. 25, 2010.

*Primary Examiner* — Mohammed A Hasan
(74) *Attorney, Agent, or Firm* — One LLP

(57) ABSTRACT

Various embodiments for eye imaging, screening, diagnosis, and monitoring are provided. Some embodiments comprise systems for retinal imaging capable of capturing multiple high resolution images using multiple quick succession flashes. The images can be combined to provide for a complete image of the retina of a target FOV without corneal reflections. In some embodiments, a system for retinal imaging can utilize an optical design pupil layout that allocates a large area for the path of imaging rays on the eye pupil by using a narrow buffer area. In other embodiments, a system for retinal imaging can comprise a main device, including an imaging and sensing device, and a robotic system, including an eye tracker and/or sensors, wherein the robotic system is capable of automatically aligning the main device and selecting an optimal imaging mode by detecting a pupil size of an eye and is combined with an AI analysis tool.

11 Claims, 50 Drawing Sheets

Related U.S. Application Data

(60) Provisional application No. 62/771,462, filed on Nov. 26, 2018.

(58) Field of Classification Search
USPC .......................................................... 351/214
See application file for complete search history.

(56) References Cited

U.S. PATENT DOCUMENTS

| | | | |
|---|---|---|---|
| 2002/0097379 A1* | 7/2002 | Goldfain ................ | A61B 3/158 |
| | | | 351/221 |
| 2009/0225277 A1* | 9/2009 | Gil ........................ | G01J 3/0256 |
| | | | 351/246 |
| 2012/0050683 A1* | 3/2012 | Yates ...................... | A61B 3/12 |
| | | | 351/219 |
| 2015/0146170 A1 | 5/2015 | Su | |
| 2015/0164886 A9 | 6/2015 | Wang et al. | |
| 2018/0303667 A1* | 10/2018 | Peyman ................ | A61B 5/0095 |

\* cited by examiner

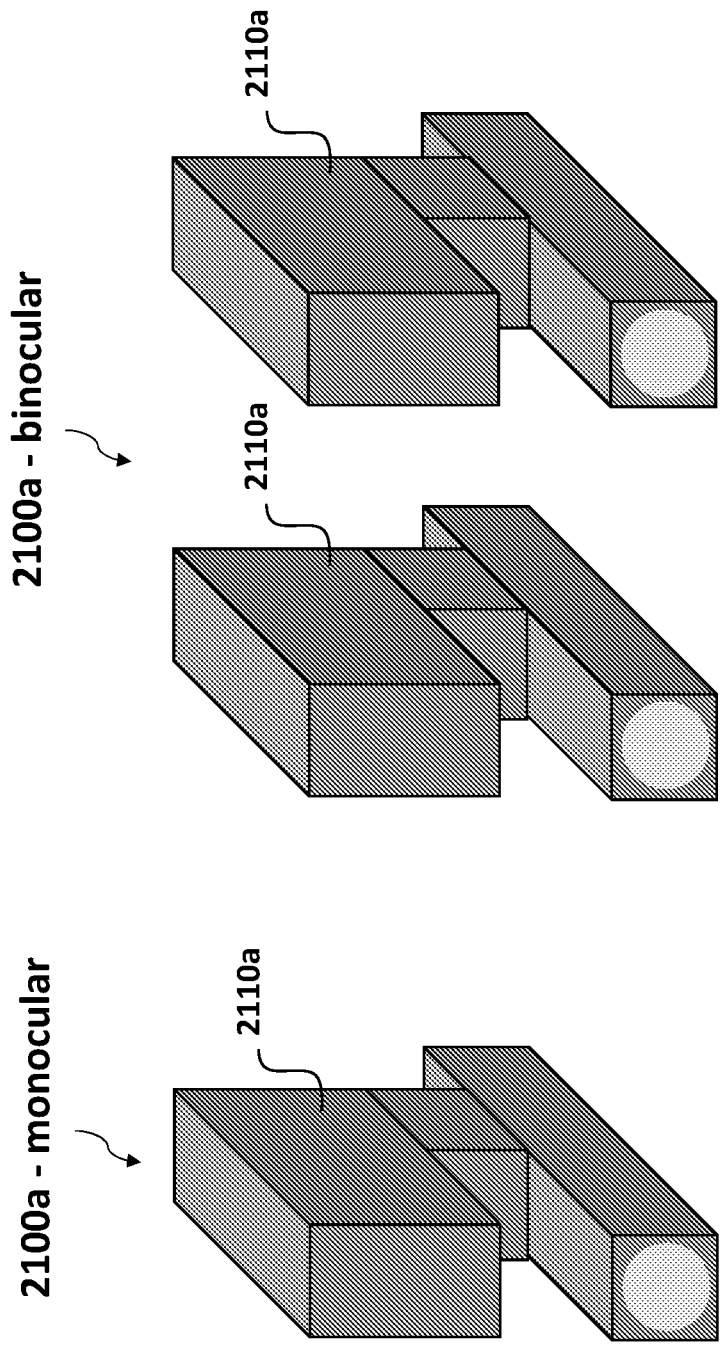

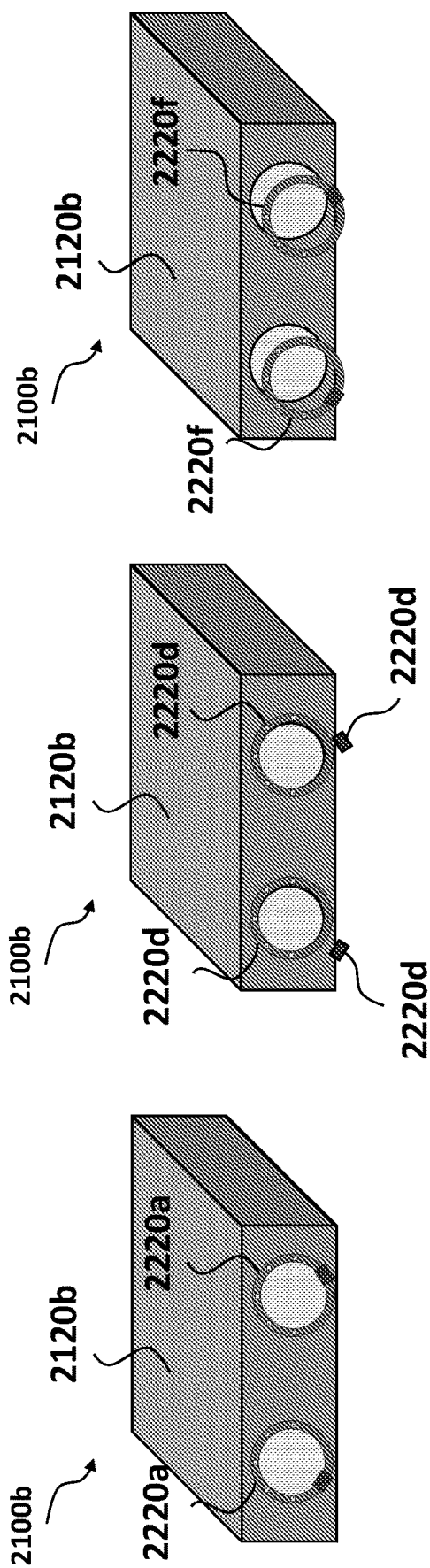

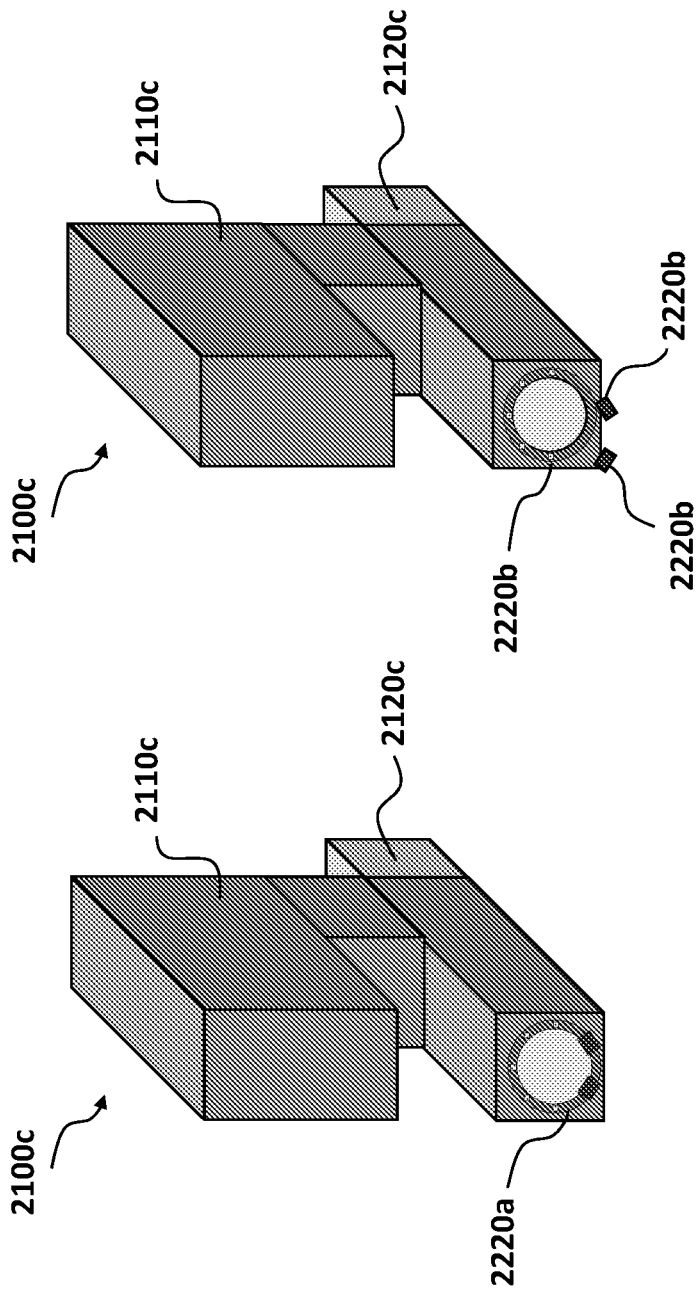

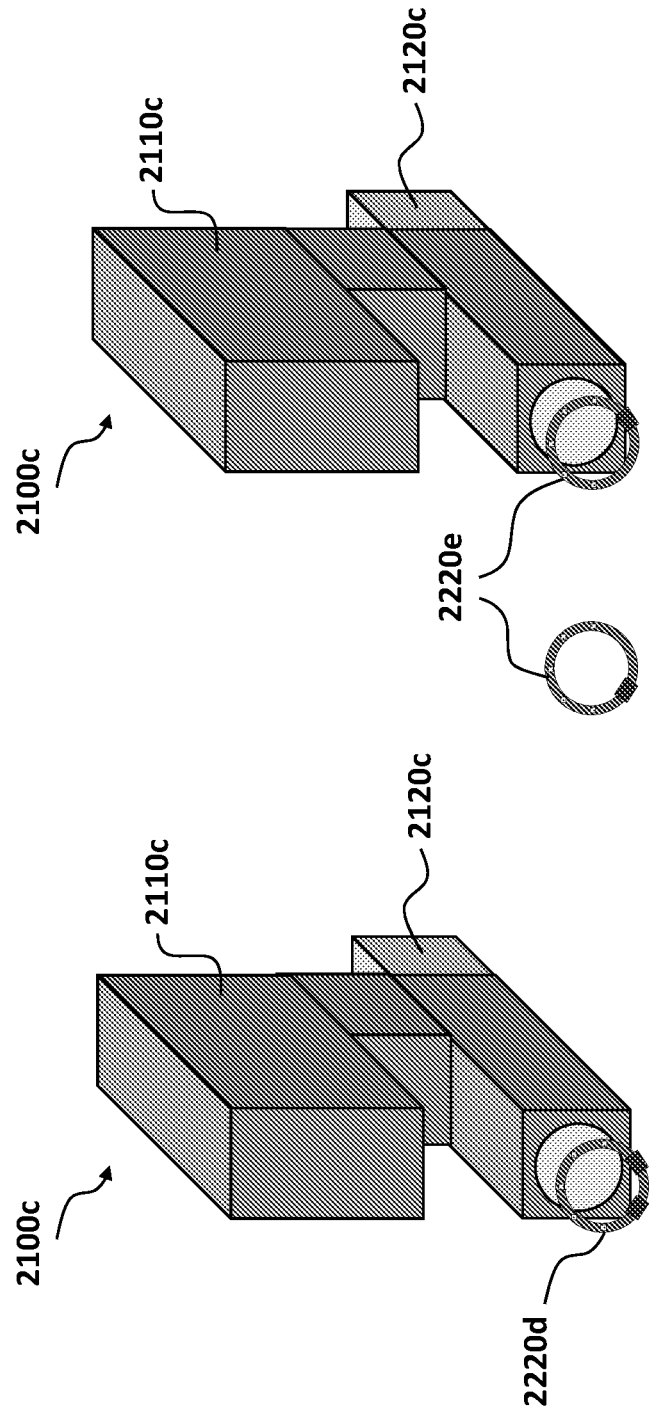

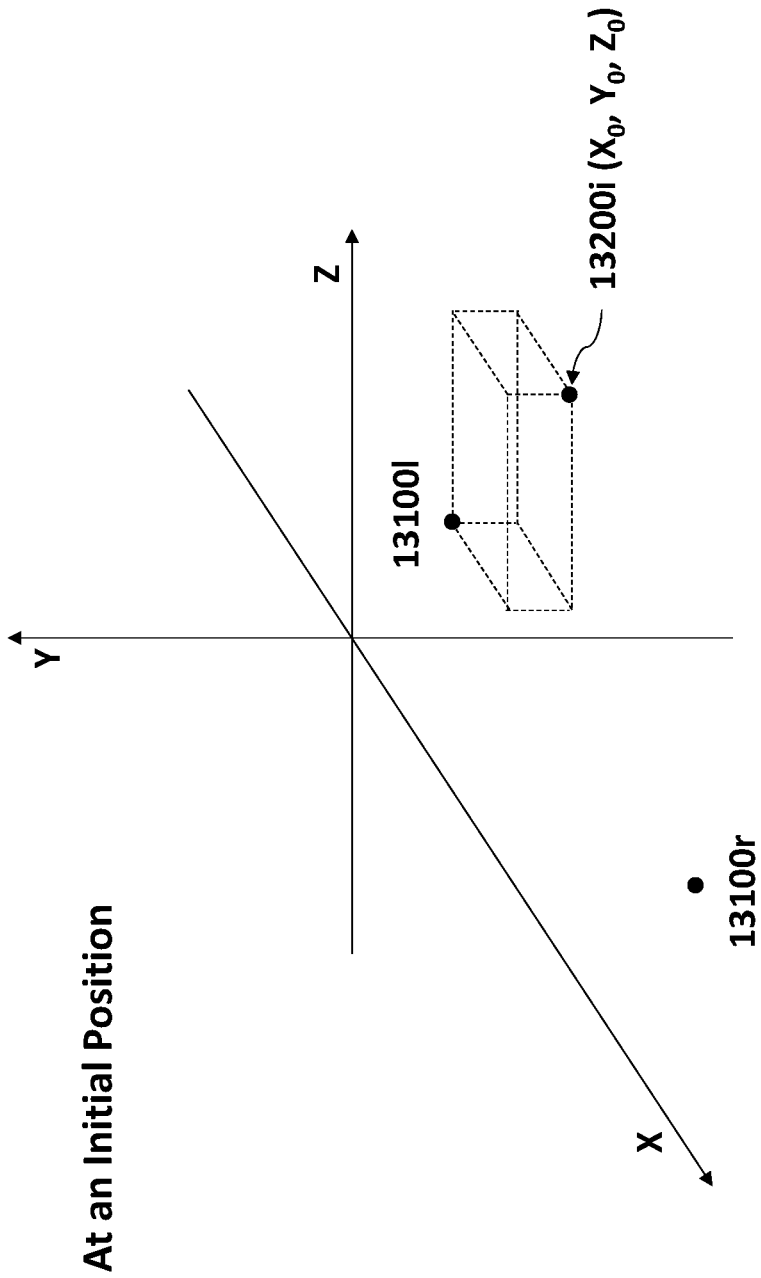

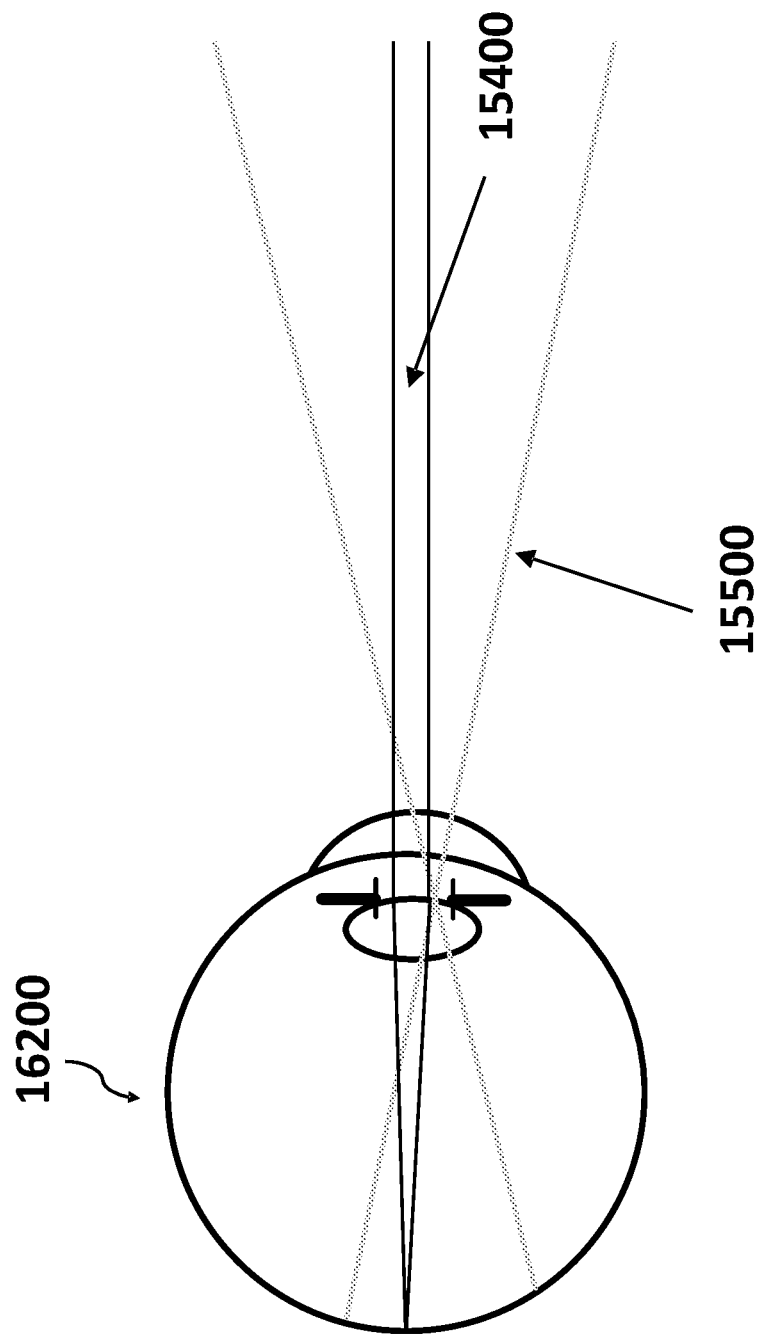

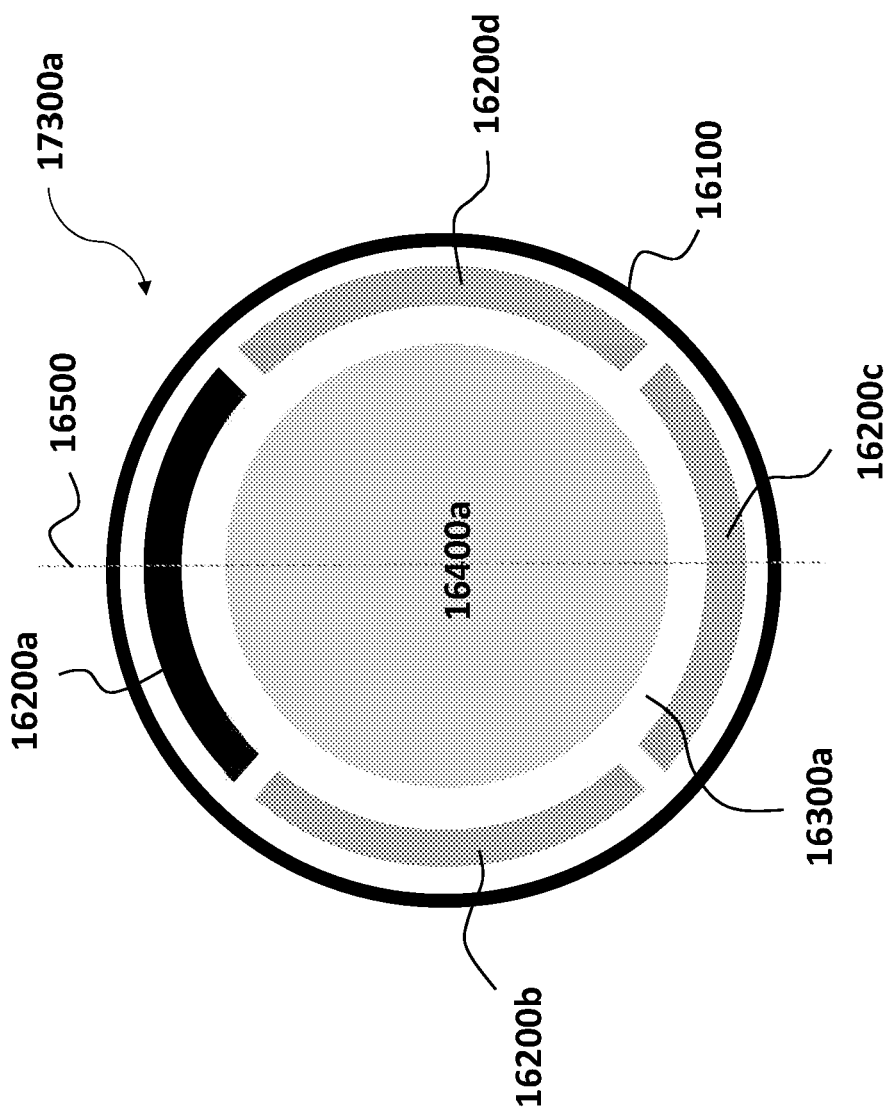

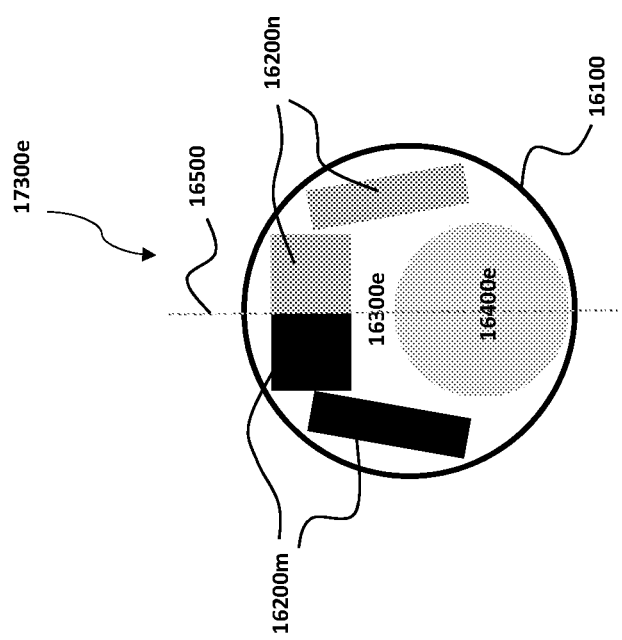

FIG. 21A
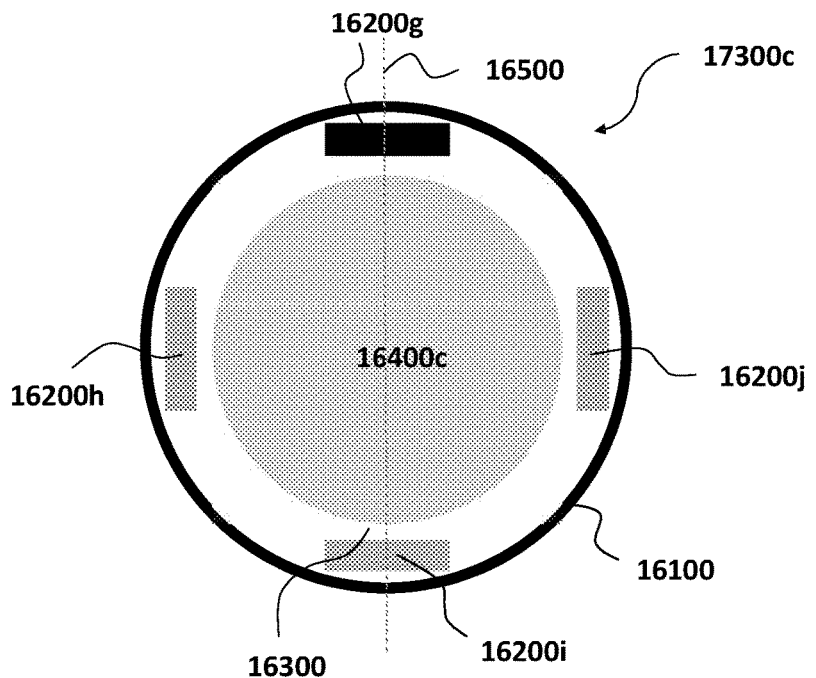
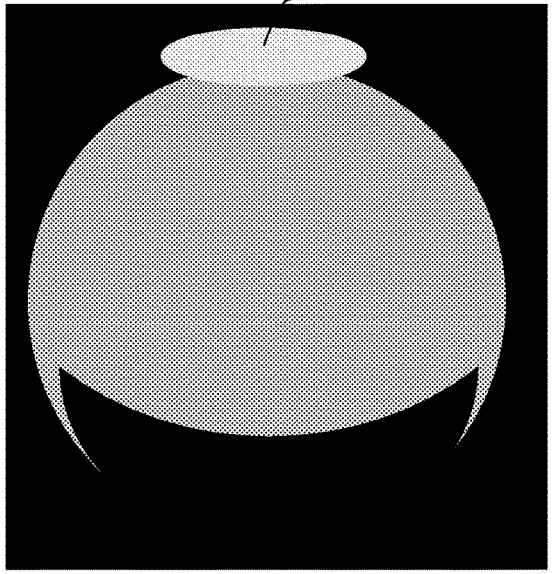
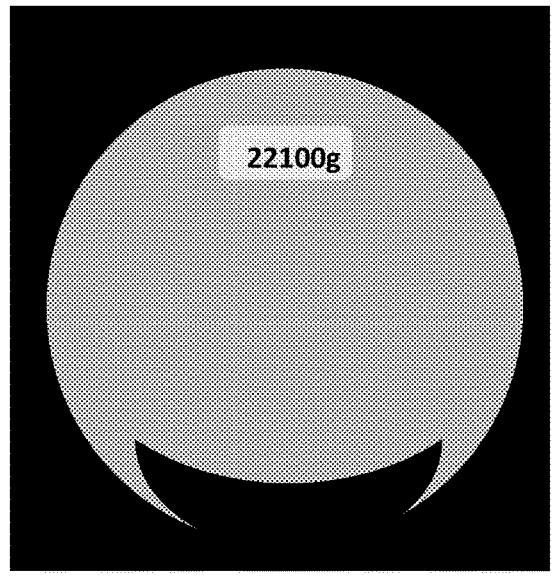
FIG. 21B         FIG. 21C

FIG. 22A
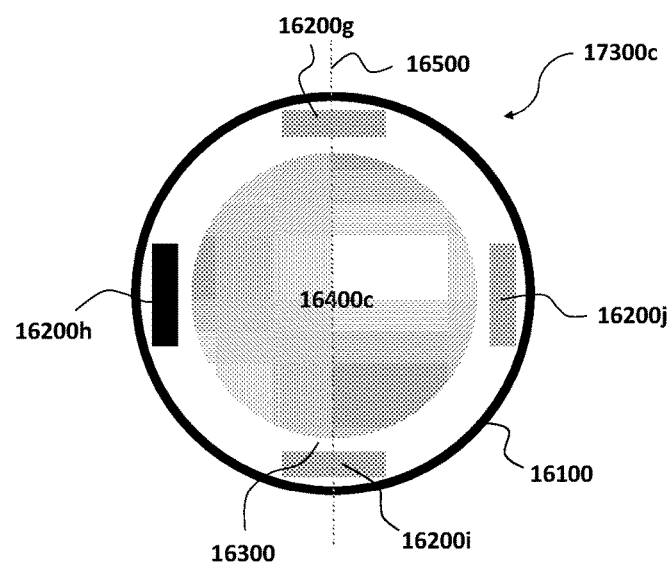
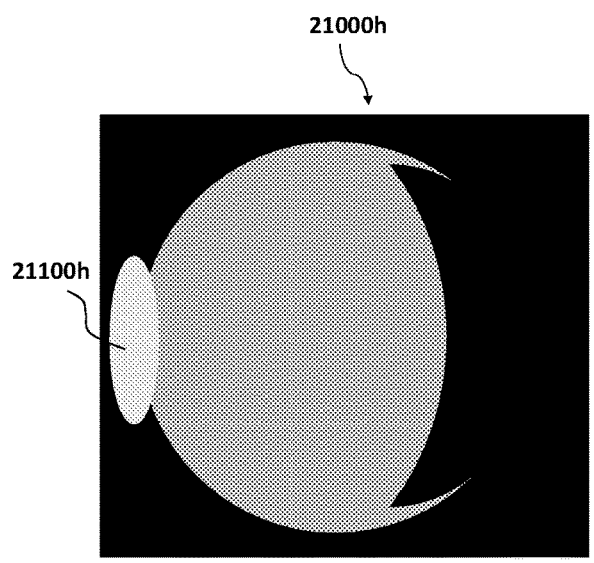
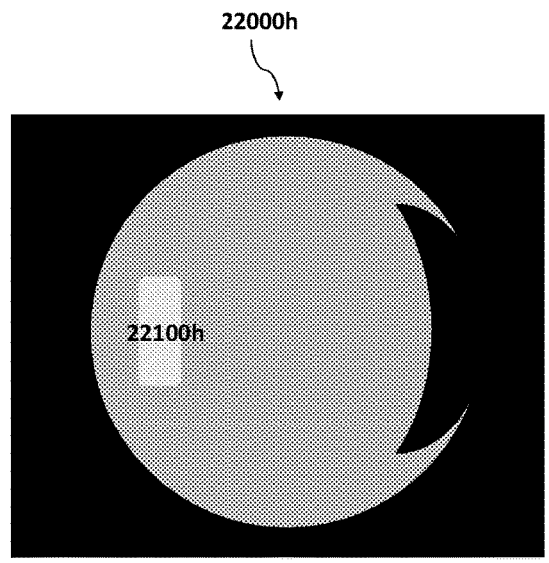
FIG. 22B
FIG. 22C

FIG. 23A
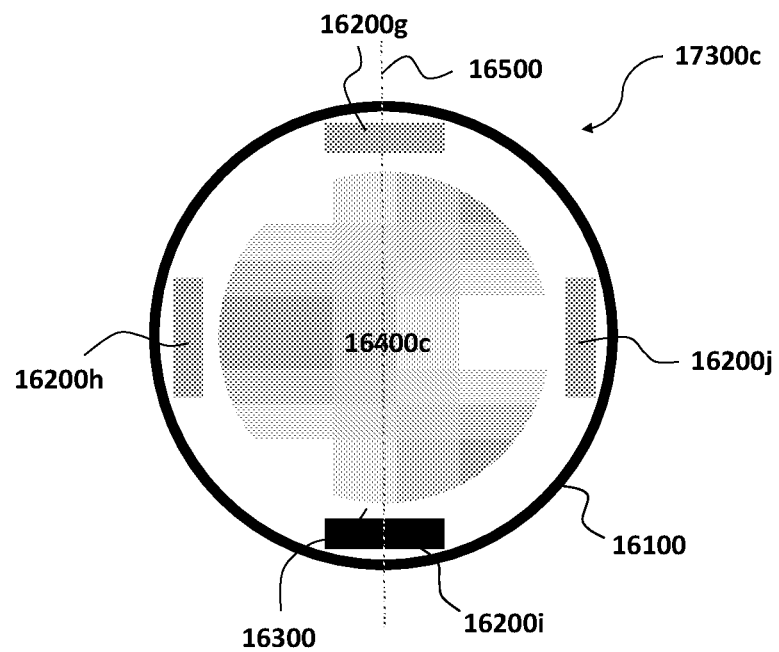
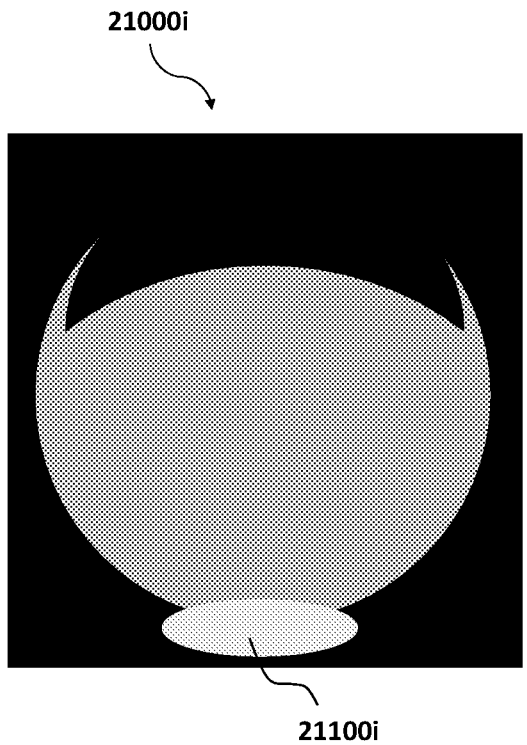
FIG. 23B
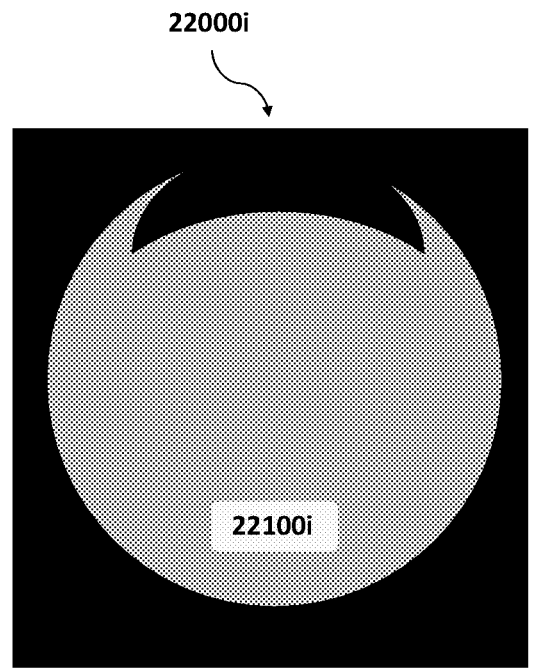
FIG. 23C

FIG. 24A
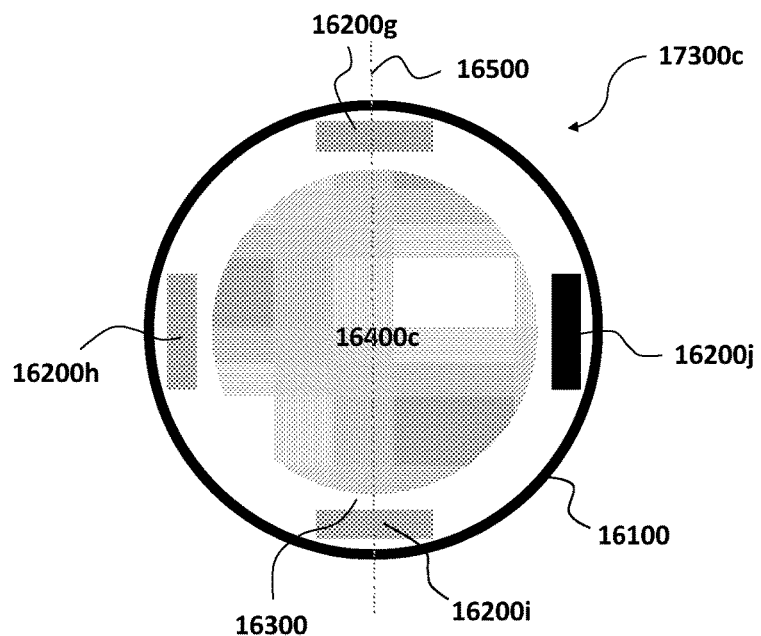
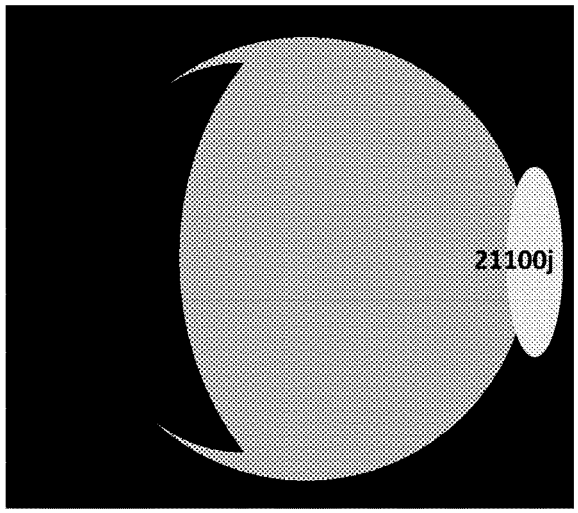
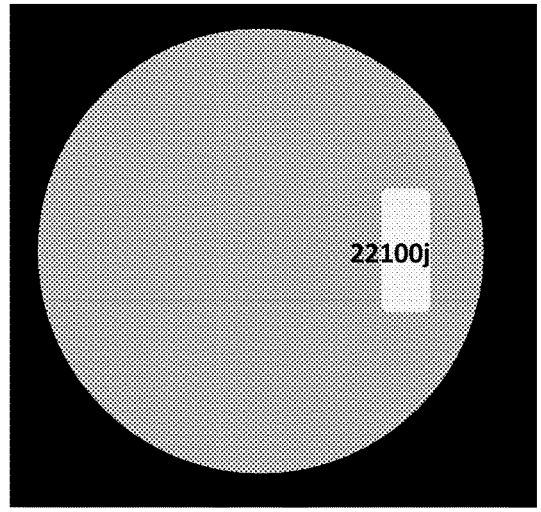
FIG. 24B                FIG. 24C

SYSTEMS, METHODS, AND APPARATUSES FOR EYE IMAGING, SCREENING, MONITORING, AND DIAGNOSIS

CROSS-REFERENCE TO RELATED APPLICATIONS

This application is a continuation of International Application No. PCT/US19/63230, filed Nov. 26, 2019, which claims priority to U.S. Provisional Application Ser. No. 62/771,462, filed Nov. 26, 2018, the disclosures of both of which are hereby expressly incorporated by reference in their entireties for all purposes.

FIELD OF INVENTION

The subject matter described herein relates to systems, methods, and apparatuses for eye imaging, screening, monitoring, and diagnosis.

BACKGROUND

Eyes can provide a significant amount of information about various diseases that not only include eye diseases (e.g., diabetic retinopathy ("DR"), age-related macular degeneration ("AMD"), and glaucoma), but also neurodegenerative diseases (e.g., Alzheimer's disease) and systemic diseases (e.g., cardiovascular diseases). This information can include the results of various eye tests, such as a visual field test, an acuity test, Amsler grid, contrast sensitivity, Snellen chart, LogMAR chart, color blindness test, corneal topography, iridocorneal angle measurement, pachymetry, reflectometer, tonometry, among others. Additionally, other sources of information from the eye can include images or data acquired from sensors, such as color retinal images, three-dimensional ("3D") or stereoscopic images of the retina and/or anterior segments of the eyes, multi- or hyperspectral images of the retina and/or anterior segments of the eyes, retinal images from a scanning laser ophthalmoscope, such as from fluorescein angiography or fundus autofluorescence, and optical coherent tomography ("OCT") images of the retina and/or anterior segment of the eyes, among others.

Currently, some information, such as color retinal images obtained by a fundus camera, can be used for the screening and/or diagnosis of diabetic retinopathy in diabetic patients in order to detect the disease at the early stages and to help prevent blindness. However, the need for eye screening and/or diagnosis in diabetic patients far exceeds the availability of such testing in most parts of the world, including the United States and Europe. This need is even greater if the scope of eye screening and/or diagnosis is extended to other diseases, such as AMD, glaucoma, neurodegenerative diseases, and cardiovascular diseases for patients worldwide. Simply increasing the number of ophthalmologists and trained technicians, however, with current methods of eye screening and/or diagnosis can result in a long delay and would be extremely costly. Moreover, conventional eye screening and/or diagnosis can be limited in underdeveloped economies, as retaining trained technicians in regions of economic deprivation can be challenging.

Accordingly, there is a present need for more efficient, accurate, easily operable, patient-friendly, and cost-effective systems, methods, and/or apparatuses for eye screening, imaging, monitoring, and diagnosis.

SUMMARY

Described herein are example embodiments of systems, methods, and apparatuses for eye imaging, screening, monitoring, and diagnosis. Many of the embodiments described herein can comprise devices and systems that can be manufactured at low cost. In addition, some of these embodiments can be fully automated solutions and self-operable, which can significantly reduce operating costs by minimizing the need for photographers and technicians. According to another aspect of the present disclosure, some embodiments can have a small form factor with a head-mounted and/or wearable gear that can be used, for example, in a waiting room of a hospital or clinic, as well as in an outdoor setting without having a table (which often requires a high-cost height adjustment feature) or a dark room.

Many of the embodiments described herein can provide screening, diagnosis, and/or monitoring results in a relatively short time (e.g., within one minute), without the need for the patient or physician to wait a few days for the results. According to some embodiments, systems are provided for acquiring multiple types of images and/or data, through the use of, for example, multi-spectral imaging, 3D imaging, anterior imaging, virtual reality ("VR") eye tests, and by analyzing the acquired images and/or data and to provide a set of screening, diagnosis, and/or monitoring results for one or more diseases in a timely manner.

In addition, many of the embodiments can utilize devices that can be comfortable for the patients due to the head-mounted and/or wearable design that can be combined with VR applications (e.g., providing entertainment, education, and natural dilation).

Furthermore, embodiments of systems for retinal imaging are provided that are capable of capturing high quality images at a high resolution, a high signal-to-noise ratio ("SNR"), and a high field of view ("FOV"). In this regard, these embodiments can provide highly accurate screening, diagnosis, and monitoring results by combining the captured images with analysis tools of high sensitivities and/or specificities. As described earlier, these embodiments can also include devices having a small form factor and are light-weighted, which can serve more various populations of patients (e.g., patients with limited mobility). Some of the devices of the present disclosure can also acquire image data through a small pupil without dilation (e.g., 2.0 mm, whereas many currently commercially available cameras can image through a 4.0 mm pupil). In this regard, these embodiments can serve a greater population of patients with small pupils.

According to one aspect of the embodiments, an imaging system of a system for retinal imaging can be configured to capture multiple images of a retina using multiple quick succession flashes, wherein each image contains a different portion of a retina image free from corneal reflections. Subsequently, a final image can be combined from the multiple captured images to provide for a complete image of the retina free from corneal reflections. According to another aspect of the embodiments, the multiple captured images also allows for imaging through a small pupil (e.g., 2.0 mm diameter of pupil) with a wide FOV of a combined image (e.g., 60°×60°. In some embodiments, multiple images can be captured in a rapid fashion, wherein the imaging process appears as one flash to the human eye.

According to another aspect of the embodiments, an imaging system of a system for retinal imaging can utilize an optical design pupil layout that allocates a large area of the eye for imaging rays and a narrow buffer area between the illumination path and the path for the imaging rays. Typically, a relatively wide buffer area is required to prevent corneal reflections in retinal images. Many of the embodiments of the present disclosure, however, utilize multiple image captures with regional corneal reflections that can be removed, and thus allows for a relatively narrow buffer area. A large area for the imaging rays on the eye pupil can also provide for images having a high resolution, a high SNR and a high FOV.

According to another aspect of the embodiments, an imaging system of a system for retinal imaging can be configured to use one or more reimaging corrective optics modules to achieve a higher resolution, diopter adjustment/focusing, and change of magnification. In certain embodiments, the imaging portion of a system for retinal imaging can be configured to use a multi-baffle-and-illumination module capable of multiple imaging modes in a single compact device.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 3A and 3B are perspective views of example embodiments of main devices comprising, respectively, a monocular and a binocular imaging/sensing device.

FIGS. 9A, 9B, and 9C are perspective views of example embodiments of eye trackers and main devices comprising a VR device.

FIGS. 10A and 10B are perspective views of example embodiments of eye trackers and main devices comprising a monocular imaging/sensing device integrated with a VR device.

FIGS. 10D and 10E are perspective views of example embodiments of eye trackers and main devices comprising a monocular imaging/sensing device integrated with a VR device.

FIG. 13B is a diagram illustrating an initial or default position of a main device.

FIGS. 15A and 15B are diagrams of an optical design pupil layout utilizing a known method for annular illumination.

FIG. 16A to 16F are diagrams of various example embodiments of optical design pupil layouts of systems for retinal imaging.

FIG. 21A is a diagram of an example embodiment of an optical design pupil layout for a system for retinal imaging.

FIGS. 21B and 21C are diagrams of simulated images from an example embodiment of a system for retinal imaging based on the design illustrated in FIG. 21A.

FIG. 22A is a diagram of an example embodiment of an optical design pupil layout for a system for retinal imaging.

FIGS. 22B and 22C are diagrams of simulated images from an example embodiment of a system for retinal imaging based on the design illustrated in FIG. 22A.

FIG. 23A is a diagram of an example embodiment of an optical design pupil layout for a system for retinal imaging.

FIGS. 23B and 23C are diagrams of simulated images from an example embodiment of a system for retinal imaging based on the design illustrated in FIG. 23A.

FIG. 24A is a diagram of an example embodiment of an optical design pupil layout for a system for retinal imaging.

FIGS. 24B and 24C are diagrams of simulated images from an example embodiment of a system for retinal imaging based on the design illustrated in FIG. 24A.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a," "an," and "the" include plural referents unless the context clearly dictates otherwise.

The systems, methods, and apparatuses described herein relate to eye imaging, screening, monitoring, and diagnosis. Accordingly, many of the embodiments described herein operate by capturing multiple images of a retina using multiple quick succession flashes, wherein each image contains a different portion of a retina image free from corneal reflections. A final image of the retina can be combined from the multiple captured images to provide for a complete image of the retina of a target wide FOV free from corneal reflections. According to an aspect of these embodiments, the multiple captured images allow for imaging through a small pupil (e.g., 2.0 mm diameter) with a wide FOV.

According to another aspect of the embodiments, an imaging system of a system for retinal imaging can utilize an optical design pupil layout that allocates a large area at/near the pupil of the eye for imaging rays and a narrow buffer area between a conjugate of illumination and the path for the imaging rays. Many of the embodiments of the present disclosure utilize multiple image captures with regional corneal reflections that can be removed, and thus allows for a relatively narrow buffer area. A large area for the imaging rays on/near the eye pupil can also provide for images having high resolution, high SNR and high FOV.

According to another aspect of the embodiments, an imaging system of a system for retinal imaging can be configured to use one or more reimaging corrective optics modules to achieve a higher resolution, diopter adjustment/focusing, and change of magnification. In certain embodiments, an imaging system of a system for retinal imaging can be configured to use a multi-baffle-and-illumination module capable of multiple imaging modes in a single compact device.

Before describing more particular aspects of the embodiments in detail, however, it is first desirable to describe examples of devices that can be present within, for example, a system for eye imaging, screening, diagnosis, and monitoring, as well as examples of their operation, all of which can be used with the embodiments described herein.

Figure 1:
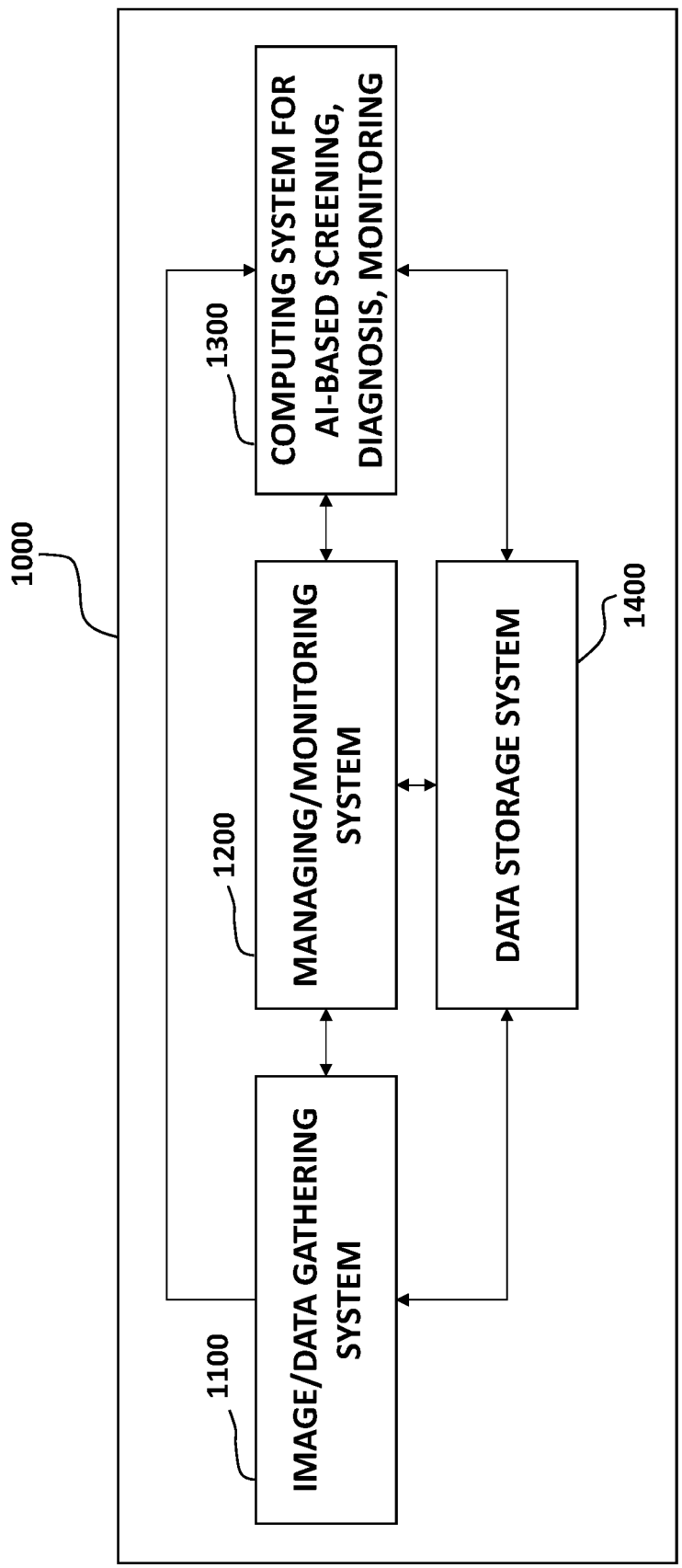
FIG. 1 is a block diagram illustrating an example embodiment of a system for eye imaging, screening, diagnosis, and monitoring.

Example Embodiments of Systems for Eye Imaging, Screening, Diagnosis, and Monitoring FIG. 1 is a block diagram illustrating an example embodiment of a system for eye imaging, screening, diagnosis, and monitoring 1000. According to one aspect of the embodiments, system 1000 is capable of screening, diagnosing, and monitoring diseases of interest in a patient, as well as monitoring various medical and health conditions of the patient. System 1000 can also recommend or provide medical and health programs, and/or other therapies to improve the medical and health conditions of the patient. According to another aspect of the embodiments, system 1000 can comprise an image and data gathering system 1100, a managing and monitoring system 1200, a computing system for AI-based screening, diagnosis, and monitoring 1300, and a data storage system 1400, each of which is described in further detail in the section below and elsewhere throughout the present disclosure. In some embodiments, system 1000 can be simplified and may not include managing and monitoring system 1200.

According to some embodiments, managing and monitoring system 1200 can include a computing system comprising one or more computing processors, non-transitory memory, one or more storage devices, one or more display devices (e.g., a tablet computer, laptop computer, desktop computer, or smartphone), input devices (e.g., a keyboard, mouse, or joystick) and output and communication devices (e.g., microphone and speaker). According to one aspect of the embodiments, managing and monitoring system 1200 can be configured to retrieve information of a patient (e.g., patient ID, patient medical records) from data storage system 1400, and visually output some or all of the retrieved information on a display of managing and monitoring system 1200. In some embodiments, managing and monitoring system 1200 can also be configured to locally store data, including the retrieved information, in non-transitory memory and/or a local storage device.

According to another aspect of the embodiments, the computing system of managing and monitoring system 1200 can be configured to identify a patient by analyzing one or more images and/or videos of the patient's eye (e.g., retina and/or iris), which can be acquired by image and data gathering system 1100. In certain embodiments, managing and monitoring system 1200 can be configured to manage and/or monitor: (1) a process for acquiring images and data, and (2) a process for providing and/or recommending medical and health programs and/or therapies. According to another aspect of the embodiments, managing and monitoring system 1200 can be configured to provide for a plurality of functions and tools relating to the manual operation of image and data gathering system 1100. Managing and monitoring system 1200 can be further configured to temporarily store acquired images and/or data received from image and data gathering system 1100 and, subsequently, transfer the acquired images and/or data to computing system for AI-based screening, diagnosis, and monitoring 1300. According to another aspect of the embodiments, managing and monitoring system 1200 can be further configured to receive one or more reports relating to screening results, diagnosis results, and/or monitoring results received from computing system for AI-based screening, diagnosis, monitoring 1300. In some embodiments, managing and monitoring system 1200 can be further configured to visually display the one or more reports and/or transfer the one or more reports to another device (e.g., printer, another computer). In addition, managing and monitoring system 1200 can be configured to facilitate communications between a staff and/or a physician and the patient being examined.

Referring still to FIG. 1, according to another aspect of the embodiments, computing system for AI-based screening, diagnosis, and monitoring 1300 can comprise one or more computing processors, non-transitory memory, and one or more storage devices. The non-transitory memory and/or the one or more storage devices can be configured to store software instructions that, when executed by the one or more computing processors, cause the computing system for AI-based screening, diagnosis, and monitoring 1300 to: analyze images/data acquired from image and data gathering system 1100 and/or data transferred from data storage system 1400; screen, diagnose and/or monitor diseases; and monitor the medical and health conditions of a patient. In some embodiments, computing system for AI-based screening, diagnosis, and monitoring 1300 can comprise a cloud computing system and/or one or more local computers (e.g., one or more computer systems in a hospital/clinic). Furthermore, those of skill in the art will appreciate that, in some embodiments, one or more components and/or devices of managing and monitoring system 1200 and/or image and data gathering system 1100 can comprise computing system for AI-based screening, diagnosis, and monitoring 1300.

According to another aspect of the embodiments, data storage system 1400 can be configured to store electronic medical records ("EMRs") and/or electronic health records ("EHRs"), and can comprise one or more cloud computing systems and/or local external data storage systems or non-transitory memories of one or more computer systems in a hospital/clinic setting.

Example Embodiments of Image and Data Gathering Systems

FIGS. 2A, 2B, 2C, 3A, 3B, 4, 5A, and 5B, 6, 7A, 7B, 7C, 7D, 7E, 8A, 8B, 8C, 9A, 9B, 9C, 10A, 10B, 10C, 10D, 10E, 11A, 11B, and 11C depict various example embodiments of image and data gathering system 1100, and their various componentry, all of which are described in further detail below. According to one aspect of the embodiments, image and data gathering system 1100 can be configured to acquire one or more images and/or data from a patient for screening, diagnosing, and monitoring diseases, and/or monitoring the medical and health conditions of the patient. In certain embodiments, image and data gathering system 1100 can be configured to operate in a fully-automatic mode or a self-operable mode by default and, optionally, with a manual override function. According to one aspect of the embodiments, image and data gathering system 1100 can be configured to acquire images and/or data from a patient, wherein the images and/or data can comprise images, videos, and/or medical test results. In some embodiments, image and data gathering system 1100 can be configured to transfer acquired images and/or data directly to computing system for AI-based screening, diagnosis, and monitoring 1300 (as shown in FIG. 1). In other embodiments, image and data gathering system 1100 can be configured to transfer acquired images and/or data to managing and monitoring system 1200 (as shown in FIG. 1). Subsequently, the acquired images and/or data can then be transferred to computing system for AI-based screening, diagnosis, and monitoring 1300. According to one aspect of the embodiments, the acquired images and/or data can be transferred wirelessly according to a standard wireless communication protocol (e.g., Bluetooth, wireless fidelity (Wi-Fi), and 5G/6G wireless), or via wired communications.

In some embodiments, computing system for AI-based screening, diagnosis, and monitoring 1300 can be configured to analyze the acquired images and/or data. In other embodiments, the acquired images and/or data can be transferred or otherwise displayed to a physician, eye care specialist, or a grader for purposes of screening, diagnosis, and monitoring diseases, and/or monitoring the medical and health conditions of a patient.

Figure 2A:
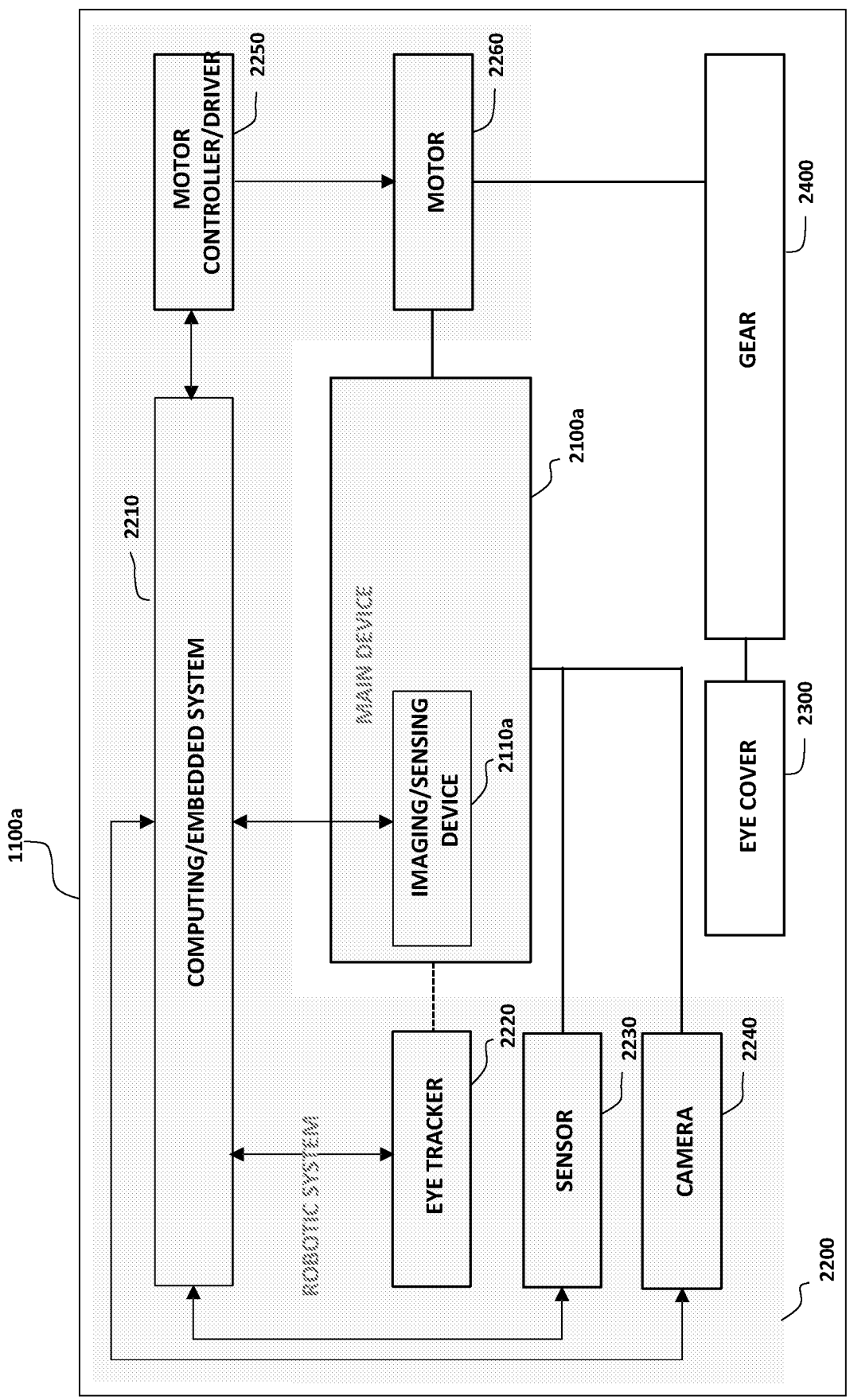
FIG. 2A is a block diagram illustrating an example embodiment of an image and data gathering system comprising an imaging/sensing device.
Figure 2B:
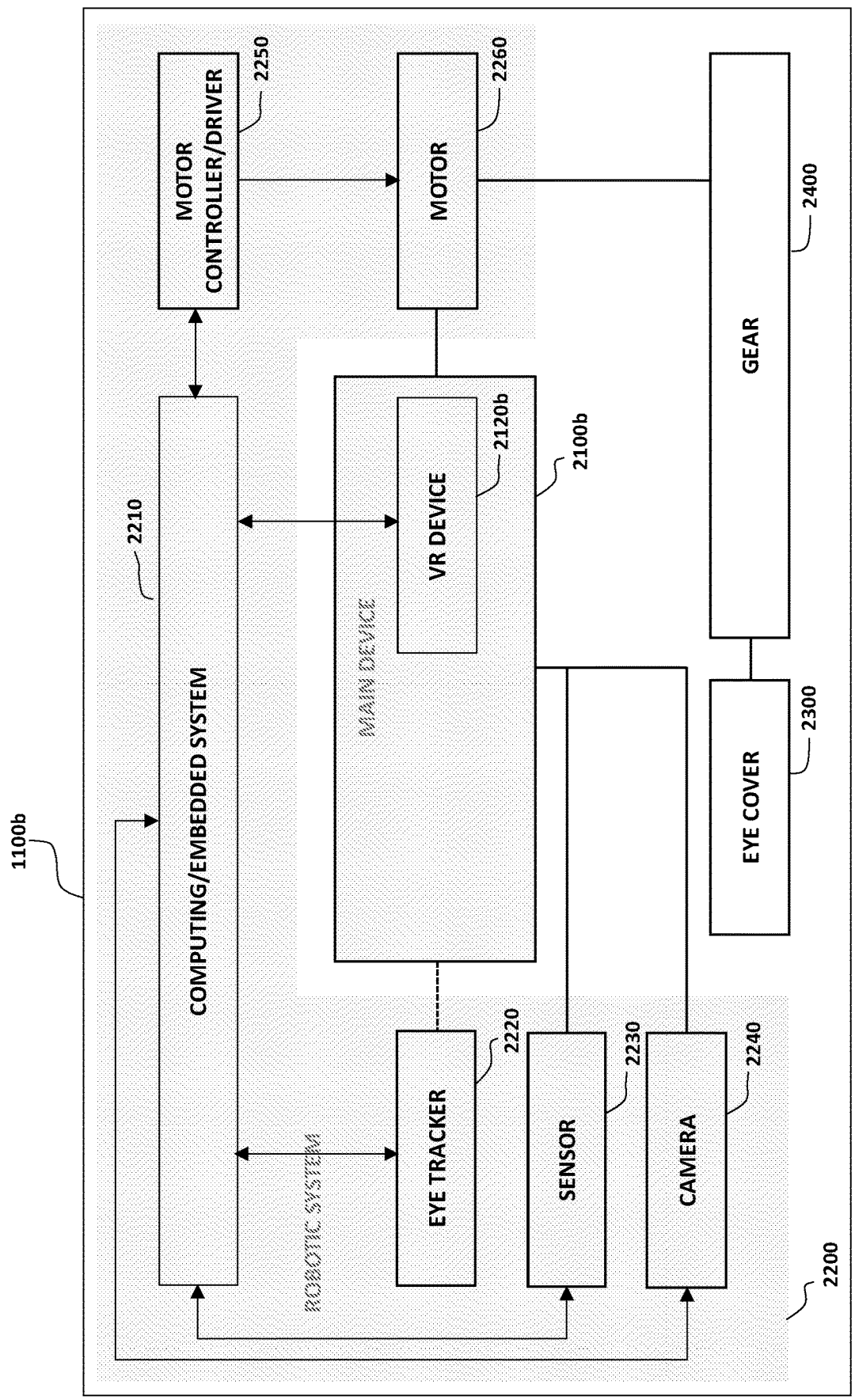
FIG. 2B is a block diagram illustrating an example embodiment of an image and data gathering system comprising a virtual reality ("VR") device.
Figure 2C:
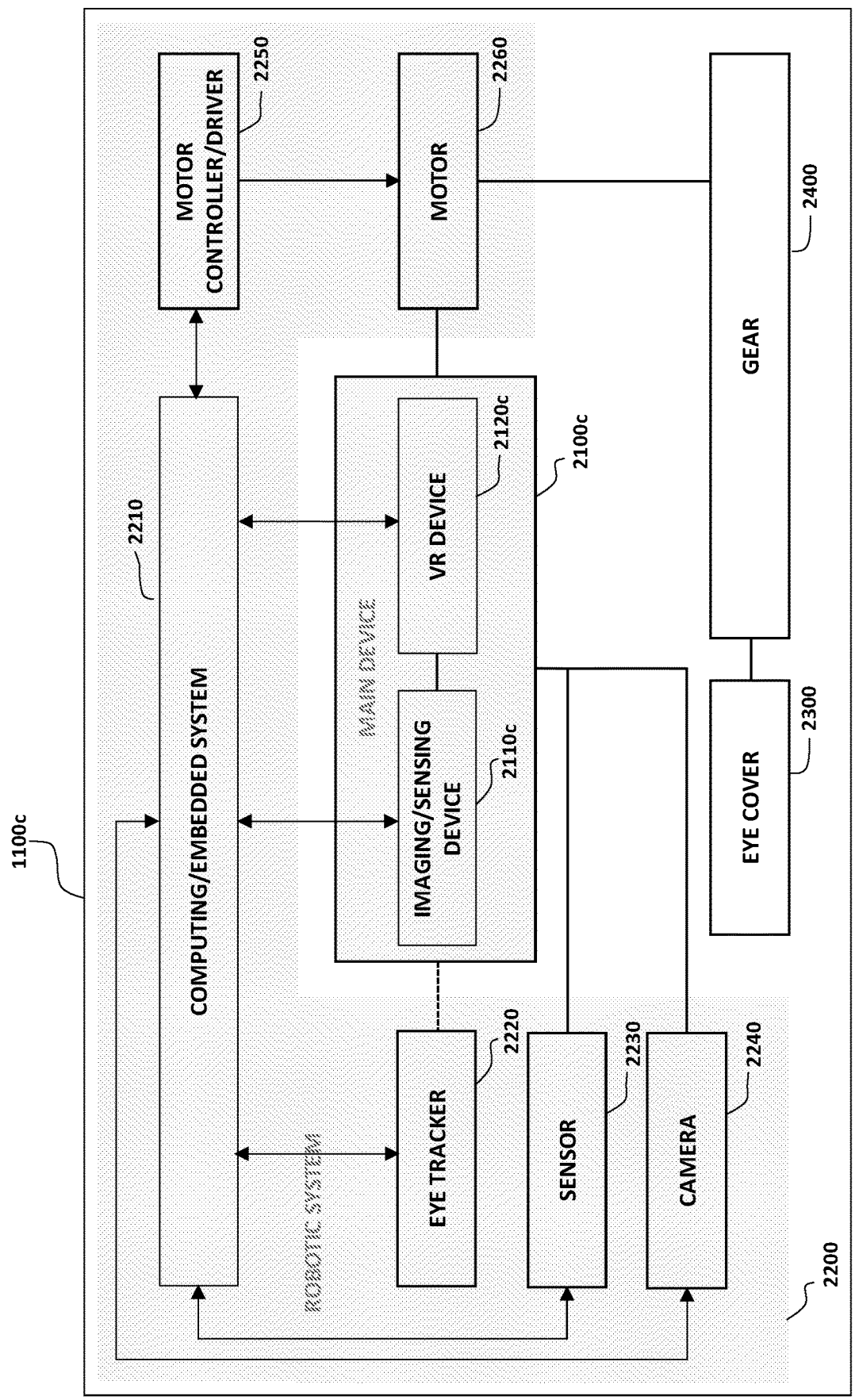
FIG. 2C is a block diagram illustrating an example embodiment of an image and data gathering system comprising an imaging/sensing device and a VR device.

Referring to the block diagrams depicted in FIGS. 2A, 2B, and 2C, according to one aspect of the embodiments, image and data gathering system 1100 (1100a, 1100b, or 1100c) can include a main device (2100a, 2100b, or 2100c), robotic system 2200, eye cover 2300, and gear 2400. However, according to some embodiments, image and data gathering system 1100 (1100a, 1100b, or 1100c) can be simplified by not including eye cover 2300 and/or gear 2400. According to other embodiments, image and data gathering system 1100 (1100a, 1100b, or 1100c) can replace robotic system 2200 with another robotic system. For example, in some embodiments, robotic system 2200 can be replaced with an existing robotic system that can be configured to automatically align a retinal imaging device. According to some embodiments, eye cover 2300 can be configured to be positioned near the eyes of a patient. In this regard, eye cover 2300 can be configured to block one or both eyes of a patient from ambient light, in a similar way to wearable VR devices, which can induce natural pupil dilation without using a pupil dilation medicine or using a dark room for the examination. In some embodiments, eye cover 2300 can be attached to gear 2400, which can be detached from main device 2100 (2100a, 2100b, 2100c) and components of robotic system 2200 (e.g., eye tracker 2220, sensor 2230, camera 2240, and motor 2260). In addition, according to some embodiments, eye cover 2300 can be configured to be cleaned easily and/or easily replaceable or disposable from the other components of image and data gathering system 1100 (1100a, 1100b, 1100c).

According to another aspect of the embodiments, gear 2400 can be configured to be worn on the head or on the face of a patient and to position main device 2100 (2100a, 2100b, 2100c) near the eyes of a patient in a stable way (head-mount/wearable). For example, in some embodiments, gear 2400 can be a head-mounted device configured such that a relatively large portion of the weight of image and data gathering system 1100 (1100a, 1100b, 1100c) can be supported by the patient's head.

Referring to FIGS. 2A, 3A, and 3B, in some embodiments of image and data gathering system 1100a, main device 2100a can comprise an imaging/sensing device 2110a. According to some embodiments, imaging/sensing device 2110a can comprise a system for retinal imaging, as described in further detail below. According to other embodiments, imaging/sensing device 2110a can comprise a system for retinal imaging and a combination of other imaging/sensing systems, including but not limited to one or more of a retinal OCT, 3D/stereo retinal imaging, multi-spectral/hyper-spectral retinal imaging, anterior chamber color imaging, anterior chamber OCT, direct ophthalmoscope, and/or high speed video.

Figure 4:
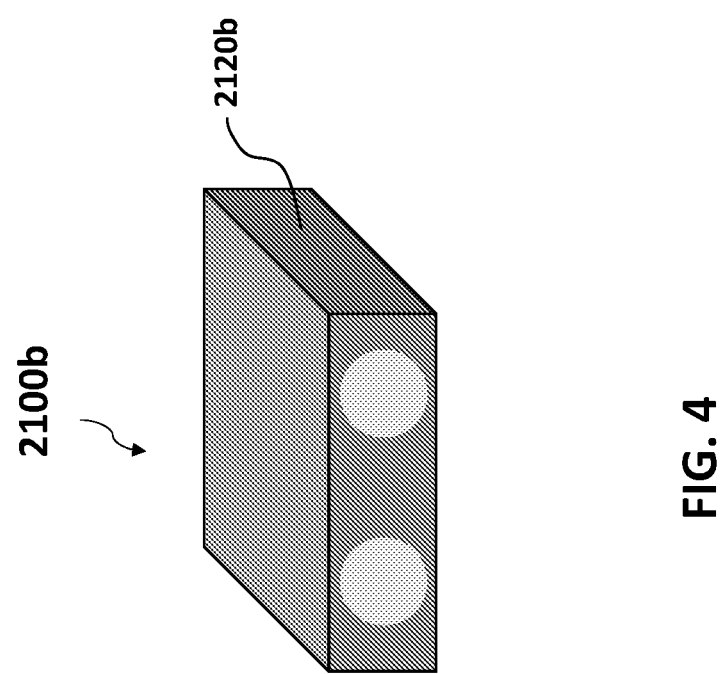
FIG. 4 is a perspective view of an example embodiment of a main device comprising a VR device.

Referring to FIGS. 2B and 4, according to another embodiment of image and data gathering system 1100b, main device 2100b can comprise a virtual reality ("VR") device 2120b, which can be configured for use in multiple medical tests and with various medical and health programs and/or therapies. These medical tests can include but are not limited to: visual field tests, acuity tests, Amsler grid, contrast sensitivity, Snellen chart, LogMAR chart, color blindness test, corneal topography, iridocorneal angle measurement, pachymetry, reflectometer, tonometer and cognitive tests, amongst others. If the patient is a baby or young child, the medical tests can also include but are not limited to: response to light, pupil response, ability to follow a target, visually evoked response test, cover and uncover test, visual acuity test, color test, and cognitive tests, amongst others. In addition, medical and health programs and/or therapies can include but are not limited to: pain management, stroke care, glucose monitoring, sleep cycle management, baby care, entertainment and comforting programs, and eye training and eye exercise programs, amongst others. Those of skill in the art will appreciate that other medical tests, medical and health programs, and therapies, as well as their known variants, can be utilized with the embodiments described herein, and are fully within the scope of the present disclosure.

Figures 5A, 5B:
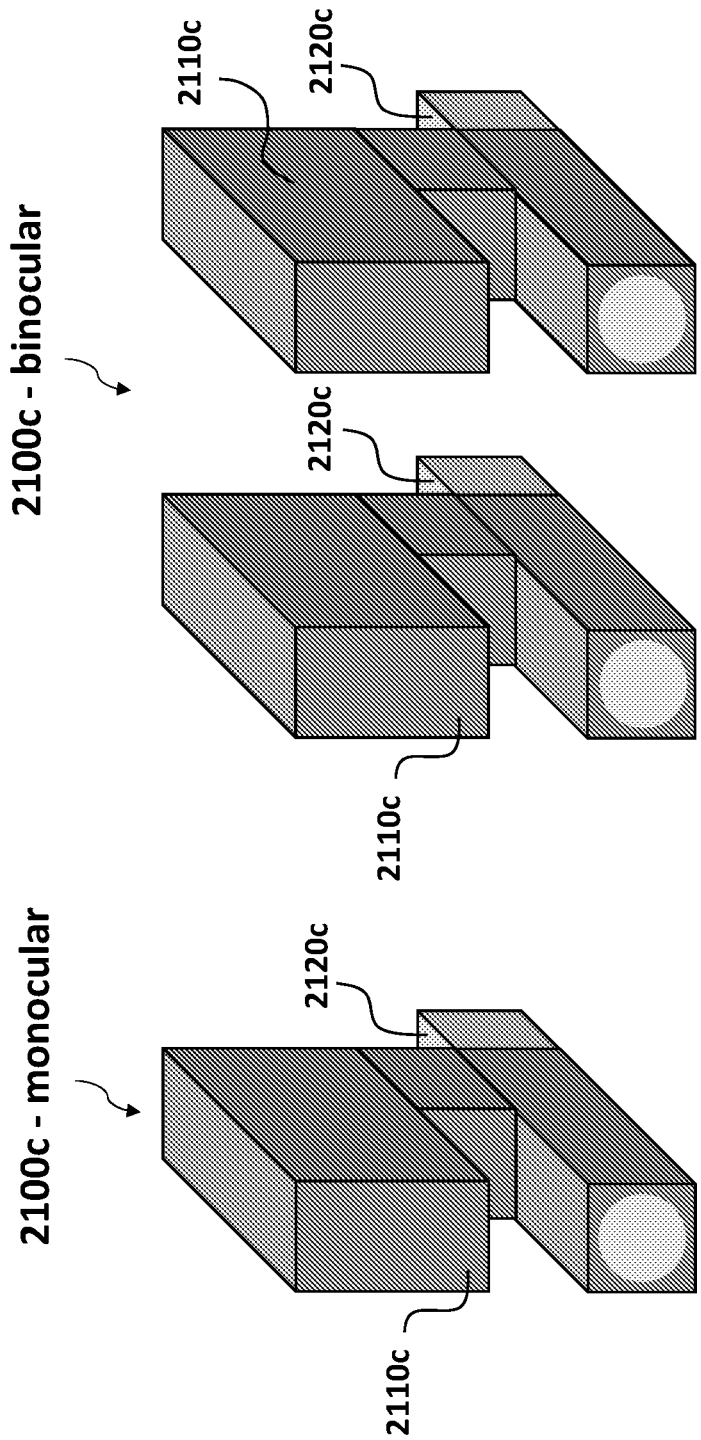
FIGS. 5A and 5B are perspective views of example embodiments of main devices comprising, respectively, a monocular imaging/sensing device integrated with a VR device and a binocular imaging/sensing device integrated with a VR device.

Referring to FIGS. 2C, 5A, and 5B, according to another embodiment of image and data gathering system 1100c, main device 2100c can comprise an imaging/sensing device 2110c and VR device 2120c. Imaging/sensing device 2110c can be the same or similar device as imaging/sensing device 2110a (as shown in FIGS. 2A, 3A, and 3B) and VR device 2120c can be the same or similar device as VR device 2120b (as shown in FIGS. 2B and 4). However, as can be seen in FIG. 2C, imaging/sensing device 2110c and VR device 2120c can be integrated into a single device (as shown in FIGS. 5A, 5B), whereas imaging/sensing device 2110a and VR device 2120b can be separate devices (as shown in FIGS. 3A, 3B and 4).

Referring again to FIGS. 2A, 2B, and 2C, according to another aspect of the embodiments, robotic system 2200 can be configured to perform an automatic alignment of main device (2100a, 2100b, or 2100c). Robotic system 2200 can comprise computing/embedded system 2210, eye tracker 2220, sensor 2230, camera 2240, motor controller/driver 2250, and motor 2260. In some embodiments, sensor 2230 can comprise one or more proximity sensors. In other embodiments, sensor 2230 can configured to use infrared (or near infrared) sources and/or ultrasonic sources. According to one aspect of the embodiments, sensor 2230 can be attached to main device 2100 (2100a, 2100b, 2100c) to provide information relating to the location of main device 2100 (2100a, 2100b, 2100c) relative to the eyes of a patient being examined.

In some embodiments, sensor 2230 can be configured to be detached from main device 2100 (2100a, 2100b, 2100c), and positioned at a fixed location, wherein the relative positions of main device 2100 (2100a, 2100b, 2100c) and sensor 2230 are known and/or the information of the relative positions can be calibrated.

According to another aspect of the embodiments, camera 2240 can be configured to capture video (or videos) of an external part of a patient's eye (including but not limited to the patient's retina). In many of the embodiments, camera 2240 can comprise either a single camera or a plurality of cameras. In addition, in some embodiments, camera 2240 can be configured to use infrared (or near infrared) illumination systems. In other embodiments, camera 2240 can be configured to have a higher image resolution than cameras of eye tracker 2220. Camera 2240 can be attached to main device 2100 (2100a, 2100b, 2100c) to provide the information relating to the location of main device 2100 (2100a, 2100b, 2100c) relative to the eyes of the patient being examined.

In some embodiments, camera 2240 can be configured to be detached from main device 2100 (2100a, 2100b, 2100c), and positioned at a fixed location, where the relative positions of main device 2100 (2100a, 2100b, 2100c) and camera 2240 are known and/or the information of the relative positions can be calibrated.

According to one aspect of the embodiments, computing/embedded system 2210 of robotic system 2200 can comprise one or more processors coupled to non-transitory memory, wherein the non-transitory memory is configured to store software instructions that, when executed by the one or more processors, cause the one or more processors to control robotic system 2200. In particular, the software instructions stored in non-transitory memory of the computing/embedded system 2210, when executed by the one or more processors, can cause the one or more processors to: receive data and/or images/videos from eye tracker 2220, sensor 2230, and/or camera 2240; determine one or more trajectories for motor 2260 by analyzing the received images/videos and/or data, wherein the one or more trajectories are configured to cause motor 2260 to move main device (2100a, 2100b, or 2100c) to a correct alignment position; and transmit one or more commands of relating to the one or more trajectories to motor controller 2250.

Figure 6:
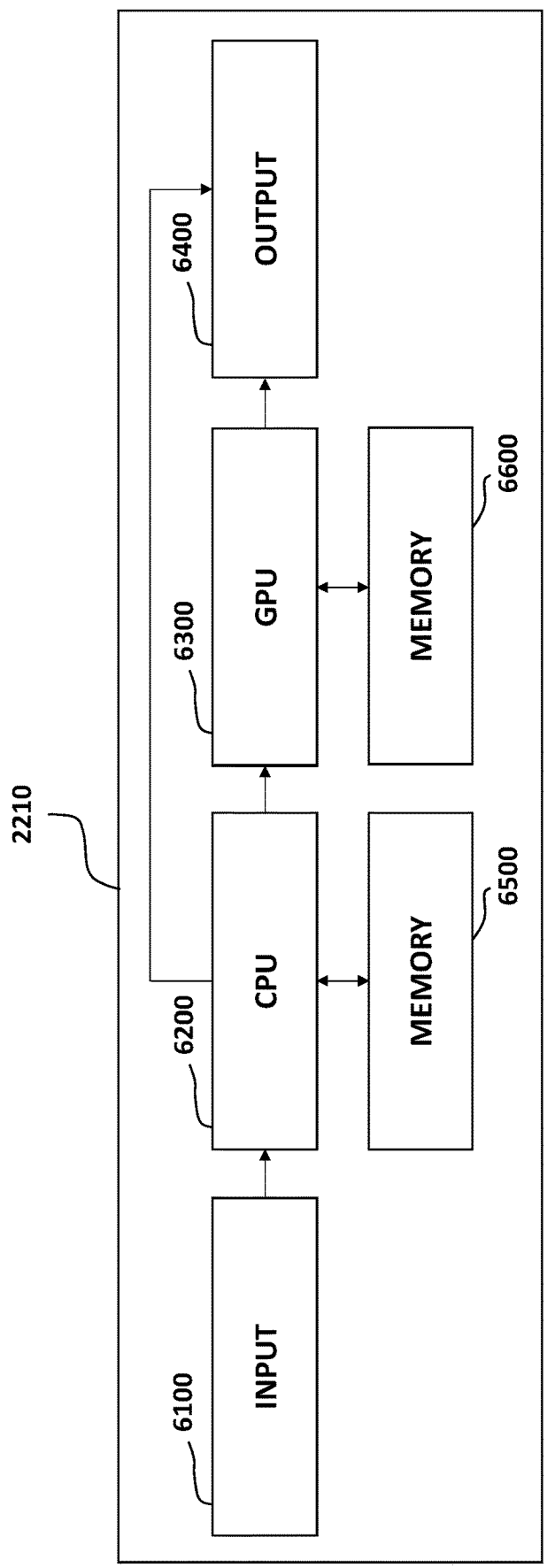
FIG. 6 is a block diagram illustrating an example embodiment of a computing/embedded system of an image and data gathering system.

FIG. 6 is a block diagram of an example embodiment of computing/embedded system 2210. Computing/embedded system 2210 can comprise input module 6100, one or more processors (e.g., central processing units ("CPUs") 6200, graphics processing units ("GPUs")) 6300, and one or more non-transitory memories of the CPU 6500, one or more non-transitory memories of the GPU 6600, and output module 6400.

Referring again to FIGS. 2A, 2B, and 2C, according to another aspect of the embodiments, eye tracker 2220 can comprise one or more infrared ("IR") and/or visible video cameras, IR and visible illumination components, one or more optical components (such as lenses). In addition, eye tracker 2220 can include its own computing/embedded system, comprising one or more computing processors coupled to non-transitory memory and one or more storage devices. The non-transitory memory and/or the one or more storage devices can be configured to store software instructions that, when executed by the one or more computing processors, cause the one or more computing processors to perform one or more of the following functions.

According to one aspect of the embodiments, for example, eye tracker 2220 can be configured to determine the location of a center of a patient's pupil and/or a size of the patient's pupil. In some embodiments, eye tracker 2220 can acquire the XYZ-coordinates of the pupil center of an eye being examined in real-time (e.g., sixty (60) frames per second or higher) for automated alignment of the robotic system 2200 for main device (2100a, 2100b, or 2100c). In other embodiments, eye tracker 2220 can also be configured to track the gaze of a patient to determine if the patient was looking at a specific target during an eye test (e.g., vision field test) and provide more accurate eye test results. In other embodiments, eye tracker 2220 can also be configured to track the gaze of a patient to determine if the patient was looking at a specific target (e.g. eye fixation) and determine when to capture retinal images (e.g., for automated image capture). In still other embodiments, eye tracker 2220 can be configured to provide cognitive tests and/or eye exercise programs, which can be performed by the patient to improve the health and/or condition of the patient's eye. Furthermore, in some embodiments, eye tracker 2220 can also be configured for use by a patient to communicate, for example, with a physician or staff with use of the eye.

Turning to FIGS. 7A to 7E, 8A to 8C, 9A to 9C, 10A to 10E, 11A to 11C, perspective views are provided of example embodiments of eye trackers in combination with main devices.

Figure 7B:
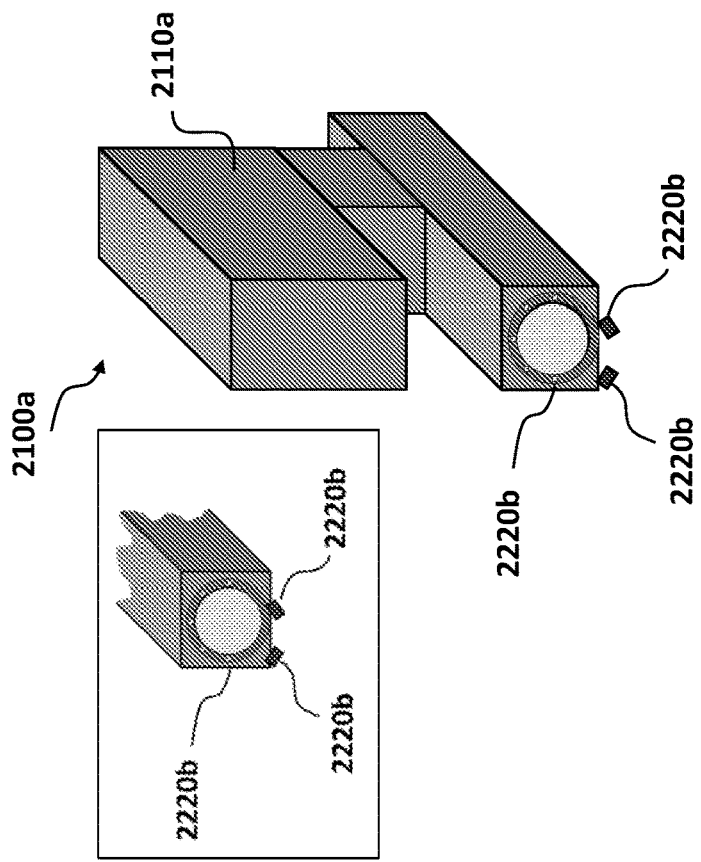
FIGS. 7A and 7B are perspective views of example embodiments of an eye tracker and a main device comprising a monocular imaging/sensing device.
Figure 7A:
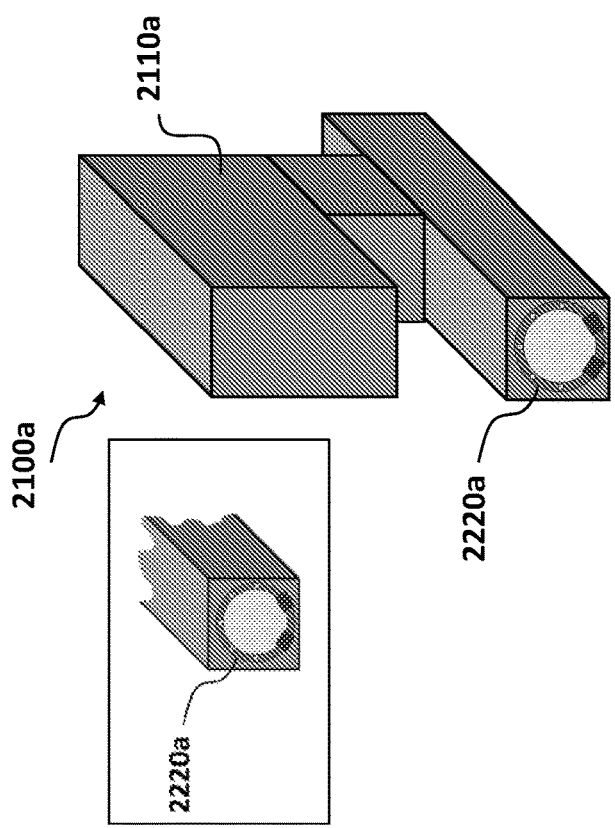

Referring first to FIG. 7A, a perspective view is shown of an example embodiment of a monocular main device 2100a, comprising an imaging/sensing device 2110a coupled to an eye tracker 2220a. According to some embodiments, a monocular component of eye tracker 2220a can be attached to a front portion near an objective lens of main device 2100a. According to one aspect of the embodiments shown in the insert in FIG. 7A, the depicted configuration can be implemented in a retinal imaging system. Referring to FIG. 10A, a perspective view is shown of an example embodiment of a monocular main device 2100c, similar to the embodiments described with respect to FIG. 7A, except that monocular main device 2100c further comprises a VR device 2120c, such as that described with respect to FIGS. 2B, 2C, 4, 5A, and 5B.

Turning to FIG. 7B, a perspective view is shown of another example embodiment of a monocular main device 2100a, comprising an imaging/sensing device 2110a coupled to an eye tracker 2220b. According to some embodiments, an illumination component of eye tracker 2220b can be attached to a front portion near an objective lens of main device 2100a. In some embodiments, eye tracker 2220b can comprise one or more cameras (e.g., two), that can be detached and positioned separately near one eye of the patient in a fixed location, where the relative positions of main device 2100a and eye tracker 2220b are known and can be used for calibration purposes. According to one aspect of the embodiments, as shown in the insert in FIG. 7B, the depicted configuration can be implemented in a retinal imaging system. Referring to FIG. 10B, a perspective view is shown of an example embodiment of a monocular main device 2100c, similar to the embodiments described with respect to FIG. 7B, except that monocular main device 2100c further comprises a VR device 2120c, such as that described with respect to FIGS. 2B, 2C, 4, 5A, and 5B.

Figure 7C:
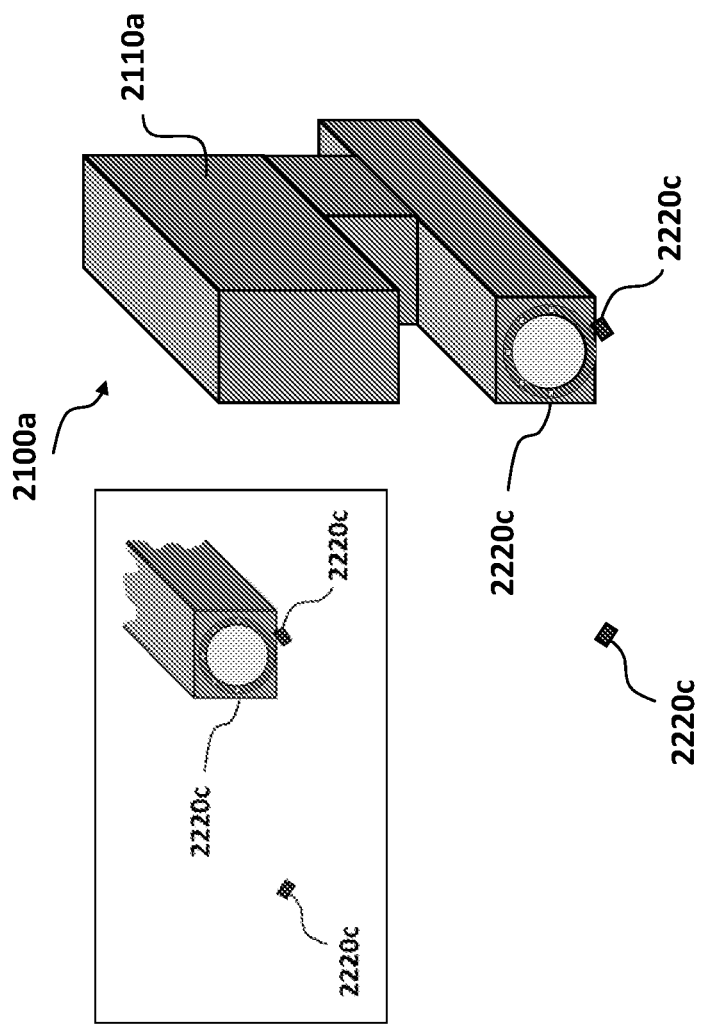
FIG. 7C is a perspective view of an example embodiment of an eye tracker and a main device comprising a monocular imaging/sensing device.
Figure 10C:
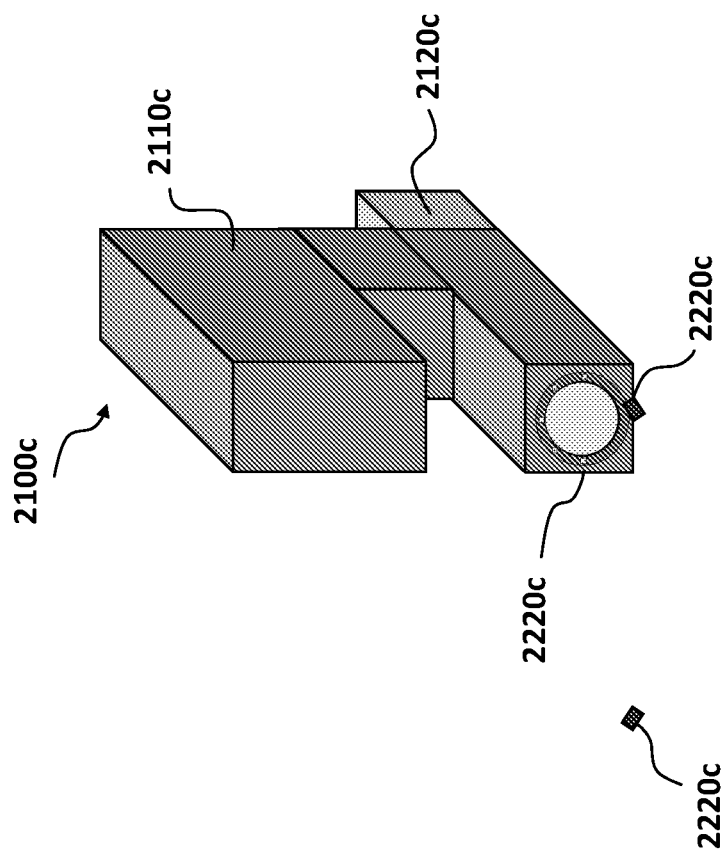
FIG. 10C is a perspective view of an example embodiment of an eye tracker and a main device comprising a monocular imaging/sensing device integrated with a VR device.
Figure 11A:
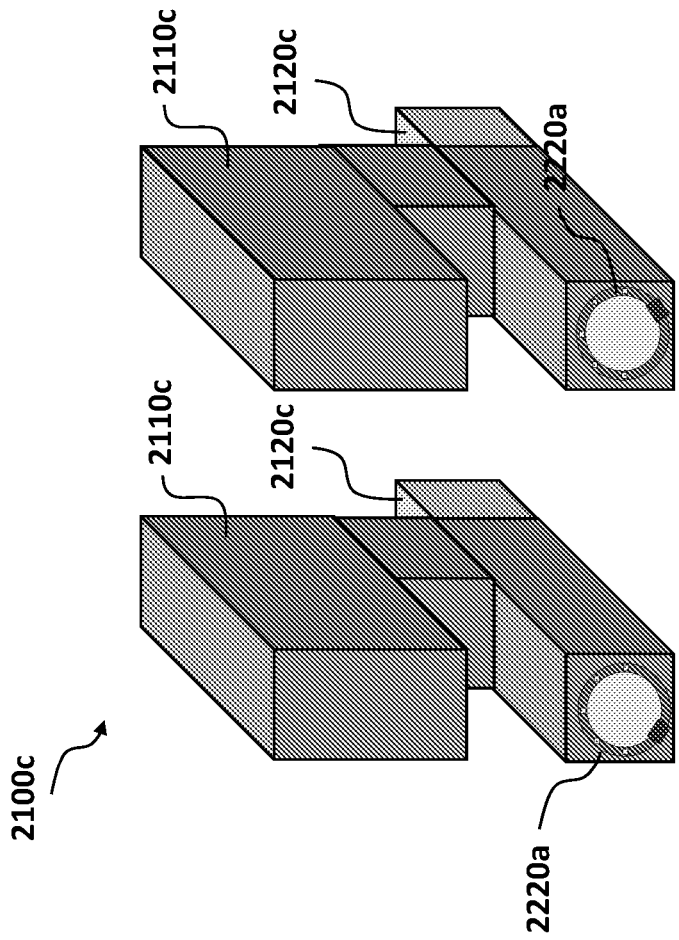
FIG. 11A is a perspective view of an example embodiment of a pair of eye trackers and main devices comprising a binocular imaging/sensing device integrated with a VR device.
Figure 11B:
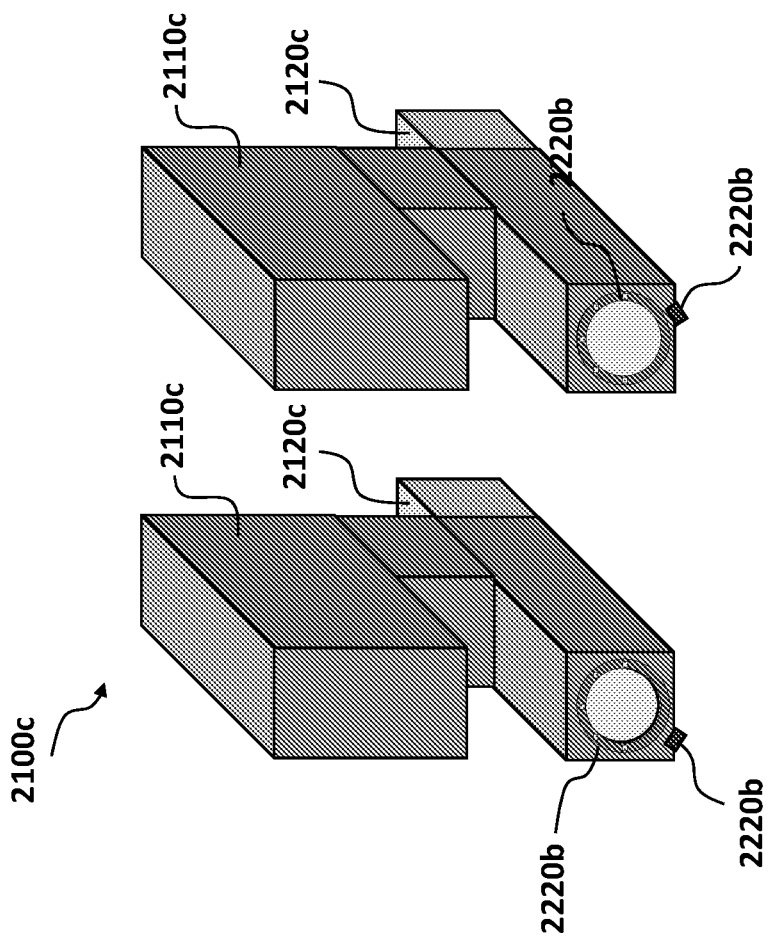
FIG. 11B is a perspective view of another example embodiment of a pair of eye trackers and main devices comprising a binocular imaging/sensing device integrated with a VR device.
Figure 11C:
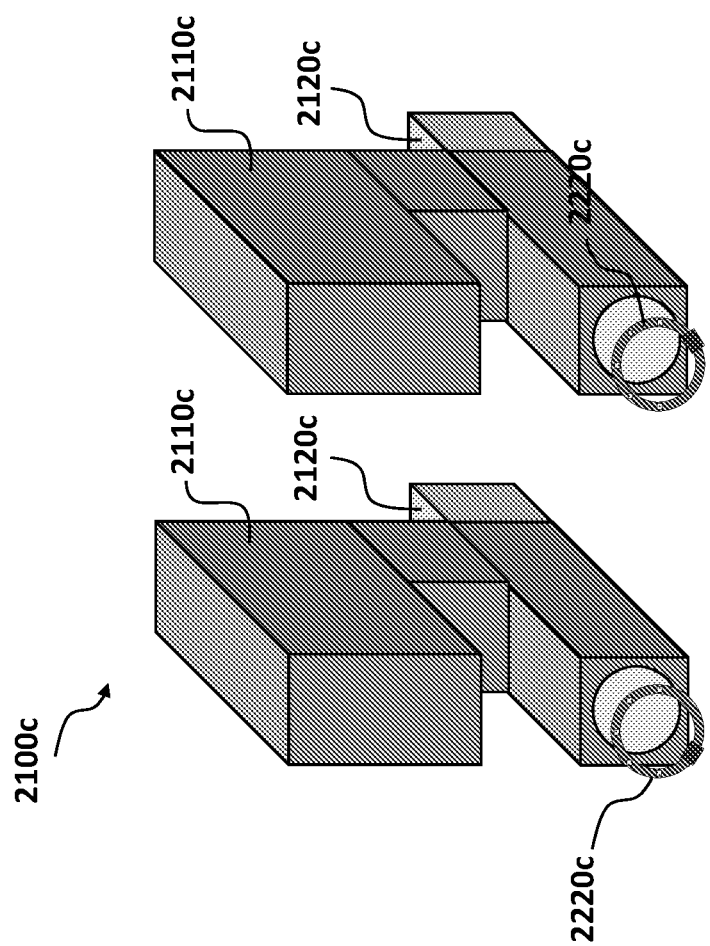
FIG. 11C is a perspective view of another example embodiment of a pair of eye trackers and main devices comprising a binocular imaging/sensing device integrated with a VR device.

Referring next to FIG. 7C, a perspective view is shown of another example embodiment of a monocular main device 2100a, comprising an imaging/sensing device 2110a coupled to an eye tracker 2220c. According to some embodiments, an illumination component of eye tracker 2220c can be attached to a front portion near an objective lens of main device 2100a. In some embodiments, eye tracker 2220c can include one or more cameras (e.g., two), each of which can be detached and positioned separately near each eye of the patient in fixed locations, where the relative positions of main device 2100a and eye tracker 2220c are known and can be used for calibration purposes. According to one aspect of the embodiments, as shown in the insert in FIG. 7C, the depicted configuration can be implemented in a retinal imaging system. Referring to FIG. 10C, a perspective view is shown of an example embodiment of a monocular main device 2100c, similar to the embodiments described with respect to FIG. 7C, except that monocular main device 2100c further comprises a VR device 2120c, such as that described with respect to FIGS. 2B, 2C, 4, 5A, and 5B.

Figure 7E:
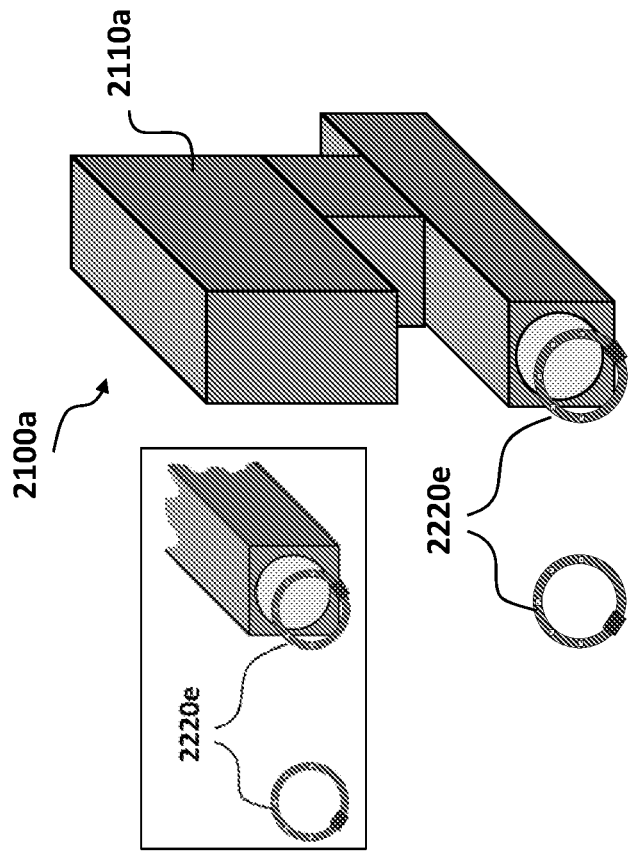
FIGS. 7D and 7E are perspective views of example embodiments of an eye tracker and a main device comprising a monocular imaging/sensing device.
Figure 7D:
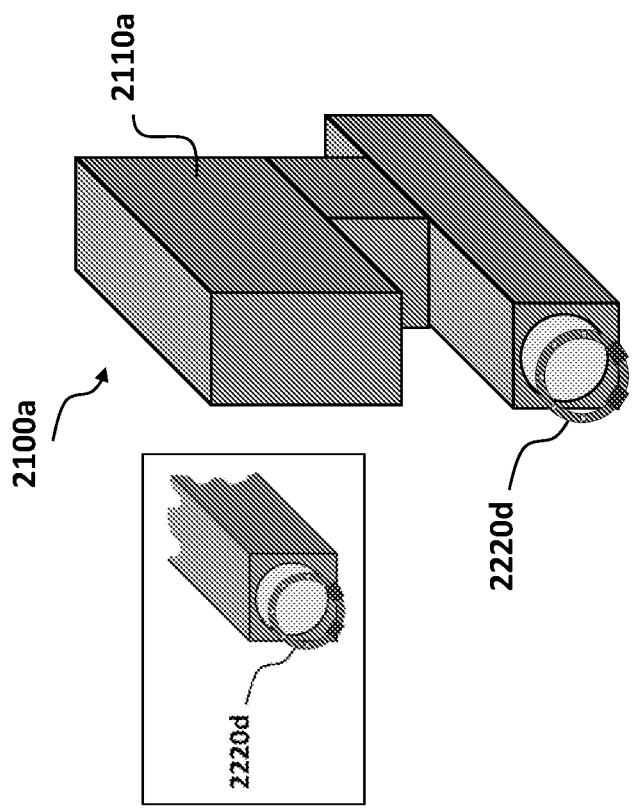

Turning to FIG. 7D, a perspective view is shown of another example embodiment of a monocular main device 2100a, comprising an imaging/sensing device 2110 coupled to an eye tracker 2220d. According to some embodiments, a monocular component of eye tracker 2220d can be detached from main device 2100a, and positioned separately near one eye of a patient in a fixed location, where the relative positions of main device 2100a and eye tracker 2220d are known and can be used for calibration purposes. According to one aspect of the embodiments, as shown in the insert in FIG. 7D, the depicted configuration can be implemented in a retinal imaging system. Referring to FIG. 10D, a perspective view is shown of an example embodiment of a monocular main device 2100c, similar to the embodiments described with respect to FIG. 7D, except that monocular main device 2100c further comprises a VR device 2120c, such as that described with respect to FIGS. 2B, 2C, 4, 5A, and 5B.

Referring to FIG. 7E, a perspective view is shown of another example embodiment of a monocular main device 2100a, comprising an imaging/sensing device 2110a coupled to an eye tracker 2220e. According to some embodiments, two components of eye tracker 2220e may be detached from the main device 2100a, which can be monocular, wherein the two components can be positioned separately near both eyes of the patient in fixed locations, where the relative position of the main device 2100a and eye tracker 2220e are known and can be used for calibration purposes. According to one aspect of the embodiments shown in the insert in FIG. 7E, the depicted configuration can be implemented in a retinal imaging system. Referring to FIG. 10E, a perspective view is shown of an example embodiment of a monocular main device 2100c, similar to the embodiments described with respect to FIG. 7E, except that monocular main device 2100c further comprises a VR device 2120c, such as that described with respect to FIGS. 2B, 2C, 4, 5A, and 5B.

Figure 8A:
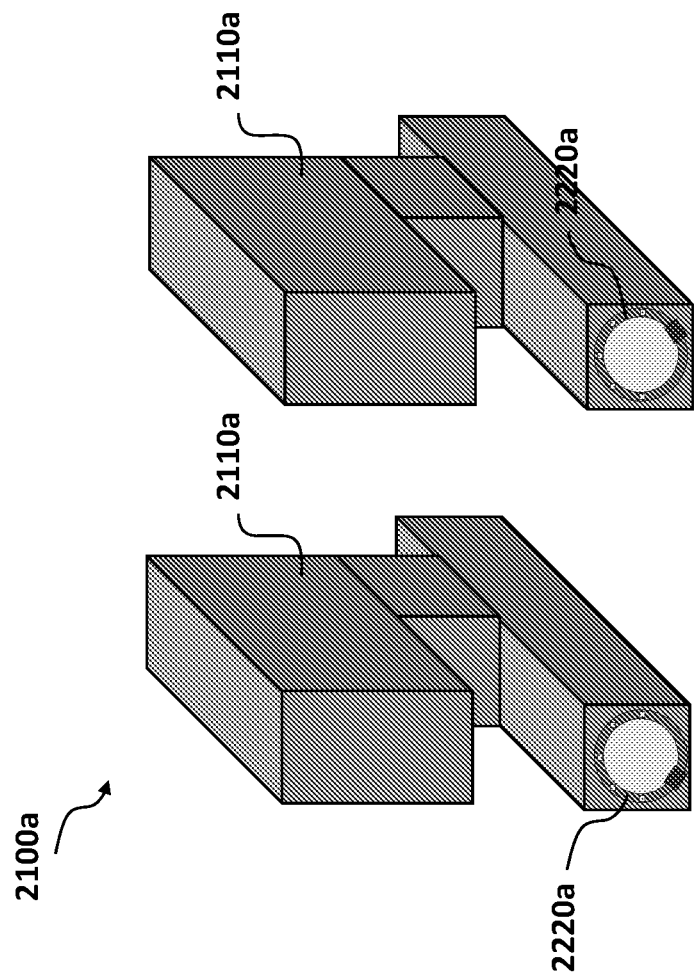
FIG. 8A is a perspective view of an example embodiment of a pair of eye trackers and main devices comprising a binocular imaging/sensing device.

Turning to FIG. 8A, a perspective view is shown of an example embodiment of a binocular main device 2100a, comprising a pair of imaging/sensing devices 2110a, each of which is coupled to each binocular component of eye tracker 2220a. According to some embodiments, each binocular component of the two eye trackers 2220a can be attached to a corresponding front portion near an objective lens of binocular main device 2100a. Referring to FIG. 9A, a perspective view is shown of an example embodiment of a binocular main device 2100b, similar to the embodiments described with respect to FIG. 8A, except that binocular main device 2100b comprises a VR device 2120b, such as that described with respect to FIGS. 2A, 2B, 3A, 3B, 4, 5A, and 5B. Similarly, referring to FIG. 11A, a perspective view is shown of an example embodiment of a binocular main device 2100c, similar to the embodiments described with respect to FIG. 8A, except that binocular main device 2100c further comprises a VR device 2120c, such as that described with respect to FIGS. 2B, 2C, 4, 5A, and 5B.

Figure 8B:
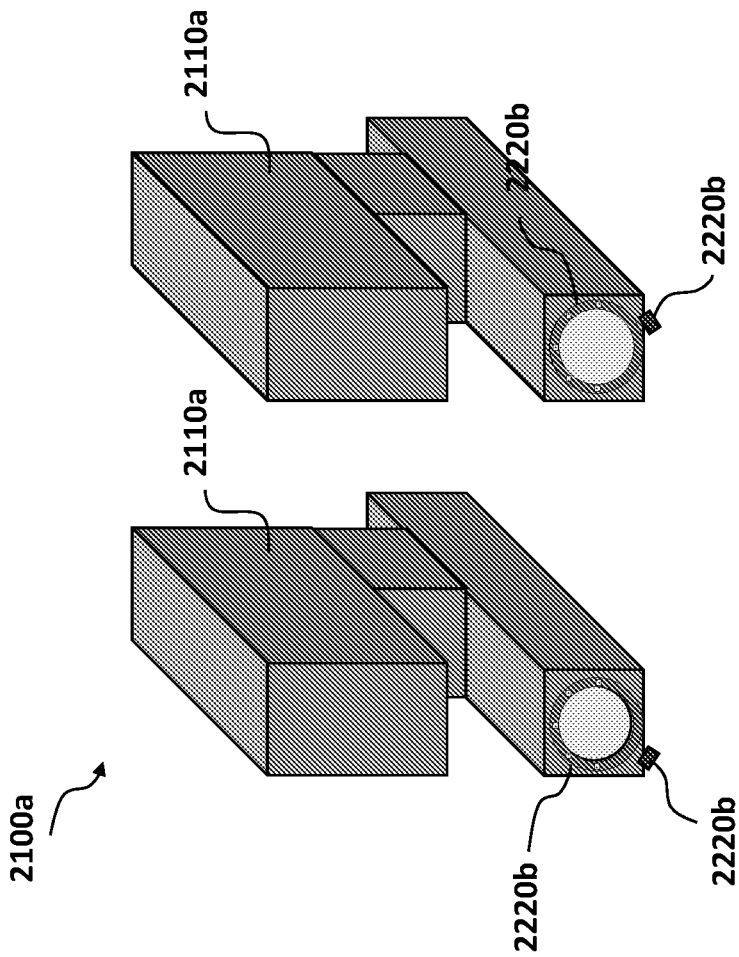
FIG. 8B is a perspective view of another example embodiment of a pair of eye trackers and main devices comprising a binocular imaging/sensing device.

Referring to FIG. 8B, a perspective view is shown of another example embodiment of a binocular main device 2100a, comprising a pair of imaging/sensing devices 2110a, each of which is coupled to each binocular component of eye tracker 2220b. According to some embodiments, each illumination component of eye tracker 2220b can be attached to a front portion near an objective lens of main device 2100a. In some embodiments, each binocular component of eye tracker 2220b can comprise a camera that can be detached and positioned separately near each eye of the patient in a fixed location, where the relative position of main device 2100a and each binocular component of eye tracker 2220b are known and can be used for calibration purposes. Referring to FIG. 9B, a perspective view is shown of an example embodiment of a binocular main device 2100b, similar to the embodiments described with respect to FIG. 8A, except that binocular main device 2100b further comprises a VR device 2120b, such as that described with respect to FIGS. 2A, 2B, 3A, 3B, 4, 5A, and 5B. Similarly, referring to FIG. 11B, a perspective view is shown of an example embodiment of a binocular main device 2100c, similar to the embodiments described with respect to FIG. 8A, except that binocular main device 2100c further comprises a VR device 2120c, such as that described with respect to FIGS. 2B, 2C, 4, 5A, and 5B.

Figure 8C:
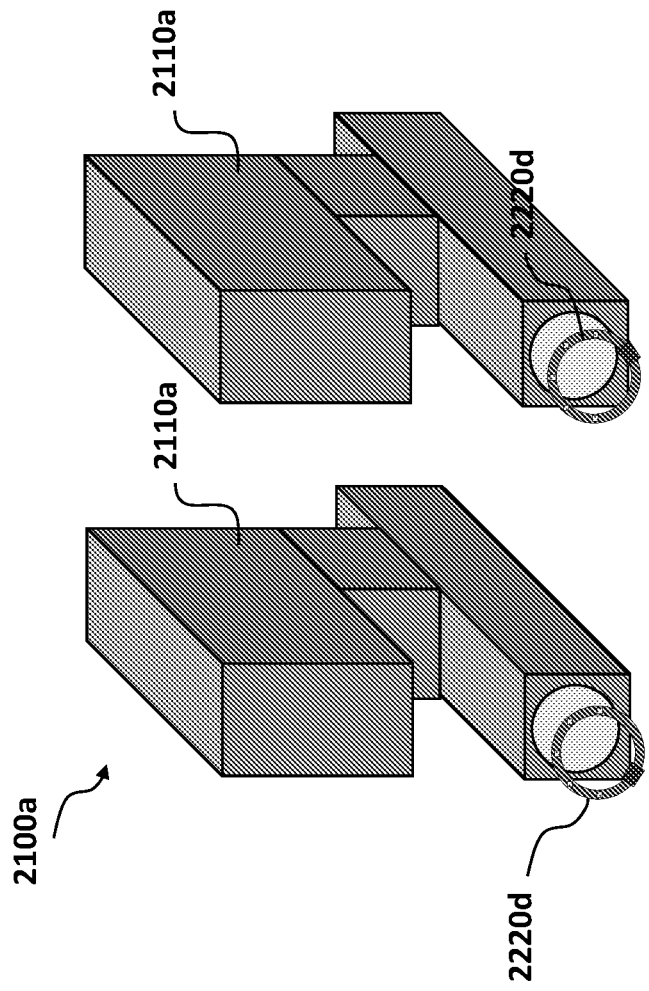
FIG. 8C is a perspective view of another example embodiment of a pair of eye trackers and main devices comprising a binocular imaging/sensing device.

Turning to FIG. 8C, a perspective view is shown of another example embodiment of a binocular main device 2100a, comprising a pair of imaging/sensing devices 2110a, each of which is coupled to each binocular component of eye tracker 2220d. According to some embodiments, each binocular component of eye trackers 2220d can be detached from main device 2100a, and positioned separately near one eye of the patient in a fixed location where the relative position of main device 2100a and each binocular component of eye tracker 2220d are known and can be used for calibration purposes. Referring to FIG. 9C, a perspective view is shown of an example embodiment of a binocular main device 2100b, similar to the embodiments described with respect to FIG. 8A, except that binocular main device 2100b comprises a VR device 2120b, such as that described with respect to FIGS. 2A, 2B, 3A, 3B, 4, 5A, and 5B. Similarly, referring to FIG. 11C, a perspective view is shown of an example embodiment of a binocular main device 2100c, similar to the embodiments described with respect to FIG. 8A, except that binocular main device 2100c further comprises a VR device 2120c, such as that described with respect to FIGS. 2B, 2C, 4, 5A, and 5B.

Example Embodiments of Methods for Screening, Diagnosis, and Monitoring

Example embodiments of methods for screening, diagnosis, and monitoring will now be described. As an initial matter, those of skill in the art will understand that the method steps disclosed herein can comprise software instructions stored in non-transitory memory of any of the computing devices or systems described herein, and that the instructions, when executed by one or more processors of the computing device or system, can cause the one or more processors to perform any or all of the method steps disclosed herein. Furthermore, those of skill in the art will appreciate that any or all of the method steps disclosed herein can be performed by either a single computing device or system, or, in the alternative, across various devices in geographically dispersed locations. For example, according to some embodiments, the method steps described herein can be performed, either entirely or in part, by a system for eye imaging, screening, diagnosis, and monitoring 1000, as described with respect to FIG. 1.

According to another aspect of the embodiments, the methods described herein can be used for the screening, monitoring, and/or diagnosis of various diseases and medical conditions, including, but not limited to, eye diseases/conditions (e.g., diabetic retinopathy, age-related macular degeneration, and glaucoma), neurodegenerative diseases and/or conditions (e.g., Alzheimer's disease), and systemic diseases and/or conditions (e.g., cardiovascular diseases).

Figure 12:
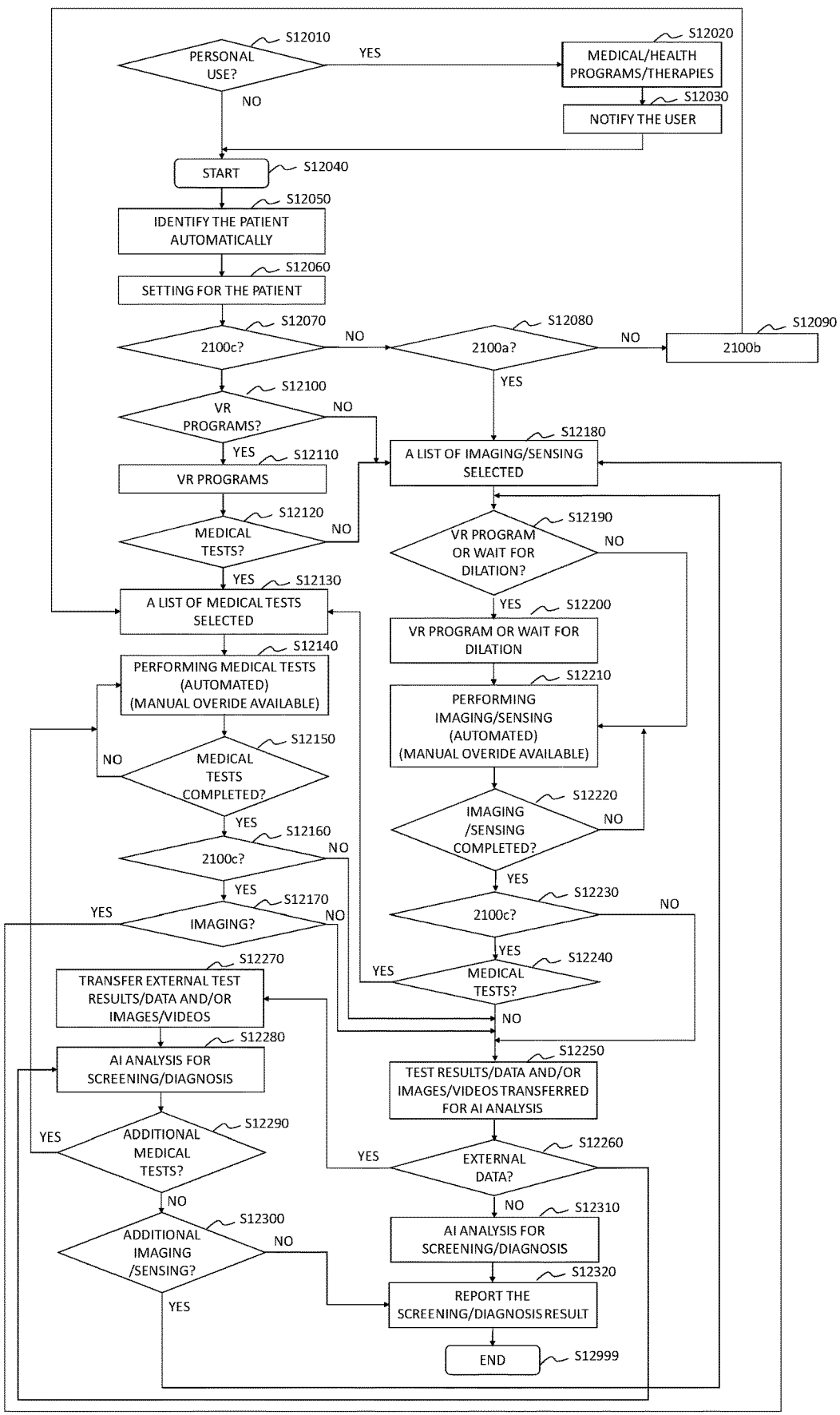
FIG. 12 is a flowchart illustrating an example embodiment of a method for eye screening, diagnosis, and monitoring.

FIG. 12 is a flowchart illustrating an example embodiment of a method for eye imaging, screening, diagnosis, and monitoring, wherein each of the method steps is described below along with a numbered code in parentheses (e.g., S12010, S12020, S12030) corresponding to a method step depicted in FIG. 12.

If the method for screening, diagnosis, and monitoring is for personal use (e.g., by a patient at home) (S12010), medical and health programs, as well as therapies, can be used as needed by the user (S12020). A managing and monitoring system 1200, such as that described with respect to FIG. 1, can notify a user that he or she needs to take one or more medical tests, such as by using a VR device (2110b), or needs to take screening such as by using an imaging and sensing device 2110 (2110a or 2110c), such as that described with respect to FIGS. 2A to 2C, and when it is time to do so (S12030). After the user is notified, the user can engage and start to use the system for eye imaging, screening, diagnosis, and monitoring 1000 (S12040). If system 1000 is configured for non-personal use (e.g., in a hospital/clinic setting), system 1000 can also be started by an individual other than a patient (e.g., physician, staff, technician of a hospital/clinic) (S12040).

According to another aspect of the embodiments, system for eye imaging, screening, diagnosis, and monitoring 1000 can then identify a patient automatically by acquiring and analyzing retinal images and/or video frames (or iris images and/or video frames) of the patient and, optionally, automatically retrieving the patient's information (S12050). In this regard, the embodiments described herein can prevent mistakes in identifying and recording information of a patient. In addition, settings for various medical tests and for imaging and/or sensing of a patient can be inputted and/or configured with the managing and monitoring device 1200 (S12060).

If system for eye imaging, screening, diagnosis, and monitoring 1000 comprises main device 2100c, including an imaging and sensing device 2110c and a VR device 2120c, such as that described with respect to FIG. 2C, (S12070, S12230) certain VR programs can be executed for a patient prior to conducting medical tests, imaging and/or sensing (S12100). For example, in some embodiments, VR programs can be configured to perform one or more tasks (S12110), such as: dilating a patient's eyes; instructing the patient regarding the process of screening, diagnosis, and monitoring; displaying educational information to the patient regarding the relevant medical matters or diseases; and/or comforting the patient. In other embodiments, if the patient is an infant or young child, VR programs can be configured to comfort and attract the attention of the patient.

Referring still to FIG. 12, if medical tests are chosen (S12120), a list of medical tests can be selected by a health care provider or by a computing system (e.g., computing/embedded system of robotic system 2200, computing/embedded system of the eye tracker 2220, or computing system of managing and monitoring device 1200), which can be configured to make a recommendation on the list of medical tests to be performed based on a patient's historical medical and/or health data (S12130). In many of the embodiments, the medical tests can then be run automatically by default (S12140). In some embodiments, a manual override feature can be provided, wherein the manual override feature is configured to perform or stop certain medical tests (S12140). In addition, according to some embodiments, upon completion of one or more medical tests (S12150), imaging and/or sensing tasks can then be performed (S12170).

According to another aspect of the embodiments, a list of imaging and/or sensing tasks can be selected by a health care provider or by a computing system (e.g., computing/embedded system of robotic system 2200, computing/embedded system of the eye tracker 2220, or computing system of managing and monitoring device 1200), which can be configured to make a recommendation on the list of imaging and/or sensing tasks based on the patient's medical history, medical data, and/or medical test results (S12280). In some embodiments, VR programs can be utilized for the patient prior to performing imaging, sensing, and/or eye tests. For example, as described earlier, VR programs can be configured to dilate a patient's eyes. In other embodiments, a patient can be instructed (e.g., by a VR program or by a physician or technician) to wait until his or her eyes, which can be covered, achieve a predetermined amount of natural dilation (S12200). The imaging and/or sensing tasks can then be run automatically by default (S12210). In some embodiments, a manual override feature can be provided, wherein the manual override feature is configured to perform or stop certain imaging and/or sensing tasks (S12210).

Upon completion of the medical tests (S12150, S12240) and/or the imaging and/or sensing tasks (S12220), results of the medical tests and/or the imaging and/or sensing tasks (e.g., images, sensor data) can be transferred (S12250) to a computing system for AI-based screening, diagnosis, and monitoring 1300, such as that described with respect to FIG. 1 (S12280). According to some embodiments, additional patient data and/or images/videos can also be imported from a data storage system 1400, such as that described with respect to FIG. 1, and transferred to the computing system for AI-based screening, diagnosis, and monitoring 1300 (S12260, S12270). In some embodiments, supplemental medical tests and/or imaging and/or sensing tasks can be further recommended by a health care provider or a computing system (e.g., computing/embedded system of robotic system 2200, computing/embedded system of the eye tracker 2220, or computing system of managing and monitoring device 1200), which can be configured to make a recommendation on a list of supplemental medical tests and/or imaging and/or sensing tasks based on AI analysis results from screening, diagnosis, and monitoring (S12290, S12300). According to another aspect of the embodiments, reports relating to the screening, diagnosis, and monitoring can then be visually displayed and shared (S12310). The method for eye imaging, screening, diagnosis, and monitoring can then terminate (S12999).

Referring still to FIG. 12, if system for eye imaging, screening, diagnosis, and monitoring 1000 comprises main device 2100*a*, including an imaging and sensing device 2110*a*, such as that described with respect to FIG. 2A, a list of imaging/sensing tasks can be selected by a health care provider or by a computing system (e.g., computing/embedded system of robotic system 2200, computing/embedded system of the eye tracker 2220, or computing system of managing and monitoring device 1200), which can be configured to make a recommendation on the list of imaging/sensing tasks to be performed based on a patient's historical medical and/or health data (S12180). A patient can wait until his or her eyes, which can be covered, achieve a predetermined amount of natural dilation (S12200). The imaging and/or sensing tasks can then be run automatically by default (S12210). In some embodiments, a manual override feature can be provided, wherein the manual override feature is configured to perform or stop certain imaging and/or sensing tasks (S12210).

Upon completion of the imaging and/or sensing tasks (S12220), results of the imaging and/or sensing tasks (e.g., images, sensor data) can be transferred to a computing system for AI-based screening, diagnosis, and monitoring 1300, such as that described with respect to FIG. 1 (S12250). According to some embodiments, additional patient data and/or images/videos can also be imported from a data storage system 1400, such as that described with respect to FIG. 1, and transferred to the computing system for AI-based screening, diagnosis, and monitoring 1300 (S12260). In some embodiments, supplemental imaging and/or sensing tasks can be further recommended by a health care provider or a computing system (e.g., computing/embedded system of robotic system 2200, computing/embedded system of the eye tracker 2220, or computing system of managing and monitoring device 1200), which can be configured to make a recommendation on a list of supplemental imaging and/or sensing tasks based on AI analysis results from screening, diagnosis, and monitoring (S12300). According to another aspect of the embodiments, reports relating to the screening, diagnosis, and monitoring can then be visually displayed and shared (S12320). The method for eye imaging, screening, diagnosis, and monitoring can then terminate (S12999).

Referring still to FIG. 12, if system for eye imaging, screening, diagnosis, and monitoring 1000 comprises main device 2100*b*, including a VR device 2120*b*, such as that described with respect to FIG. 2B, a list of medical tests can be selected by a health care provider or by a computing system (e.g., computing/embedded system of robotic system 2200, computing/embedded system of the eye tracker 2220, or computing system of managing and monitoring device 1200), which can be configured to make a recommendation on the list of medical tests to be performed based on a patient's historical medical and/or health data (S12130). In many of the embodiments, the medical tests can then be run automatically by default (S12140). In some embodiments, a manual override feature can be provided, wherein the manual override feature is configured to perform or stop certain medical tests (S12140).

Upon completion of the medical tests, results of the medical tests can be transferred to a computing system for AI-based screening, diagnosis, and monitoring 1300, such as that described with respect to FIG. 1. According to some embodiments, additional patient data and/or images/videos can also be imported from a data storage system 1400, such as that described with respect to FIG. 1, and transferred to the computing system for AI-based screening, diagnosis, and monitoring 1300 (S12250). In some embodiments, supplemental medical tests can be further recommended by a health care provider or a computing system (e.g., computing/embedded system of robotic system 2200, computing/embedded system of the eye tracker 2220, or computing system of managing and monitoring device 1200), which can be configured to make a recommendation on a list of supplemental medical tests based on AI analysis results from screening, diagnosis, and monitoring (S12290). According to another aspect of the embodiments, reports relating to the screening, diagnosis, and monitoring can then be visually displayed and shared (S12320). The method for eye imaging, screening, diagnosis, and monitoring can then terminate (S12999).

Example Embodiments of Configurations and Methods for Robotically Controlled Alignment Example embodiments of configurations and methods for robotically controlled and automatic alignment of main device 2100 (2100*a*, 2100*b*, or 2100*c*) by robotic system 2200, such as that described with respect to FIGS. 2A, 2B, and 2C, will now be described. As an initial matter, those of skill in the art will understand that the method steps disclosed herein can comprise software instructions stored in non-transitory memory of any of the computing devices or systems described herein, and that the instructions, when executed by one or more processors of the computing device or system, can cause the one or more processors to perform any or all of the method steps disclosed herein. Furthermore, those of skill in the art will appreciate that any or all of the method steps disclosed herein can be performed by either a single computing device or system, or, in the alternative, across various devices in geographically dispersed locations.

Before describing more particular aspects of the method embodiments in detail, however, it is first desirable to describe examples of configurations that can be used with robotic system 2200, as well as examples of their operation, all of which can be used with the embodiments described herein.

Figure 13A:
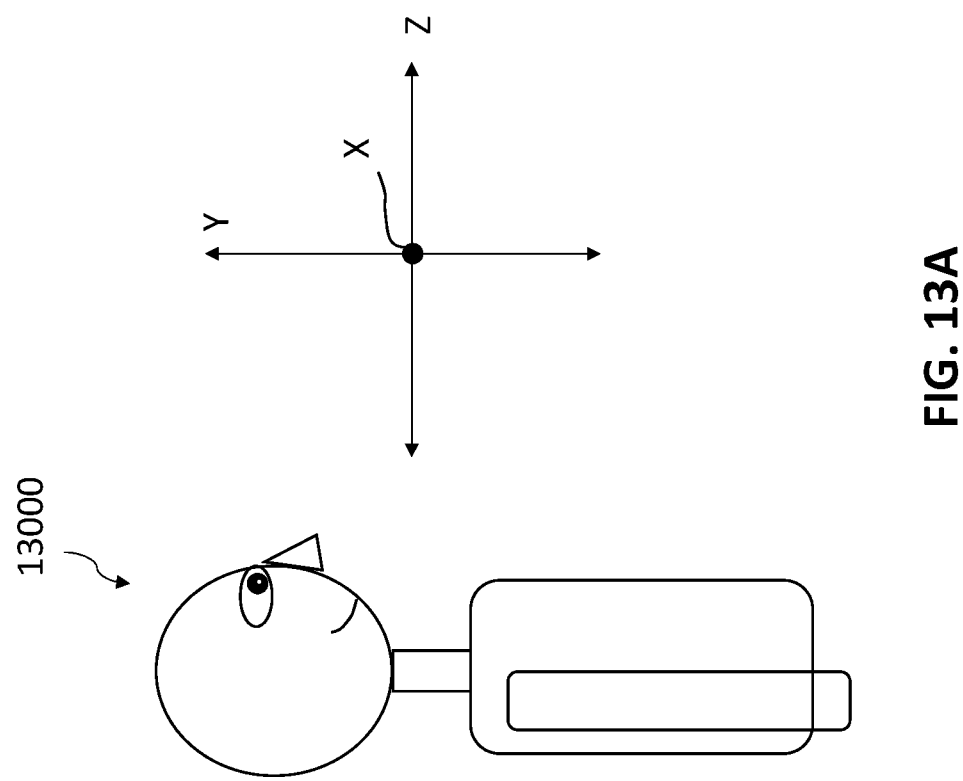
FIG. 13A is a diagram illustrating three axes of directions for a robotic system.

FIG. 13A is a diagram illustrating a directional reference for robotic system 2200 according to three axes: a forward-backward direction (Z-axis), a right-left direction (X-axis), and an up-down direction (Y-axis), each direction being relative to the position and orientation of patient 13000.

FIG. 13B is a diagram illustrating an example initial (default) position 13200i (X0, Y0, Z0) of main device 2100 (2100a, 2100b, 2100c). According to one aspect of the embodiments, position 13200i can be defined as the position of a center portion of a front surface of main device 2100 (e.g., a center portion of the front surface of the objective lens) from a predetermined origin. According to another aspect of the embodiments, the positions of a right eye 13100r and a left eye 13100l of a patient being examined are also shown.

Figure 13C:
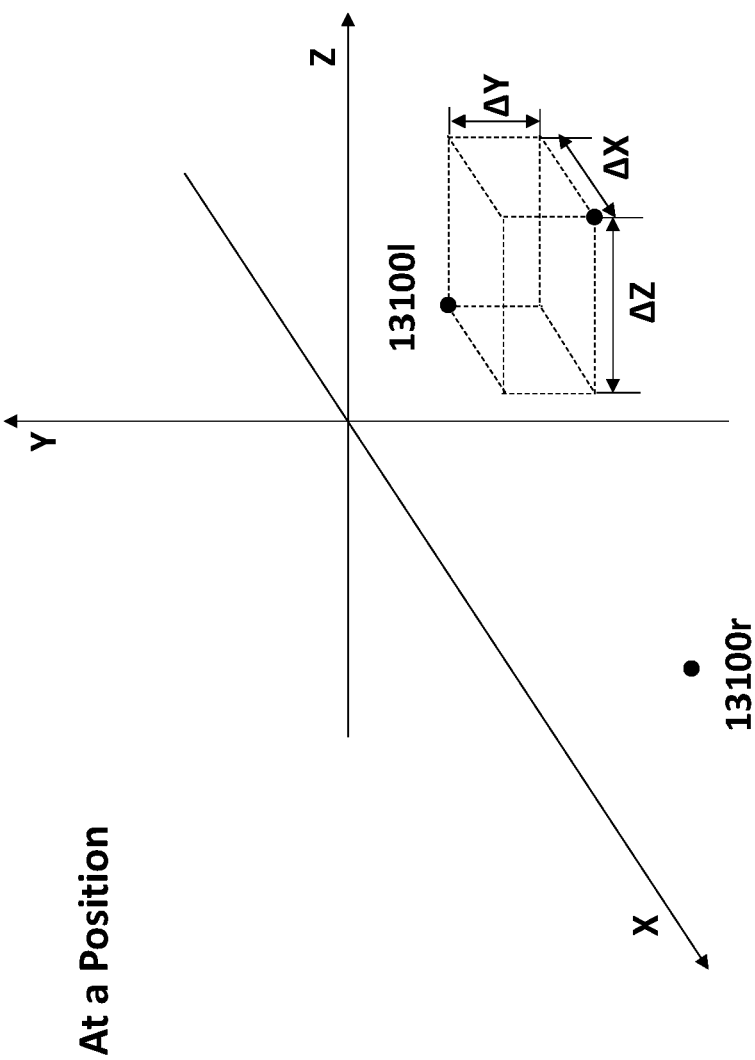
FIG. 13C is a diagram illustrating a position of a main device relative to a pupil center of a left eye.

FIG. 13C is a diagram illustrating a relative position ($\Delta X$, $\Delta Y$, $\Delta Z$) of main device 2100 (2100a, 2100b, 2100c) to a pupil center of an eye. According to one aspect of the embodiments, position ($\Delta X$, $\Delta Y$, $\Delta Z$) represents a displacement between a center portion of a front surface of main device 2100 and a pupil center of an eye (e.g., left eye 13100l) being examined.

Figure 13D:
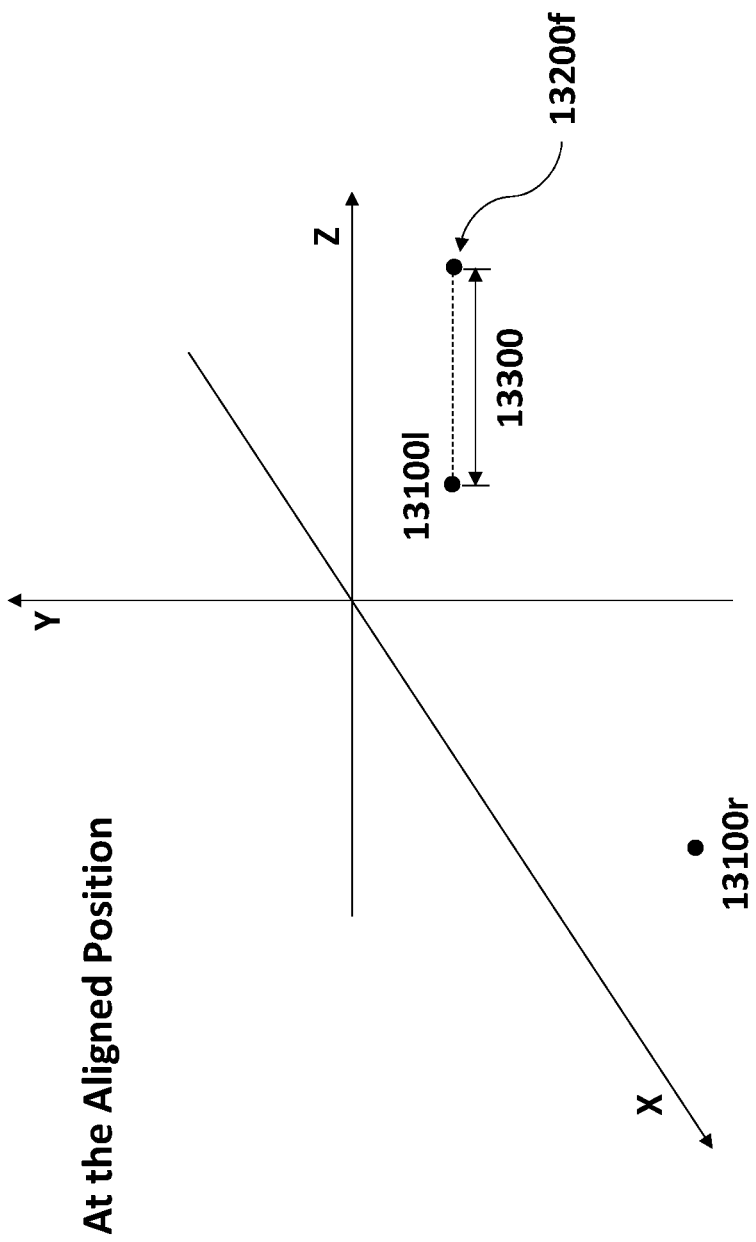
FIG. 13D is a diagram illustrating a final or aligned position of a main device relative to a pupil center of a left eye.

FIG. 13D is a diagram illustrating a re-positioning of main device 2100 (2100a, 2100b, 2100c) to a final or aligned position 13200f. According to one aspect of the embodiments, main device 2100 (2100a, 2100b, 2100c) can be configured to move to position 13200f, which can comprise an alignment position where ($\Delta X$, $\Delta Y$, $\Delta Z$)=(0, 0, working distance 13300 of main device 2100), and wherein at position 13200f, high quality images/data of a patient's eye can be acquired.

According to one aspect of the embodiments, robotic system 2200 can be configured to receive and utilize data indicative of a location of a pupil center of an eye, wherein the data can be provided in real-time (e.g., 60 frames per second or higher) by an eye tracker 2220. In many of the embodiments, eye tracker 2220 can be attached to main device 2100 (2100a, 2100b, 2100c), and configured to send information to robotic system 2200, wherein the information includes data indicative of a location of a center of an eye pupil relative to a position (e.g., position of cameras of eye tracker) which can be converted to the location of main device 2100 relative to a center of an eye pupil. Additionally, in some embodiments, data from sensor 2230 and/or motor encoder values from motor controller 2250 can also provide additional location information (e.g., coordinates indicative of $\Delta X$, $\Delta Y$, and/or $\Delta Z$).

According to other embodiments, eye tracker 2220 can be configured to be detached from main device 2100 (2100a, 2100b, 2100c), and positioned near the eyes of a patient at a fixed location, where the relative position of main device 2100 and eye tracker 2220 are known and/or the information of said relative position can be calibrated. Additionally, in some embodiments, data from sensor 2230 and/or motor encoder values from motor controller 2250 can also provide additional location information (e.g., coordinates indicative of $\Delta X$, $\Delta Y$, and/or $\Delta Z$).

According to still other embodiments, robotic system 2200 can be configured to utilize a camera 2240 in addition to eye tracker 2220, to acquire information indicative of the position of main device 2100 relative to a center of an eye pupil. In some embodiments, for example, camera 2240 can have a higher resolution than the cameras of eye tracker 2220. According to some embodiments, camera 2240 can be configured to capture video using one or more IR (or near IR) illumination systems and one or more IR (or near IR) image sensors. According to one aspect of the embodiments, robotic system 2200 can then be configured to analyze video frames of the external parts of an eye and/or retina of a patient captured by camera 2240. In this regard, camera 2240 can be configured to provide accurate information indicative of a position of a pupil of an eye by using higher image resolution images which can be converted to the location of main device 2100 relative to a center of an eye pupil. Additionally, in some embodiments, data from sensor 2230 and/or motor encoder values from motor controller 2250 can also provide additional location information (e.g., coordinates indicative of $\Delta X$, $\Delta Y$, and/or $\Delta Z$).

In still other embodiments, robotic system 2200 can be configured to analyze video frames of external parts of an eye and retina, captured by camera 2240, to acquire information indicative of a position of main device 2100 relative to a center of an eye pupil, without the use of eye tracker 2220. According to some embodiments, camera 2240 can be configured to capture video using one or more IR (or near IR) illumination systems and one or more IR (or near IR) image sensors. Additionally, in some embodiments, data from sensor 2230 and/or motor encoder values from motor controller 2250 can also provide additional location information (e.g., coordinates indicative of $\Delta X$, $\Delta Y$, and/or $\Delta Z$). According to another aspect of the embodiments, the analysis of the video frames for robot control can be performed by one or more of an eye tracking/centering module, a pupil tracking/centering module, a working distance module, a retinal FOV/coverage assessment module, an area-of-interest ("AOI") assessment module, and/or an image quality assessment module. Those of skill in the art will recognize that these modules can also by implemented with any of the previously described embodiments to control robotic system 2200.

Example embodiments of methods for analyzing video frames for robot control will now be described. As an initial matter, those of skill in the art will understand that the method steps disclosed herein can comprise software instructions stored in non-transitory memory of any of the computing devices or systems described herein, and that the instructions, when executed by one or more processors of the computing device or system, can cause the one or more processors to perform any or all of the method steps disclosed herein. Furthermore, those of skill in the art will appreciate that any or all of the method steps disclosed herein can be performed by either a single computing device or system, or, in the alternative, across various devices in geographically dispersed locations.

Figure 14:
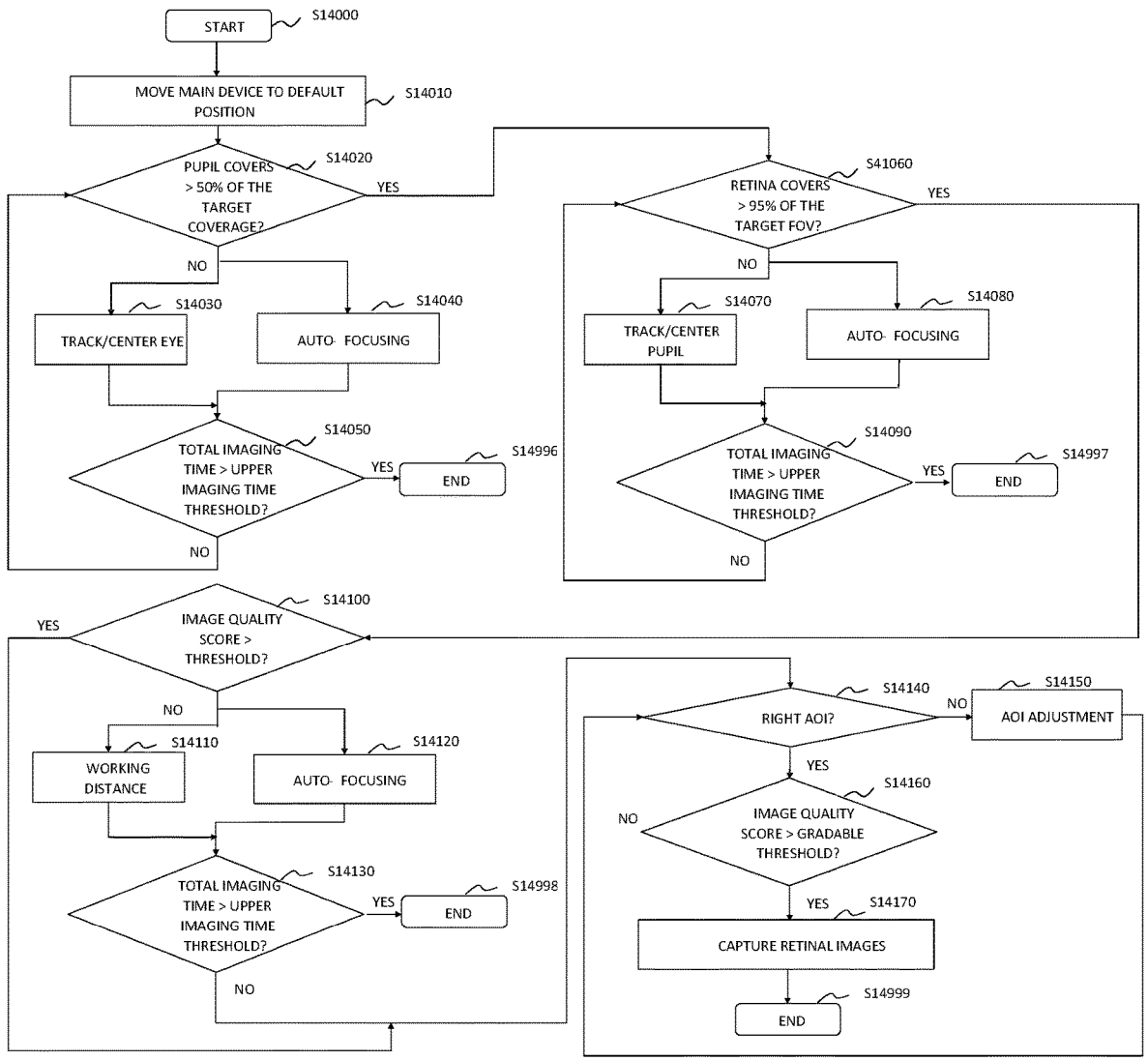
FIG. 14 is a flowchart illustrating an example embodiment of a method for robot control with video analysis.

FIG. 14 is a flowchart illustrating an example embodiment of a method for automated alignment with analyzing video frames of eye, wherein each of the method steps is described below along with a numbered code in parentheses (e.g., S14010, S14020, S14030) corresponding to a method step depicted in FIG. 14.

When the automated alignment starts (S14000), the main device may be moved to a default position by the motor 2260 of a robotic system 2200 (S14010). If the coverage of eye pupil being observed is less than the target coverage (e.g., 50%) (S14020), an eye tracking/centering module can be configured to approximately center the eye being examined (S14030). For example, the eye tracking/centering module can be configured to position main device 2100 (2100a, 2100b, 2100c) from a default position to a position near a center of an eye being examined, where position of ($\Delta X$, $\Delta Y$)=(0, 0) and Z can stay as a default position Z0 (e.g., approximate alignment).

Referring to the step S14030, according to one aspect of the embodiments, one or more eye landmarking and localization algorithms of an eye tracking/centering module can be configured to identify one or more salient features of an eye (e.g., corners of eye(s), eyebrow endpoints, etc.). Unlike some face landmarking algorithms that detect a subject's eyes, nose, and mouth from faces varying in pose, expression, and illumination, the embodiments of the present disclosure can include one or more of the following constraints for robot control: (i) a patient's eye is within a known region, and (ii) a significant portion of a facial region may not be visible because main device 2100 (2100a, 2100b, 2100c) may be close to the patient's eye (e.g., where main device 2100 comprises a wearable/head-mount).

Referring still to step S14030 (which can also be related to S14070), in many of the embodiments, eye and pupil landmarking and localization deep learning networks can be trained using transfer learning on image crops around a subject's eyes and pupils obtained from images from an annotated dataset. The data can be augmented using image transformations, such as gamma variation and noise addition, to make the network robust to low contrast stemming from IR (or near IR) illuminations. These algorithms can be configured to run on sliding window patches of the video frames around the estimated eye location or the estimated pupil location. The location of the eye or pupil determined by the landmarking algorithms can be configured to initialize an eye tracking module.

Still referring to the step S14030 (which can also be related to S14070), according to one aspect of the embodiments, a multi-level tracking-learning-detection ("TLD") tracker (also referred to herein as a tracking algorithm) can be utilized, wherein the TLD tracker can be configured to incorporate landmark information from the previous step. According to another aspect of the embodiment, the tracking algorithm can be capable of handling blinks (e.g., temporal interruptions) and small motions. In the case of larger motions of a patient, the tracking algorithm can be configured to fail and cause robotic system 2200 to reset. To expedite the reset process, a backtracking procedure can be utilized, wherein the robotic system 2200 can be configured to attempt to re-recognize an eye, while camera 2240 can be being moved away from the patient eye. To improve the performance and robustness of robotic system 2200, sensors 2230 and motor encoder values from motor controller 2250 can also be configured to supplement location information, correlate physical distances, and ground robotic system 2200.

An auto-focusing module can be configured to focus main device 2100 (2100a, 2100b, 2100c) while the robotic system tracks and/or centers the eye being examined (S14040).

If the total imaging process time (duration) to this point from the start of the automated alignment exceeds the upper imaging time threshold (S41050), the process may be configured to stop (S14996) and start from the beginning again, if needed (S14000). According to another aspect of the embodiments, at any point during the alignment and imaging process, if the duration to the point exceeds the upper imaging time threshold, the process may be configured to stop and start from the beginning again, if needed (S14000).

If the target pupil coverage is obtained (S14020) and the retina FOV is less than the target FOV (e.g., 95%) (S41060), a pupil tracking/centering module can be configured to center a pupil of the eye being examined (S14070). For example, the pupil tracking/centering module can be configured to position main device 2100 (2100a, 2100b, 2100c) to a position that is the center of a pupil of an eye being examined, where the position of ($\Delta X$, $\Delta Y$)=(0, 0) and Z can stay as a default position Z0 (e.g., fine alignment).

Referring to the step S14070, according to one aspect of the embodiments, pupil landmarking and localization algorithms of pupil tracking/centering module can be configured to identify a pupil of an eye and a center of an eye pupil. Corneal reflection/glint for improved learning and detection may be used additionally.

An auto-focusing module can also be configured to focus main device while the robotic system tracks and/or centers the eye pupil being examined (S14080).

If the image quality score is lower than a target threshold (S14100), a working distance module can be configured to position main device 2100 (2100a, 2100b, 2100c) from a default position of Z0 to a position where $\Delta Z$=working distance of the main device 2100 (2100a, 2100b, 2100c) (S14110). In one aspect of the embodiments, for example, main device 2100 (2100a, 2100b, 2100c) can be configured to be moved in a small increment in the Z direction in order to determine a position of a correct working distance, while keeping main device 2100 (2100a, 2100b, 2100c) at a center of an eye pupil with a pupil tracking/centering module.

Referring to step S14100, according to another aspect of the embodiments, an image quality assessment module can be configured to evaluate video frames to be captured and to save good quality images at an appropriate time instance when main device 2100 (2100a, 2100b, 2100c) is correctly aligned. In some embodiments, a CNN can be trained and configured to assess the quality of the video frames/images using transfer learning (e.g., from an image quality assessment CNN trained on a quantity of retinal images). Furthermore, according to some embodiments, the CNN can be configured to output a score relative to a gradable threshold to determine when to automatically capture a color retinal image (S14210).

An auto-focusing module can also be configured to focus main device while the robotic system tracks and/or centers the eye being examined (S14120).

If the image quality score is higher than the threshold (S14100), the correct AOI is obtained (S14140), and the image quality score is higher than the gradable threshold (S14160), retinal image can be captured automatically as default or can be captured manually if needed (S14170).

Referring to step S14140, according to one aspect of the embodiments, existing algorithms may be used to detect an optic nerve head ("ONH") and macula in conjunction with convolutional neural network ("CNN") classifiers to identify retinal fields (e.g., macula-centered, ONH-centered, etc.) and determine if intended retinal AOIs (e.g., an area within the vascular arcades for diabetic retinopathy and macula for age-related macular degeneration) can be captured in the retinal videos/images.

Referring to step S14160 (which can also be related to S14100) to ensure that retinal AOIs can be captured at gradable quality, a classifier can be developed using features derived from an image quality CNN. In some embodiments, for example, CNN can result in a quantity of activation maps of various sizes obtained from convolutional and max-pool layers. In some embodiments, a feature vector can be constructed for an image patch by choosing values from each of the activation maps at an appropriate location that corresponds to the desired image patch. In addition, according to some embodiments, a fully-connected neural network ("FCN") can be configured to provide gradable and/or ungradable labels on image patches. For example, in some embodiments, an FCN can be configured to utilize a training dataset comprising retrospective images with annotations of gradable/ungradable image patches, wherein the annotations can be prepared by experts. According to another aspect of some embodiments, image quality scores from the patches near or covering retinal AOIs can be aggregated to provide an overall determination of whether the retinal AOIs have been captured at gradable quality.

According to one aspect of the embodiments, spectrum (e.g., color temperature) and intensity of illumination for retinal image captures can be determined and controlled by AI algorithms based on a patient's data (e.g., race, age) and/or the IR (or near IR) video of the retina (S14170).

According to another aspect of the embodiments, the captured retinal images can be assessed again by a retinal FOV/coverage assessment module, AOI assessment module, and/or an image quality assessment module. Subsequently, if the captured images do not meet predetermined thresholds, robotic system 2200 can be configured to align, focus, and/or capture images again.

Example Embodiments of Systems for Retinal Imaging

Example embodiments of systems for retinal imaging, and their various componentry, will now be described. Before describing more particular aspects of these embodiments in detail, however, it is first desirable to describe examples of optical design pupil layouts and configurations that can be used with systems for retinal imaging, as well as examples of their operation.

Figure 15A:
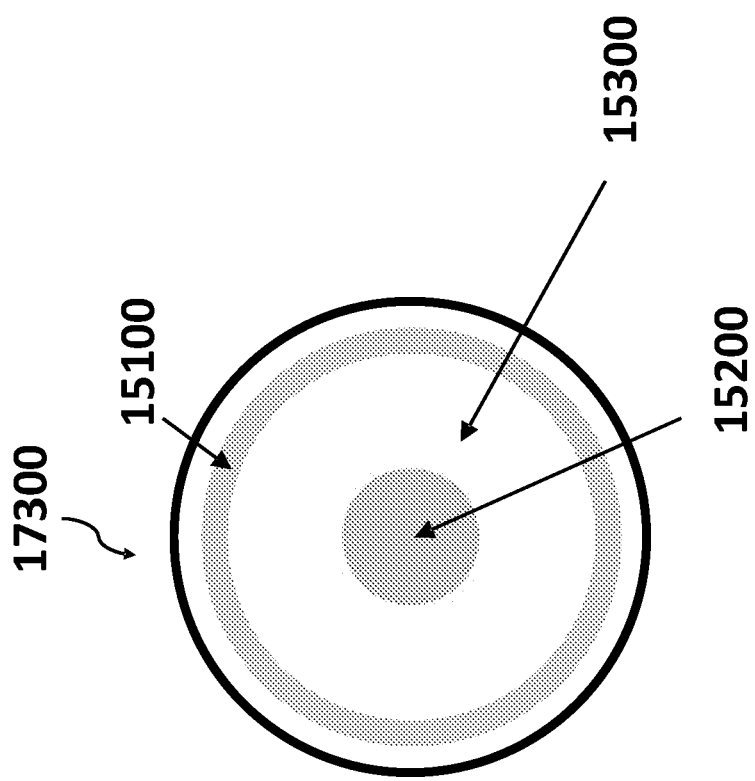

FIGS. 15A and 15B are diagrams of an optical design pupil layout for a system for retinal imaging using a known method for annular illumination. In particular, an annular illumination component 15100 at or near an eye pupil plane 17300 of an eye 17100 enables retinal imaging by leaving an area 15200 in a center portion of an eye pupil for imaging rays 15400 to pass through an optical system and reach an image sensor after reflection from the retina of an eye, while the retina is illuminated at the same time through the outer part of an eye pupil from the illumination source. A buffer area 15300 between the image of illumination and the area allocated to imaging rays can be configured to be wide enough to prevent the reflections from cornea in the retinal images.

FIGS. 16A to 16F are diagrams of various example embodiments of optical design pupil layouts of systems for retinal imaging of the present disclosure.

FIG. 16A is a diagram illustrating an example embodiment of an optical design pupil layout 17300a on/near pupil 17300 (shown in FIGS. 17 and 18A to 18C) of an eye that can be used for plurality of optical configurations of a system for retinal imaging (17000, 18000a, 18000b, 18000c, 27000, 28000a, 28000b, and 28000c shown in FIGS. 17 and 18A to 18C). According to one aspect of the embodiments, system for retinal imaging (17000, 18000a, 18000b, 18000c, 27000, 28000a, 28000b, or 28000c) can be configured to image the baffle-and-illumination module on or near a pupil plane 17300 of an eye. Pupil boundary 16100 of an eye is the conjugate to the aperture stop of the system of the retinal imaging (17000, 18000a, 18000b, 18000c, 27000, 28000a, 28000b, or 28000c).

Figure 19A:
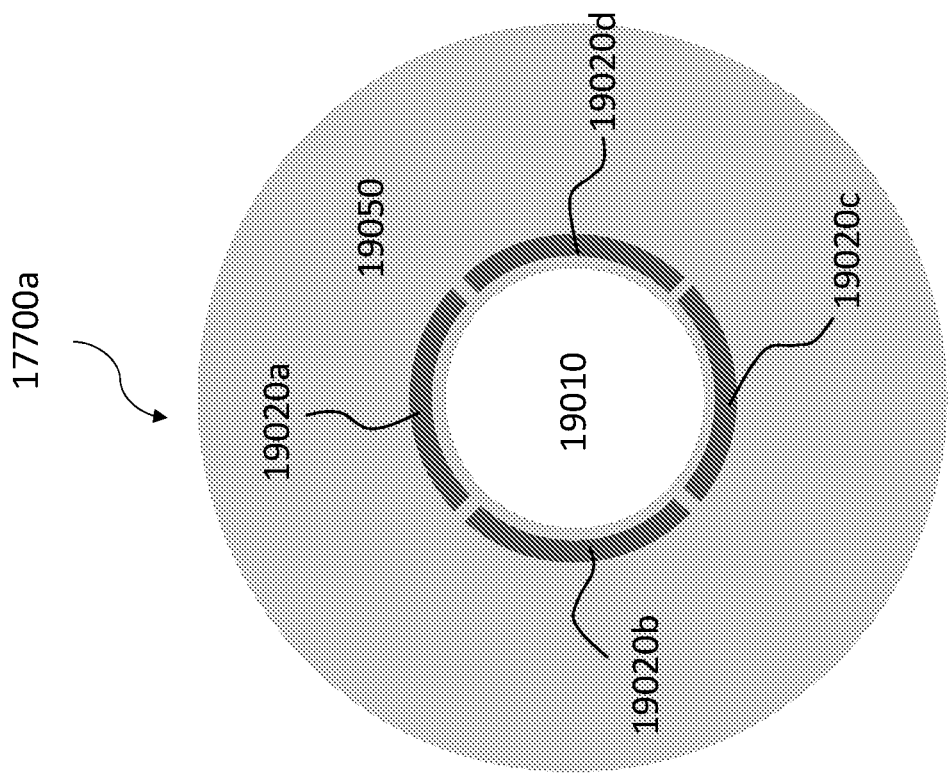
FIGS. 19A to 19F are diagrams of example embodiments of a single baffle-and-illumination module.

According to another aspect of optical design pupil layout 17300a, four narrow areas 16200a, 16200b, 16200c, and 16200d (at or near the pupil plane 17300 of an eye) can be allocated for four separate illumination patches from illumination sub-systems 19020a, 19020b, 19020c, and 19020d (as shown in FIG. 19A) to illuminate a retina, and an area in a middle portion 16400a (at or near the pupil 17300 of eye) can be configured for imaging rays to pass through toward a baffle-and-illumination module from the retina of an eye. As can be seen in FIG. 16A, in some embodiments, only the upper illumination sub-system 19020a (as shown in FIG. 19A) can be active and the other illumination sub-systems can be inactive. According to an aspect of the embodiments, four images from different parts of a retina can be acquired by using each of the four illumination sub-systems.

Figure 16B:
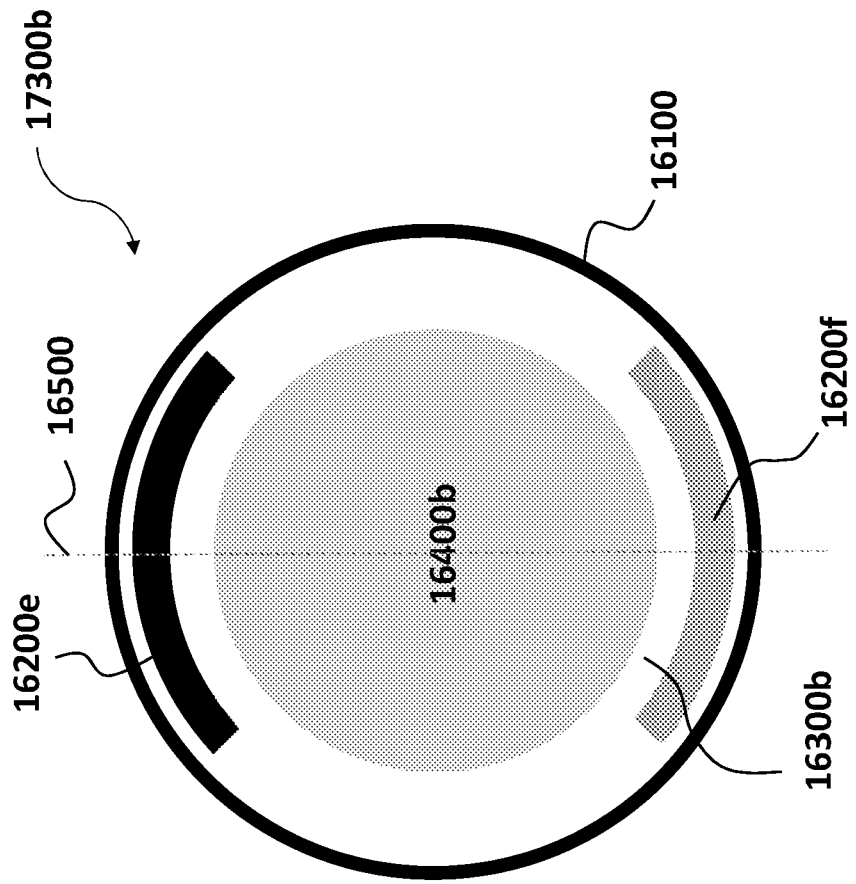
Figure 19B:
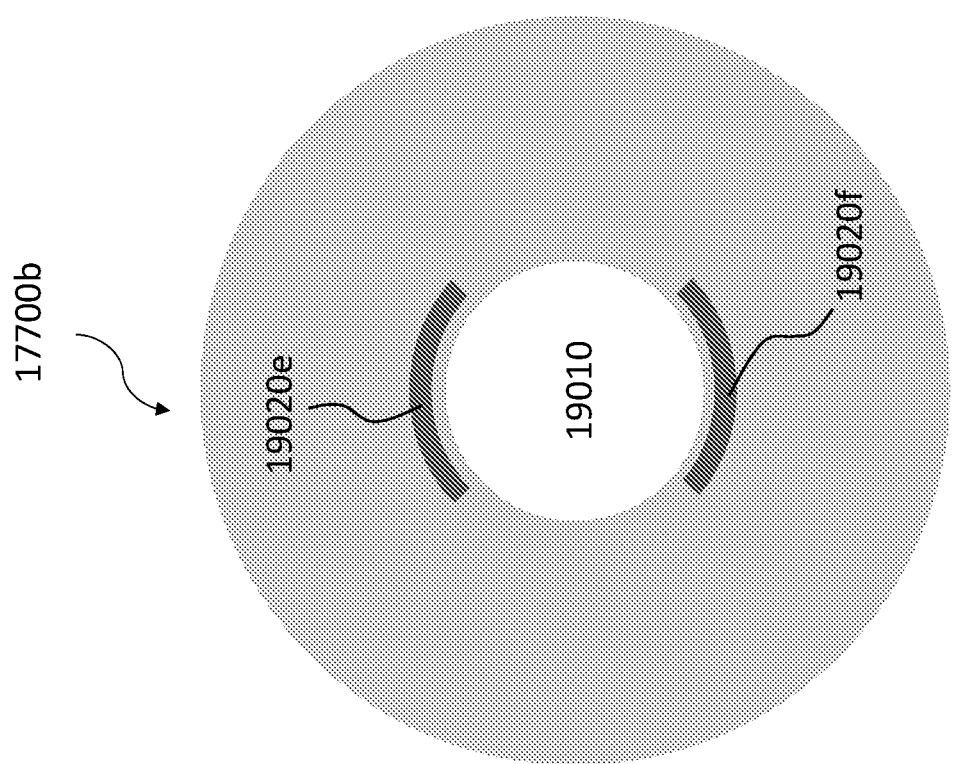

As shown in FIG. 16B, according to another embodiment of optical design pupil layout 17300b, two narrow areas 16200e and 16200f (at or near the pupil plane of an eye) can be allocated for two separate illumination patches from illumination sub-systems 19020e and 19020f (as shown in FIG. 19B) to illuminate the retina, and an area in a middle portion 16400b (at or near the pupil 17300 of eye) can be configured for imaging rays to pass through toward a baffle-and-illumination module from the retina of an eye. As can be seen in FIG. 16B, in some embodiments, only the upper illumination sub-system 19020e (as shown in FIG. 19B) can be active and the other illumination sub-systems can be inactive. According to an aspect of the embodiments, two images from different parts of a retina can be acquired by using each of the two illumination sub-systems.

Figure 16C:
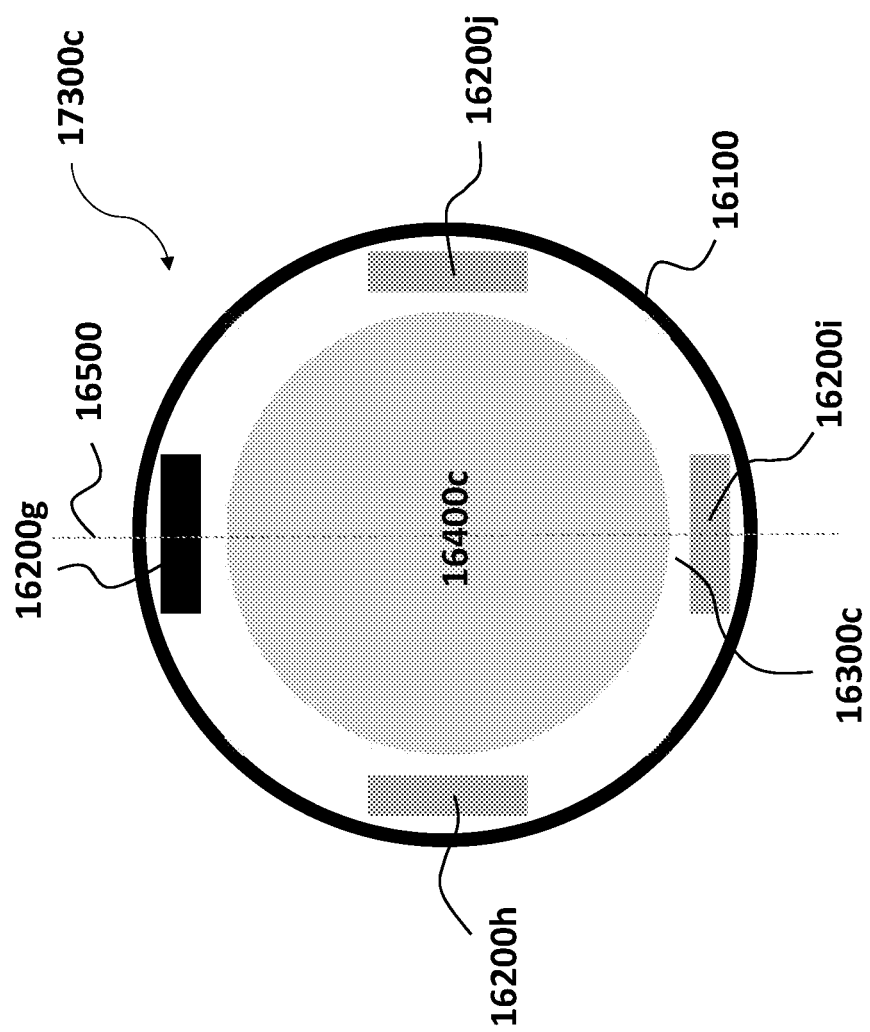
Figure 19C:
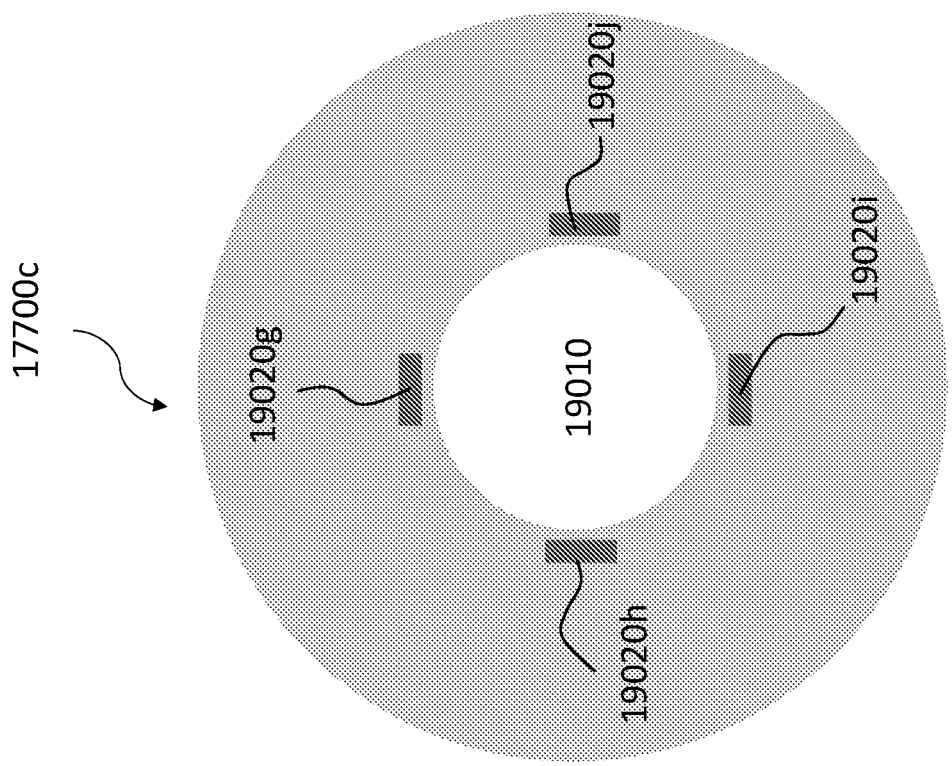

As shown in FIG. 16C, according to another embodiment of optical design pupil layout 17300c, four narrow areas 16200g, 16200h, 16200i, and 16200j (at or near the pupil plane of an eye) can be allocated for four separate illumination patches of illumination sub-systems 19020g, 19020h, 19020i and 19020j (as shown in FIG. 19C) to illuminate the retina, and an area in a middle portion 16400c (at or near the pupil plane 17300 of eye) can be configured for imaging rays to pass through toward a baffle-and-illumination module from the retina of an eye. As can be seen in FIG. 16C, in some embodiments, only the upper illumination sub-system 19020g (as shown in FIG. 19C) can be active and the other illumination sub-systems can be inactive. According to an aspect of the embodiments, four images from different parts of a retina can be acquired by using each of the four illumination sub-systems.

Figure 16D:
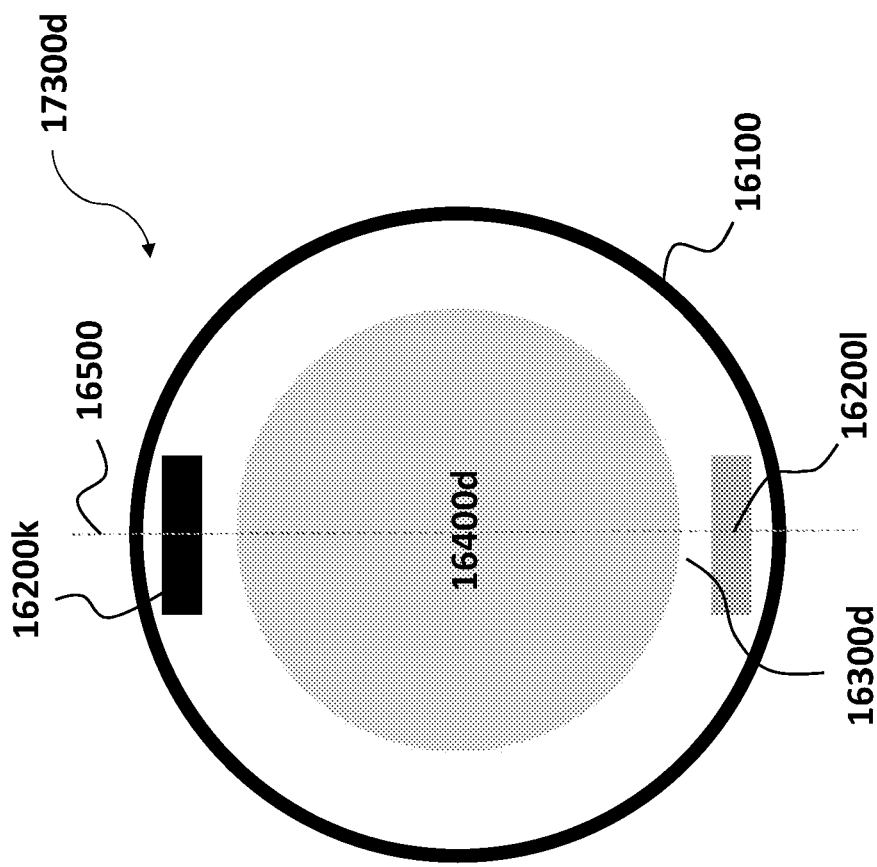
Figure 19D:
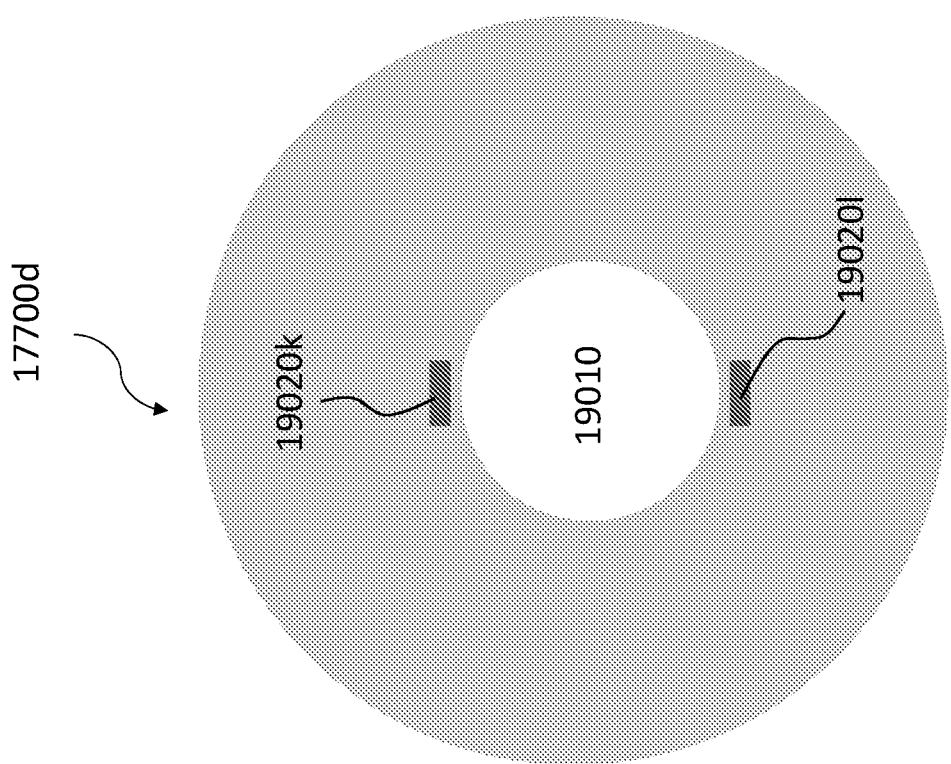

As shown in FIG. 16D, according to another embodiment of optical design pupil layout 17300d, two narrow areas 16200k and 16200l (at or near the pupil plane 17300 of an eye) can be allocated for two separate illumination patches from illumination sub-systems 19020k and 19020l (as shown in FIG. 19D) to illuminate the retina, and an area in a middle portion 16400d (at or near the pupil plane 17300 of eye) can be configured for imaging rays to pass through toward a baffle-and-illumination module from the retina of an eye. As can be seen in FIG. 16D, in some embodiments, only the upper illumination sub-system 19020k (as shown in FIG. 19D) can be active and the other illumination sub-system can be inactive. According to an aspect of the embodiments, two images from different parts of a retina can be acquired by using each of the two illumination sub-systems.

Figure 19E:
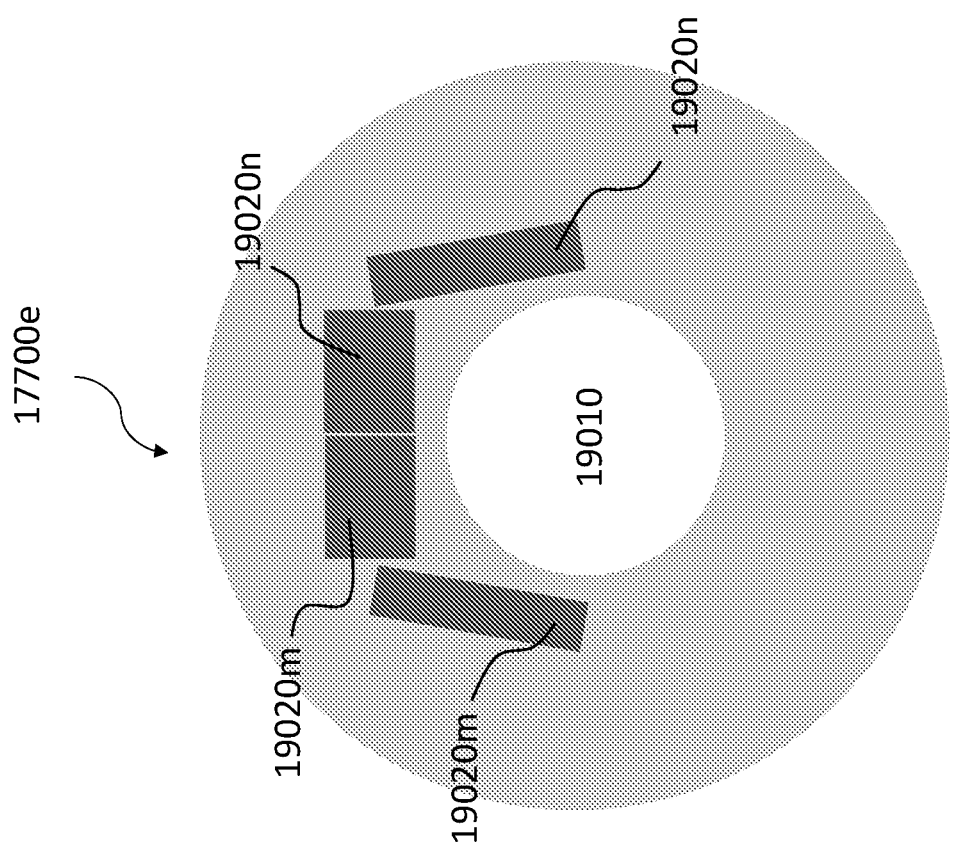

As shown in FIG. 16E, according to another embodiment of optical design pupil layout 17300e, two areas 16200m and 16200n (at or near the pupil plane of an eye) can be allocated for two separate illumination patches from illumination sub-systems 19020m and 19020n (as shown in FIG. 19E) to illuminate the retina, and a separate portion 16400e (at or near the pupil plane 17300 of eye) can be configured for imaging rays to pass through toward a baffle-and-illumination module from the retina of an eye. As can be seen in FIG. 16E, in some embodiments, only the left illumination sub-system 19020m (as shown in FIG. 19E) can be active and the other illumination sub-system can be inactive. According to an aspect of the embodiments, two images from different parts of a retina can be acquired by using each of the two illumination sub-systems.

Figure 16F:
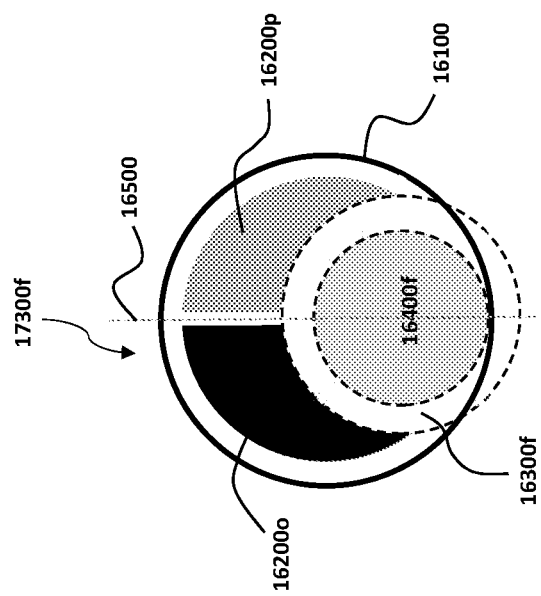
Figure 19F:
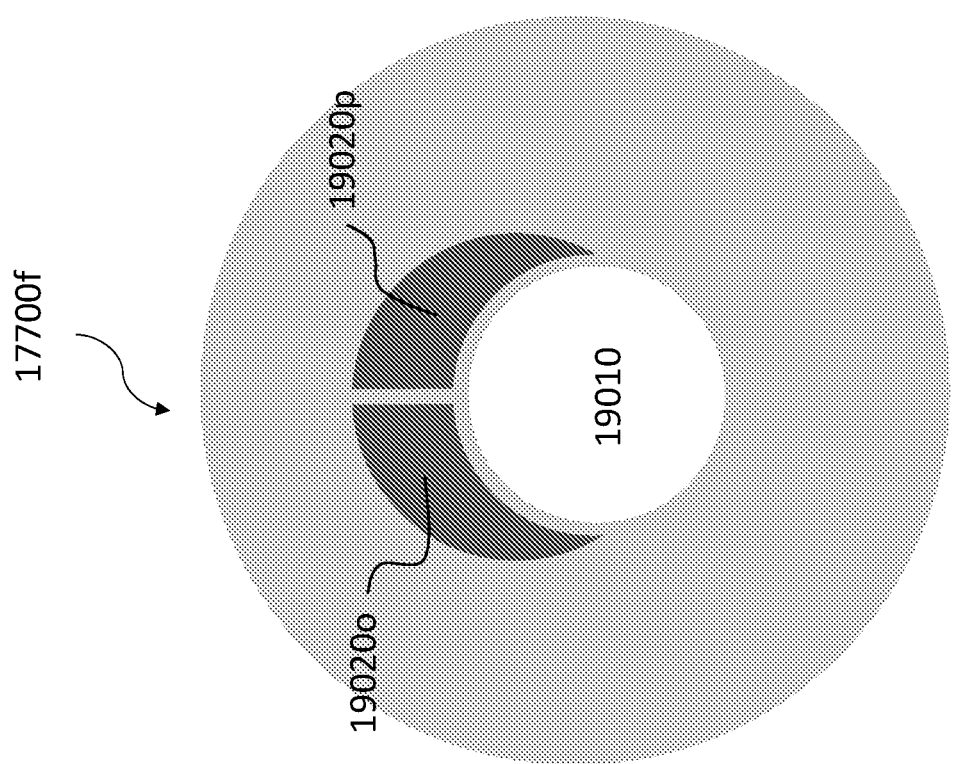

As shown in FIG. 16F, according to another embodiment of optical design pupil layout 17300f, two areas 16200o and 16200p (at or near the pupil plane 17300 of an eye) can be allocated for two separate illumination patches from illumination sub-systems 19020o and 19020p (as shown in FIG. 19F to illuminate the retina, and a separate portion 16400f (at or near the pupil plane 17300 of eye) can be configured for imaging rays to pass through toward a baffle-and-illumination module from the retina of an eye. As can be seen in FIG. 16F, in some embodiments, only the left illumination sub-system 19020o (as shown in FIG. 19F) can be active and the other illumination sub-system can be inactive. According to an aspect off the embodiments, two images from different parts of a retina can be acquired by using each of the two illumination sub-systems.

Referring to FIGS. 16A to 16F, according to one aspect of the example embodiments, buffer areas 16300a, 16300b, 16300c, 16300d, 16300e, and 16300f are disposed between an illumination patch (16200a to 16200p) and the area allocated to imaging rays (16400a to 16400f).

In certain embodiments of the optical design pupil layouts, these buffer areas can be relatively narrow because corneal reflections do not need to be removed completely due to the use of multiple image capture. The width of the buffer areas between the illumination patch and the path for imaging rays at or near the pupil 17300 of an eye can be close to the width of the illuminated patch shapes at or near the pupil 17300 of an eye or a little narrower than the width of the illuminated patch shapes at or near the pupil 17300 of an eye. In this regard, in an optical design pupil layout having a relatively narrow buffer area, the area in a middle portion (16400a to 16400f) at or near the pupil plane 17300 of an eye, which can be configured for imaging rays to pass through, can be expanded. These optical design pupil layouts of the present disclosure can be advantageous in several ways. First, a relatively wide area allocated to imaging rays can allow for the acquisition of higher resolution retinal images since the diffraction spot is relatively smaller. Second, a relatively wider area allocated to imaging rays at or near the pupil plane of an eye can provide for a higher signal-to-noise ("SNR") ratio by receiving more imaging rays (i.e., the signal) through the wider area, which can provide for higher contrast retinal images. For example, example embodiments of these optical design pupil layouts can be configured to image a retina through a small pupil (e.g., 2 mm of diameter). Some embodiments of these optical design pupil layouts can be configured to construct images having a relatively wide FOV (e.g., 60°×60° with two images captured or four images captured through a small pupil of an eye (e.g., 2 mm of diameter).

Referring again to FIGS. 16A to 16F, vertical reference line 16500 is provided to show the angle and direction of the example embodiments of these optical design pupil layouts. Those of skill in the art will recognize that the images of the illumination can be captured at different angles with respect to the vertical reference line 16500, other than 0°.

FIGS. 17, 18A to 18C are diagrammatic side views of various example embodiments of optical configurations for systems for retinal imaging.

Figure 17:
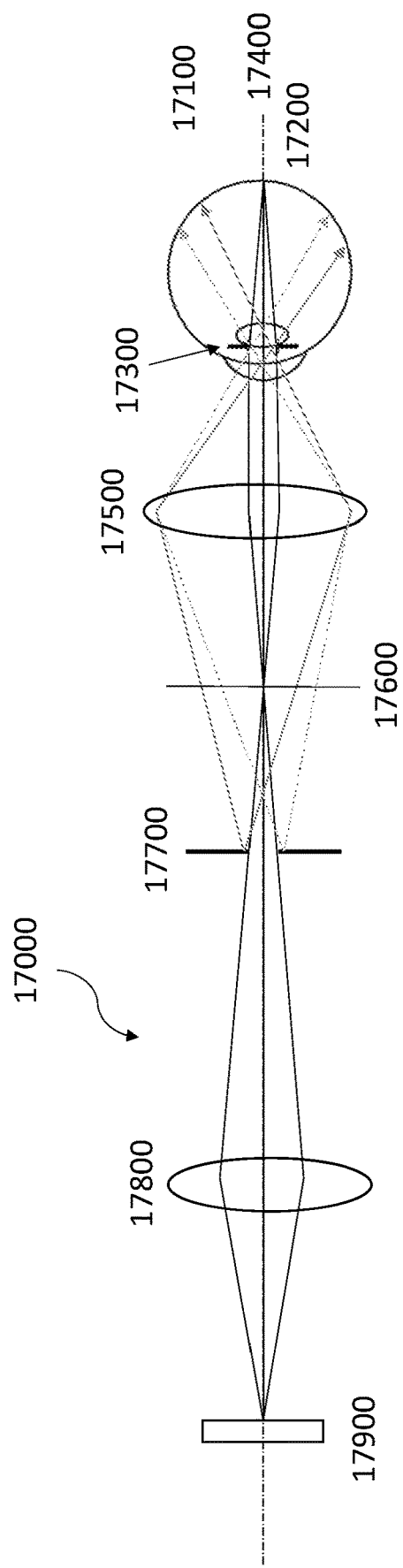
FIG. 17 is a side view of an example embodiment of an optical configuration for a system for retinal imaging.
Figure 18A:
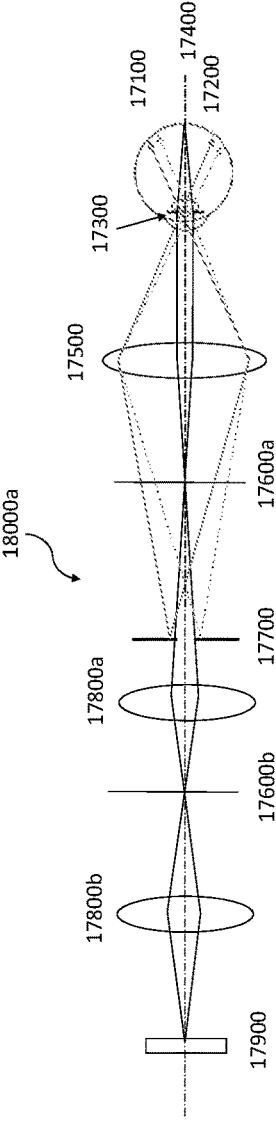
FIGS. 18A to 18C are side views of example embodiments of optical configurations for systems for retinal imaging.
Figure 18B:
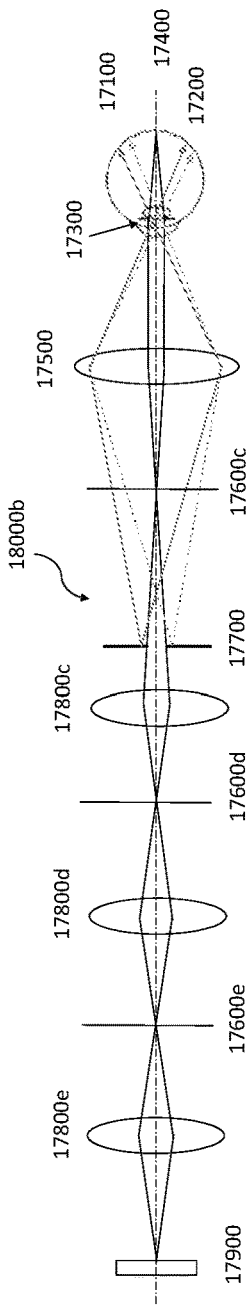
Figure 18C:
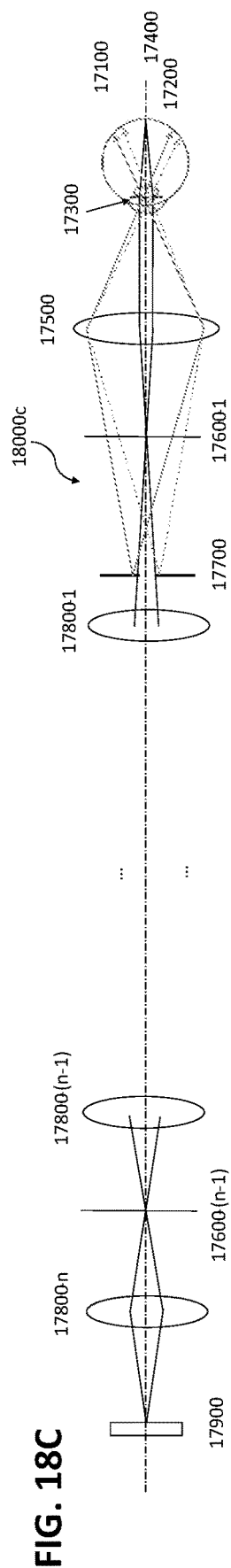

FIG. 17 is a diagrammatic side view illustrating an embodiment of an optical configuration of the system for retinal imaging 17000. According to one aspect of the embodiments, system for retinal imaging 17000 can be configured to image the retina 17200 of an eye 17100. In some embodiments, an optical axis 17400 of a system for retinal imaging 17000 can be configured in a coaxial relationship with the optical system of an eye to acquire high quality retinal images using the previously described embodiments of optical design pupil layouts, 17300a to 17300d (FIGS. 16A to 16D). In other embodiments, the optical axis 17400 of a system for retinal imaging 1700 can be offset by a predetermined distance from the optical system of an eye to acquire high quality retinal images using the previously described embodiments of optical design pupil layouts, 17300e and 17300f (FIGS. 16E and 16F).

According to one aspect of the embodiments, the optical configuration of a system for retinal imaging 17000 can comprise certain optical elements, including an objective lens 17500, a baffle-and-illumination module 17700, a reimaging corrective optics module 17800, and an image sensor 17900. Objective lens 17500 can be configured to focus a pattern of illumination onto or near an eye pupil plane and illuminate a retina, wherein the pattern of illumination can be created using the baffle-and-illumination module 17700 to generate light and the objective lens 17500 to focus the light using embodiments of the optical design pupil layouts 17300a to 17300f at or near a pupil plane 17300. According to some embodiments, the pattern of illumination can comprise one or more separate arc-shapes, one or more separate race-track shapes, one or more separate rectangles, or a combination of rectangles, rectangular shapes, parts of circles, or circular shapes. Objective lens 17500 can also be configured to relay and/or image the pupil of an eye onto an aperture of a baffle-and-illumination module 17700. Objective lens 17500 can also be configured to image to an advantageous position a plurality of imaging rays travelling from the retina through the pupil of an eye, which can allow a reimaging corrective optics module 17800 to image the retina onto an image sensor 17900 (e.g., for a relaxed eye). As can be seen in FIG. 17, the optical elements comprising an objective lens 17500 can be located between a pupil plane 17300 of an eye and a relayed retinal image 17600. In some embodiments, for example, objective lens 17500 can be configured to capture the plurality of imaging rays from the retina of an eye with a wide field of view of about 60°×60°.

According to another aspect of the embodiments, a reimaging corrective optics module 17800 can be configured to correct aberrations of a retinal image before the retinal image reaches an image sensor 17900, which can improve the image resolution, adjust diopter/astigmatism/focus, and/or change an image magnification. In some embodiments, the reimaging corrective optics module 17800 can comprise of multiple optical components. The reimaging corrective optics module 17800 can be located between the baffle-and-illumination module 17700 and an image sensor 17900.

According to another aspect of the embodiments, image sensor 17900 can be located at a final image plane. In other embodiments, the optical configuration of the imaging system of the system for retinal imaging 17000 can include two or more relayed retinal image (e.g., 17600*a* to 17600*d* and 17600-1 to 17600-(n-1) in FIGS. 18A, 18B and 18C), and can include multiple reimaging corrective optics modules (e.g. 17800*a* to 17800*e*, 17800-1 to 17800-*n* in FIGS. 18A, 18B and 18C).

According to another aspect of the embodiments, the baffle-and-illumination module 17700 can comprise one or more baffles and one or more illumination sub-systems, wherein the illumination sub-systems can be configured to provide sources of illumination. The sources of illumination can be configured to illuminate a retina of an eye through areas allocated for illumination on or near the eye pupil plane. Imaging rays reflected from the retina can pass through an aperture of the baffle-and-illumination module and a reimaging corrective optics module 17800 to be imaged onto an image sensor 17900 after being collected by objective lens 17500. In certain embodiments, the illumination sub-system(s) can comprise one or more light emitting diodes ("LEDs"), which can be configured to operate in a multitude of spectrum ranges (e.g., white, red, green, blue, near IR), and one or more waveguides configured to generate an emission shape and size depending on the optical design and optical design pupil layout chosen (at or near the pupil plane of an eye) for each illumination sub-system. The optical design pupil layout can comprise one of embodiments 17300*a* to 17300*f*.

In some embodiments, the baffle is an opaque structure with a hole aperture located therein and the baffle(s) can be configured to block partial reflections of undesired reflected light from the cornea of an eye and/or stray light other than the reflected light from the retina being imaged in the retinal image The baffle-and-illumination module 17700 can be located between a relayed retinal image 17600 and a reimaging corrective optics module 17800, as illustrated in FIG. 17.

FIGS. 19A to 19F are diagrams of example embodiments of single baffle-and-illumination modules. According to certain embodiments, baffle-and-illumination module 17700 can comprise a single baffle-and-illumination structure, including baffle 19050, aperture 19010, and one or more illumination sub-systems (also referred to as sub-modules) (e.g., 19020*a* to 19020*p*) located around aperture 19010.

Referring to FIG. 19A, according to some embodiments where an optical design pupil layout 17300*a*, such as that described with respect to FIG. 16A, is implemented, a single baffle-and-illumination structure 17700*a* can be configured to create a pattern according to the optical design pupil layout 17300*a* at or near the pupil plane of an eye.

Referring to FIG. 19B, according to other embodiments where an optical design pupil layout 17300*b*, such as that described with respect to FIG. 16B, is implemented, a single baffle-and-illumination structure 17700*b* can be configured to create a pattern according to the optical design pupil layout 17300*b* at or near the pupil plane of an eye.

Referring to FIG. 19C, according to other embodiments where an optical design pupil layout 17300*c*, such as that described with respect to FIG. 16C, is implemented, a single baffle-and-illumination structure 17700*c* can be configured to create a pattern according to the optical design pupil layout 17300*c* at or near the pupil plane of an eye.

Referring to FIG. 19D, according to other embodiments where an optical design pupil layout 17300*d*, such as that described with respect to FIG. 16D, is implemented, a single baffle-and-illumination structure 17700*d* can be configured to create a pattern according to the optical design pupil layout 17300*d* at or near the pupil plane of an eye.

Referring to FIG. 19E, according to other embodiments where an optical design pupil layout 17300*e*, such as that described with respect to FIG. 16E, is implemented, a single baffle-and-illumination structure 17700*e* can be configured to create a pattern according to the optical design pupil layout 17300*e* at or near the pupil plane of an eye.

Referring to FIG. 19F, according to other embodiments where an optical design pupil layout 17300*f*, such as that described with respect to FIG. 16F, is implemented, a single baffle-and-illumination structure 17700*f* can be configured to create a pattern according to the optical design pupil layout 17300*f* at or near the pupil plane of an eye.

Figure 20A:
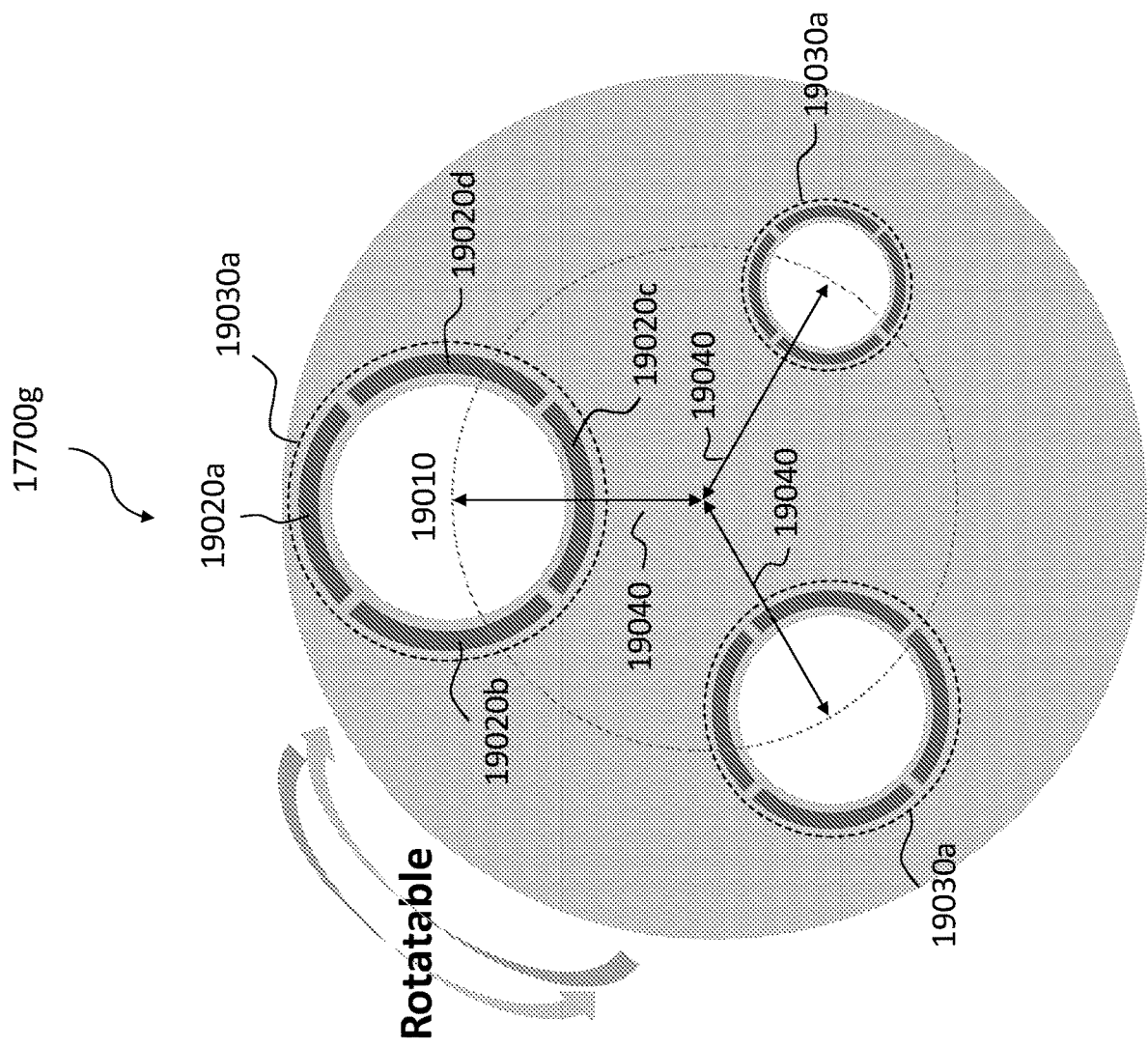
FIGS. 20A and 20B are diagrams of example embodiments of a multi-baffle-and-illumination module.
Figure 20B:
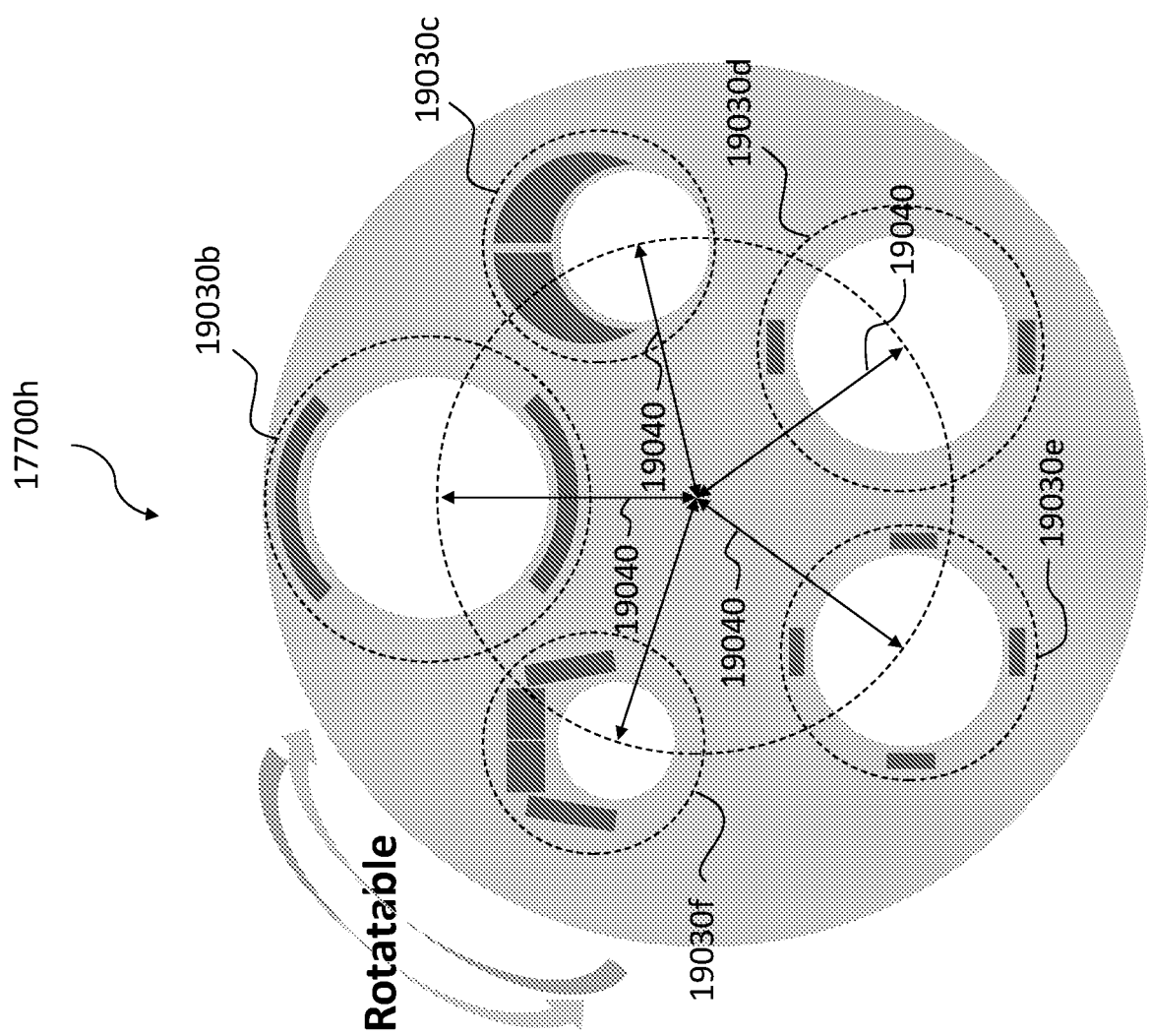

According to another aspect of some embodiments, baffle-and-illumination module 17700 can comprise a multi-baffle-and-illumination structure (e.g., shown as 17700*g* and 17700*h* in FIGS. 20A and 20B). FIGS. 20A and 20B are diagrams of example embodiments of the multi-baffle-and-illumination structure. According to certain embodiments, the multi-baffle-and-illumination structure can comprise a plurality of baffle-and-illumination sub-modules (e.g., 19030*a* to 19030*f*), wherein each sub-module can comprise an aperture and multiple illumination sub-systems around the aperture, each of which can operate in a manner similar to the single baffle-and-illumination structure described with respect to FIGS. 19A to 19F. According to some embodiments, each sub-module can be configured to use the same optical design pupil layout embodiment (e.g., 17300*a* to 17300*f*), as illustrated in FIG. 20A. In other embodiments, the sub-modules can be configured to use different optical design pupil layout embodiments, as illustrated in FIG. 20B. Those of skill in the art will further appreciate that the number and combination of sub-modules, baffles, and aperture sizes can vary, and that the embodiments shown in FIGS. 20A and 20B are meant to be illustrative only, and not limiting in any way.

According to another aspect of some embodiments, one or more of the baffle-and-illumination sub-modules can be configured to provide a suitable imaging mode for various ranges of pupil size (e.g., for pupil diameters of 3.0 mm to 4.0 mm, 2.0 mm to 3.0 mm, etc.). In some embodiments, one or more of the baffle-and-illumination sub-modules can be configured to provide a specific imaging mode (e.g., higher resolution imaging mode, 3D imaging mode, etc.).

Referring still to FIGS. 20A and 20B, the multi-baffle-and-illumination structure can provide multiple imaging modes in one device of an example embodiment of a system for retinal imaging 17000. According to another aspect of the embodiments, the multi-baffle-and-illumination structure can be rotatable in either or both of a clockwise and/or counterclockwise direction to prevent an entanglement of potentially connected lines to the multi-baffle-and-illumination module. In some embodiments, each baffle-and-illumination sub-module can be configured to be positioned at a certain distance 19040 from the center of the multi-baffle-and-illumination module (FIG. 20A, 20B). According to certain embodiments, each baffle-and-illumination sub-module can be configured in a coaxial relationship with an optical axis of an eye, where a certain optical design pupil layout (e.g., 17300*a*, 17300*b*, 17300*c*, or 17300*d*) is used for retinal imaging. In other embodiments, each baffle-and-illumination sub-module can be configured in an offset position by a predetermined distance from an optical system of an eye where a certain optical design pupil layout (e.g., 17300*e* or 17300*f*) is being used for retinal imaging.

According to some embodiments, a baffle-and-illumination sub-module can be automatically selected based on the information of pupil size measured by the integrated eye tracker.

According to other embodiments, a baffle-and-illumination sub-module for specific imaging mode (e.g., higher resolution imaging mode, 3D imaging mode, etc.) can be automatically selected based on the information of a patient's diseases or conditions.

Example Embodiments of Imaging and Sensing Technologies in Systems for Retinal Imaging Example embodiments of imaging and sensing technologies for use in systems for retinal imaging will now be described. In some embodiments, for example, a system for retinal imaging can be configured to utilize extended depth of field ("EDOF") technology, such as, for example, wavefront coding with the use of a phase plate and a computing system that is configured to reconstruct the final images of a retina. These systems can utilize post-image processing which can provide higher depth of focus and higher resolution. Higher depth of focus can provide more robust imaging for the system for retinal imaging because the working distance of the main device may not need to be as accurate due to the extended depth of field.

In some embodiments, a system for retinal imaging can be configured to use adaptive optics which may provide higher resolution.

In some embodiments, a system for retinal imaging can be configured to use tunable optical filters based on the technology of micro-electro-mechanical systems ("MEMS") Fabry-Perot interferometers, or piezo-actuated Fabry-Perot interferometers to acquire multi-spectral and/or hyper-spectral retinal images. According to one aspect of the embodiments, multiple image captures at various wavelengths can be performed in a timely fashion through the use of multiple quick succession flashes of various wavelength (which can appear as one flash to the human eye). The frequency of flashes can be selected so as not to create a risk of seizure in the patient.

In some embodiments, a system for retinal imaging can be configured to use vertical-cavity surface-emitting lasers ("VCSELs") and 3D sensors to provide 3D retinal imaging.

In some embodiments, a system for retinal imaging can be configured to use one or more electroactive lenses to acquire focused images at various depths of a retina. According to an aspect of the embodiments, the electroactive lenses can be configured to provide information relating to 3D images/video of a retina and depth information, such as a depth map of a retina (e.g., near optical disk).

In some embodiments, a system for retinal imaging can be configured to use one or more plates comprising a birefringent material, such as calcite, and a computing system configured to acquire and process information relating to 3D imaging/video of a retina and depth information, such as depth map of a retina (e.g., near optical disk) with the use of birefractive stereo algorithms.

In some embodiments, a system for retinal imaging can be configured to use a pinhole and an illumination source, wherein retinal imaging can be split section by section in an emission area, and each section of the emission area can be used one-by-one continuously and integrated by the system for retinal imaging for confocal imaging.

In some embodiments, a system for retinal imaging can be configured to use tunable optical filters based on the technology of MEMS Fabry-Perot interferometers or piezo-actuated Fabry-Perot interferometers to acquire information relating to an anterior chamber of an eye.

In some embodiments, a system for retinal imaging can be integrated with an optical polarimetry using VCSELs in order to monitor glucose.

In some embodiments, a system for retinal imaging can be integrated with one or more high speed video systems.

Example Embodiments of Systems for Multiple Image Capture

Example embodiments of systems for multiple image capture will now be described. FIG. 21A is a diagram of an example embodiment of an optical design pupil layout (at or near the pupil plane of an eye) for a system for retinal imaging where only the top illumination sub-system is active and the other illumination sub-systems are inactive. FIG. 21B is a diagram of a simulated image from the aforementioned system for retinal imaging, wherein the system is configured to image a pupil of 4.0 mm diameter based on the design illustrated in FIG. 16A (where only the top illumination sub-system is active). FIG. 21C is a diagram of a simulated image from the aforementioned system for retinal imaging, wherein the system is configured for imaging a pupil of 2.0 mm diameter based on the design illustrated in FIG. 16A (where only the top illumination sub-system is active).

FIG. 22A is a diagram of the same embodiment of an optical design pupil layout for a system for retinal imaging as that described with respect to FIG. 21A, except only the left illumination sub-system is active and the other illumination sub-systems are inactive. FIG. 22B is a diagram of a simulated image from the aforementioned system for retinal imaging, wherein the system is configured to image a pupil of 4.0 mm diameter based on the design illustrated in FIG. 22A (where only the left illumination sub-system is active). FIG. 22C is a diagram of a simulated image from the aforementioned system for retinal imaging, wherein the system is configured to image a pupil of 2.0 mm diameter based on the design illustrated in FIG. 22A (where only the left illumination sub-system is active).

FIG. 23A is a diagram of the same embodiment of an optical design pupil layout for a system for retinal imaging as that described with respect to FIG. 21A, except only the bottom illumination sub-system is active and the other illumination sub-systems are inactive. FIG. 23B is a diagram of a simulated image from the aforementioned system for retinal imaging, wherein the system is configured to image a pupil of 4.0 mm diameter based on the design illustrated in FIG. 23A (where only the bottom illumination sub-system is active). FIG. 23C is a diagram of a simulated image from the aforementioned system for retinal imaging, wherein the system is configured to image a pupil of 2.0 mm diameter based on the design illustrated in FIG. 23A (where only the bottom illumination sub-system is active).

FIG. 24A is a diagram of the same embodiment of an optical design pupil layout for a system for retinal imaging as that described with respect to FIG. 21A, except only the right illumination sub-system is active and the other illumination sub-systems are inactive. FIG. 24B is a diagram of a simulated image from the aforementioned system for retinal imaging, wherein the system is configured to image a pupil of 4.0 mm diameter based on the design illustrated in FIG. 19A (where only the right illumination sub-system is active). FIG. 24C is a diagram of a simulated image from the aforementioned system for retinal imaging, wherein the system is configured to image a pupil of 2.0 mm diameter based on the design illustrated in FIG. 24A (where only the right illumination sub-system is active).

Referring to FIGS. 21B, 21C, 22B, 22C, 23B, 23C, 24B, and 24C, according to one aspect of the embodiments, each of the images (21000*g*, 21000*h*, 21000*i*, 21000*j*, 22000*g*, 22000*h*, 22000*i*, or 22000*j*) have been captured with a different illumination sub-system and can contain parts of corneal reflections (21100*g*, 21100*h*, 21100*i*, or 21100*j*)) as a result of a narrow buffer area between the illumination and the area where the imaging rays pass at or near the pupil plane of an eye. However, each image using a different illumination sub-system can contain a different portion of a retina image free from corneal reflections. Therefore, according to one aspect of the embodiments, a final image can be combined from all the images of different portions of the retina free from corneal reflections thereby creating a complete image of the retina of a target FOV free from corneal reflections.

Figure 25C:
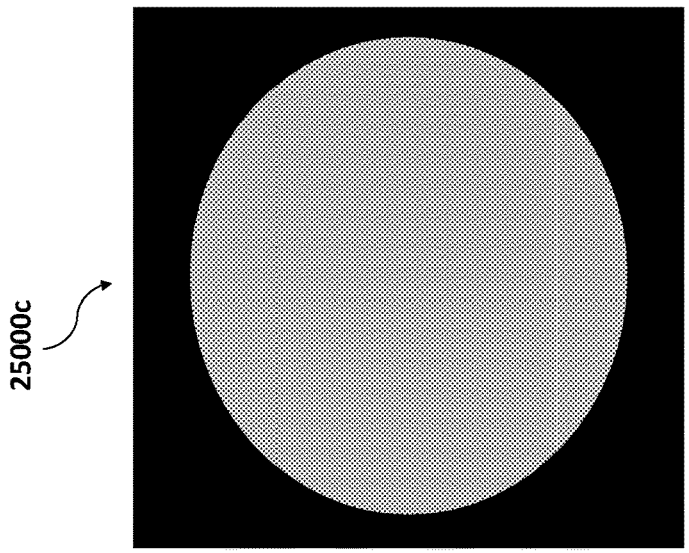
FIGS. 25A to 25C are diagrams of final images combined from multiple images captured by using multiple illumination sub-systems.
Figure 25B:
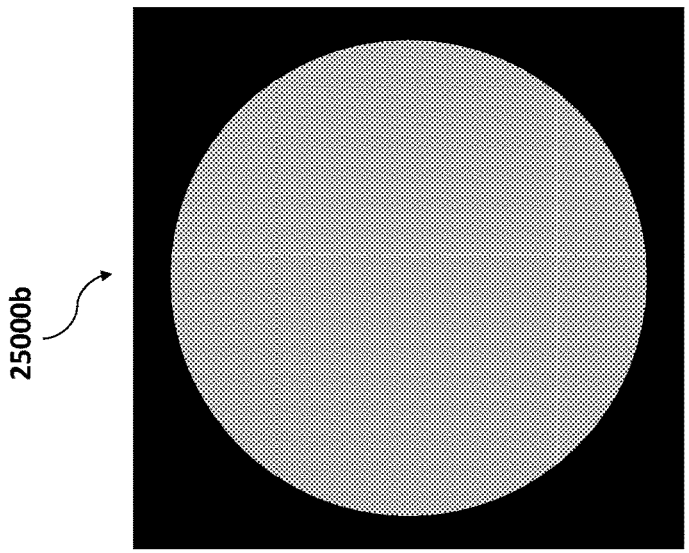
Figure 25A:
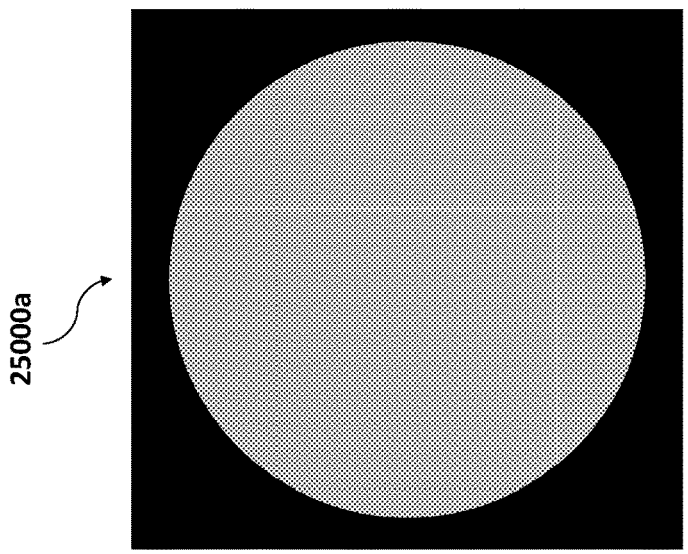

FIG. 25A is a diagram of a final image 25000*a* combined from four images 21000*g* to 21000*j*. FIG. 25B is a diagram of a final image 25000*b* combined from four images 22000*g* to 22000*j*. FIG. 25C is a diagram of a final image 25000*c* combined from two images 21000*g* and 21000*i*. The FOV of 25000*a* and 25000*b* can be high (e.g., 60° H×60° V or higher). The lateral FOV of final image 25000*c* can be as high as final image 25000*a* and final image 25000*b*, but lower in a vertical direction (e.g., 60° H×50° V). The combined final image can be provided to a physician and/or grading specialist to screen, diagnose, and monitor diseases of interest, and to monitor a medical and/or health condition of a patient. In addition, the computing system for AI-based screening/diagnosis/monitoring 1300 can utilize images of different portions of the retina without the corneal reflections, without combining the images, in order to analyze, screen, diagnose and/or monitor diseases of interest, and to monitor a medical and/or health condition of a patient.

According to another aspect of the embodiments, the illumination sub-systems can be electronically controlled to be active or inactive without requiring any mechanical movement during the image capturing process (e.g., four image or two image captures). In this regard, imaging can be performed rapidly by using multiple quick succession flashes for the image captures, which can appear as one flash to the human eye.

Throughout this disclosure, the preferred embodiment and examples illustrated should be considered as exemplars, rather than as limitations on the present inventive subject matter, which includes many inventions. As used herein, the term "inventive subject matter," "system," "device," "apparatus," "method," "present system," "present device," "present apparatus" or "present method" refers to any and all of the embodiments described herein, and any equivalents.

It should also be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

When an element or feature is referred to as being "on" or "adjacent" to another element or feature, it can be directly on or adjacent the other element or feature or intervening elements or features may also be present. In contrast, when an element is referred to as being "directly on" or extending "directly onto" another element, there are no intervening elements present. Additionally, when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Furthermore, relative terms such as "inner," "outer," "upper," "top," "above," "lower," "bottom," "beneath," "below," and similar terms, may be used herein to describe a relationship of one element to another. Terms such as "higher," "lower," "wider," "narrower," and similar terms, may be used herein to describe angular relationships. It is understood that these terms are intended to encompass different orientations of the elements or system in addition to the orientation depicted in the figures.

Although the terms first, second, third, etc., may be used herein to describe various elements, components, regions, and/or sections, these elements, components, regions, and/or sections should not be limited by these terms. These terms are only used to distinguish one element, component, region, or section from another. Thus, unless expressly stated otherwise, a first element, component, region, or section discussed below could be termed a second element, component, region, or section without departing from the teachings of the inventive subject matter. As used herein, the term "and/or" includes any and all combinations of one or more of the associated list items.

The terminology used herein is for the purpose of describing particular embodiments only and is not intended to be limiting. As used herein, the singular forms "a," "an," and "the" are intended to include the plural forms as well, unless the context clearly indicates otherwise. For example, when the present specification refers to "an" assembly, it is understood that this language encompasses a single assembly or a plurality or array of assemblies. It will be further understood that the terms "comprises," "comprising," "includes," and/or "including" when used herein, specify the presence of stated features, integers, steps, operations, elements, and/or components, but do not preclude the presence or addition of one or more other features, integers, steps, operations, elements, components, and/or groups thereof.

Embodiments are described herein with reference to view illustrations that are schematic illustrations. As such, the actual thickness of elements can be different, and variations from the shapes of the illustrations as a result, for example, of manufacturing techniques and/or tolerances are expected. Thus, the elements illustrated in the figures are schematic in nature and their shapes are not intended to illustrate the precise shape of a region and are not intended to limit the scope of the inventive subject matter.

The foregoing is intended to cover all modifications, equivalents and alternative constructions falling within the spirit and scope of the invention as expressed in the appended claims, wherein no portion of the disclosure is intended, expressly or implicitly, to be dedicated to the public domain if not set forth in the claims. Furthermore, any features, functions, steps, or elements of the embodiments may be recited in or added to the claims, as well as negative limitations that define the inventive scope of the claims by features, functions, steps, or elements that are not within that scope.

What is claimed is:

1. A system for retinal imaging comprising:
   optical elements comprising an objective lens, the optical elements being configured to:
   focus patterns of illumination on or near a pupil of an eye and illuminate a retina, relay and image the pupil onto a baffle-and-illumination module, and focus a plurality of imaging rays arriving from the retina through the pupil to allow at least one reimaging corrective optical module to image the retina onto at least one image sensor;
   the baffle-and-illumination module comprising one or more baffles and one or more illumination sub-modules, wherein each of the one or more illumination sub-modules comprises one or more light sources of a plurality of spectrum ranges and one or more waveguides configured to generate emissions of shapes and sizes to produce the patterns of illumination, wherein at least one of the one or more baffles is an opaque structure comprising an aperture, and wherein the at least one of the one or more baffles is configured to block light other than a reflected light from the retina;
   the at least one reimaging corrective optical module comprising one or more optical components configured to correct aberrations, adjust diopter, adjust astigmatism, adjust focus, or change image magnification of a retinal image before the retinal image reaches the at least one image sensor and the at least one image sensor; and
   a control unit configured to dynamically adjust one or more imaging parameters in real-time, including focus and light intensity, wherein the adjustments are made during the imaging process to optimize image quality based on the anatomical characteristics of the patient's eye.

2. The system of claim 1, wherein the optical elements are disposed between a pupil plane and a relayed retinal image, wherein the baffle-and-illumination module is disposed between the relayed retinal image and the at least one reimaging corrective optical module, wherein the at least one reimaging corrective optical module is disposed between the baffle-and-illumination module and the at least one image sensor, and wherein the at least one image sensor is disposed at a final image plane.

3. The system of claim 1, wherein the patterns of illumination on or near the pupil comprise one or more separate arc-shapes, one or more separate race-track shapes, one or more separate rectangles, or a combination of rectangles, rectangular shapes, parts of circles, or circular shapes.

4. The system of claim 1, wherein the baffle-and-illumination module comprises a single baffle-and-illumination structure or a multi-baffle-and-illumination structure, wherein the single baffle-and-illumination structure comprises a baffle including an aperture and one or more illumination sub-modules around the aperture, and wherein the multi-baffle-and-illumination structure comprises a plurality of baffles containing apertures of various sizes and locations and one or more illumination sub-modules around each aperture.

5. The system of claim 4, wherein a center of the aperture in the single baffle-and-illumination structure is configured in a coaxial relationship with an optical axis of the eye when the system for retinal imaging is correctly aligned.

6. The system of claim 4, wherein the multi-baffle-and-illumination structure is rotatable, and wherein a center of each of the plurality of apertures of the multi-baffle-and-illumination structure is configured in a coaxial relationship with an optical axis of the eye when the system for retinal imaging is correctly aligned.

7. The system of claim 1, wherein each of the one or more illumination sub-modules is configured to capture a partial retinal image comprising a partial corneal reflection and a portion of the retina without corneal reflections, and wherein the system for retinal imaging is configured to create a final image combined from the captured partial retina images, wherein the final image comprises a complete image of the retina according to a target field-of-view that is free of corneal reflections.

8. The system of claim 1, wherein each of the one or more illumination sub-modules is configured to be turned on and off separately with an electronic controller.

9. The system of claim 1, wherein the optical elements and the baffle-and-illumination module are configured to operate together to capture the retinal image using a plurality of quick flashes in succession that appear as a single flash to the eye.

10. The system of claim 4, wherein the multi-baffle-and-illumination structure is configured to provide a plurality of retinal imaging modes, each of which is adapted for a different range of pupil diameters.

11. The system of claim 4, wherein the multi-baffle-and-illumination structure is configured to provide a plurality of imaging modes comprising one or more of a high resolution imaging mode and a three-dimensional imaging mode.

* * * * *